US012578342B2

(12) United States Patent
Matray et al.

(10) Patent No.: US 12,578,342 B2
(45) Date of Patent: Mar. 17, 2026

(54) POLYMERIC DYES HAVING A BACKBONE COMPRISING ORGANOPHOSPHATE UNITS

(71) Applicant: SONY CORPORATION, Tokyo (JP)

(72) Inventors: Tracy Matray, Snohomish, WA (US); Sharat Singh, Rancho Santa Fe, CA (US)

(73) Assignee: SONY GROUP CORPORATION, Tokyo (JP)

( * ) Notice: Subject to any disclaimer, the term of this patent is extended or adjusted under 35 U.S.C. 154(b) by 1196 days.

(21) Appl. No.: 17/259,845

(22) PCT Filed: Jul. 12, 2019

(86) PCT No.: PCT/US2019/041642
§ 371 (c)(1),
(2) Date: Jan. 12, 2021

(87) PCT Pub. No.: WO2020/014634
PCT Pub. Date: Jan. 16, 2020

(65) Prior Publication Data

US 2021/0285953 A1 Sep. 16, 2021

Related U.S. Application Data

(60) Provisional application No. 62/697,716, filed on Jul. 13, 2018.

(51) Int. Cl.
*G01N 33/58* (2006.01)
*C07F 9/53* (2006.01)
(Continued)

(52) U.S. Cl.
CPC ............ *G01N 33/582* (2013.01); *C07F 9/53* (2013.01); *C09B 69/109* (2013.01); *G01N 1/30* (2013.01);
(Continued)

(58) Field of Classification Search
None
See application file for complete search history.

(56) References Cited

U.S. PATENT DOCUMENTS 4,450,305 A 5/1984 Kamhi
4,476,229 A 10/1984 Fino et al.
(Continued)

FOREIGN PATENT DOCUMENTS

CA 2263671 A1 2/1998
CN 102174078 A 9/2011
(Continued)

OTHER PUBLICATIONS

Leung et al (in Bioorganic & Medicinal Chemistry Letters 9 (1999) 2229-2232) (Year: 1999).*
(Continued)

*Primary Examiner* — Rachel Kahn
(74) *Attorney, Agent, or Firm* — Seed Intellectual Property Law Group LLP

(57) ABSTRACT

Compounds useful as fluorescent or colored dyes are disclosed. The compounds have the structure (I) or a stereoisomer, tautomer or salt thereof, wherein $R^1$, $R^2$, $R^3$, $R^4$, $R^5$, $L^{1a}$, $L^{1b}$, $L^2$, $L^3$, $L^4$, $L^5$, $L^6$, $L^7$, $M^1$, $M^2$, q, w, m and n are as defined herein. Methods associated with preparation and use of such compounds are also provided.

25 Claims, 28 Drawing Sheets

(51) Int. Cl.
*C09B 69/10* (2006.01)
*G01N 1/30* (2006.01)
*G01N 33/537* (2006.01)

(52) U.S. Cl.
CPC ..... *G01N 33/537* (2013.01); *G01N 2001/302* (2013.01)

(56) References Cited

U.S. PATENT DOCUMENTS 4,778,753 A 10/1988 Yamanishi et al.
5,053,054 A 10/1991 Kirchanski
5,268,486 A 12/1993 Waggoner et al.
5,318,894 A 6/1994 Pugia
5,582,977 A 12/1996 Yue et al.
5,696,157 A * 12/1997 Wang .................. C07D 311/16 549/288
5,698,391 A 12/1997 Cook et al.
5,886,177 A 3/1999 Cook et al.
5,994,143 A 11/1999 Bieniarz et al.
6,005,093 A 12/1999 Wood et al.
6,140,480 A 10/2000 Kool
6,171,859 B1 1/2001 Herrnstadt et al.
6,218,108 B1 4/2001 Kool
6,365,730 B1 4/2002 Jennings et al.
6,380,431 B1 4/2002 Whipple et al.
6,479,650 B1 11/2002 Kool
6,514,700 B1 2/2003 Singh
6,534,041 B1 3/2003 Licha et al.
6,627,400 B1 9/2003 Singh et al.
6,670,193 B2 12/2003 Kool
6,716,452 B1 4/2004 Piccariello et al.
6,852,709 B2 2/2005 Leong et al.
7,038,063 B2 5/2006 Lee et al.
7,060,708 B2 6/2006 Piccariello et al.
7,172,907 B2 2/2007 Chen et al.
7,423,133 B2 9/2008 Kool et al.
7,667,024 B2 2/2010 Mao et al.
7,897,684 B2 3/2011 Bazan et al.
8,008,522 B2 8/2011 Lukhtanov et al.
8,101,776 B2 1/2012 Berens et al.
8,153,706 B2 4/2012 Vasudevan
8,217,389 B2 7/2012 Nakano et al.
8,293,700 B2 10/2012 Arranz
8,349,308 B2 1/2013 Yurkovetskiy et al.
8,354,515 B2 1/2013 Ueno et al.
8,431,545 B2 4/2013 Kataoka et al.
8,491,993 B2 7/2013 Nguyen et al.
8,546,590 B2 10/2013 Gall
8,632,947 B2 1/2014 Bentley et al.
8,802,738 B2 8/2014 Emrick
8,895,023 B2 11/2014 Rademacher et al.
8,906,603 B2 12/2014 Castro et al.
8,946,394 B2 2/2015 Na et al.
9,029,537 B2 5/2015 Koch
9,085,799 B2 7/2015 Bazan et al.
9,150,782 B2 10/2015 Lee et al.
9,400,273 B1 7/2016 Liu et al.
9,545,447 B2 1/2017 Wooley et al.
9,649,389 B2 5/2017 Groves et al.
9,687,291 B2 6/2017 Shimizu et al.
9,689,877 B2 6/2017 Matray et al.
9,696,310 B2 7/2017 Margulies et al.
9,714,946 B2 7/2017 Bradner et al.
9,765,220 B2 9/2017 Matray et al.
9,822,134 B2 11/2017 Segev
9,851,359 B2 12/2017 Matray et al.
9,884,070 B2 2/2018 Denardo et al.
9,910,051 B2 3/2018 Beacham et al.
9,913,992 B2 3/2018 Demarest et al.
9,932,578 B2 4/2018 Feinstein et al.
9,939,454 B2 4/2018 Dzubay et al.
10,036,754 B2 7/2018 Matray et al.
10,191,060 B2 1/2019 Chiu et al.
10,435,563 B2 10/2019 Matray et al.
10,617,670 B2 4/2020 Sapra et al.
10,709,791 B2 7/2020 Stayton et al.
10,834,091 B2 11/2020 Deninno et al.
10,865,310 B2 12/2020 Matray et al.
10,866,244 B2 12/2020 Matray et al.
10,954,391 B2 3/2021 Matray et al.
10,989,715 B2 4/2021 Matray et al.
11,013,756 B2 5/2021 Haruta et al.
11,084,932 B2 8/2021 Battrell et al.
11,142,647 B2 10/2021 Matray et al.
11,312,736 B1 4/2022 Matray et al.
11,352,502 B2 6/2022 Matray et al.
11,370,922 B2 6/2022 Matray et al.
11,377,563 B2 7/2022 Matray et al.
11,390,754 B2 7/2022 Singh et al.
11,434,374 B2 9/2022 Matray et al.
11,434,377 B2 9/2022 Matray et al.
11,453,783 B2 9/2022 Matray et al.
11,618,906 B2 4/2023 Steele et al.
11,685,835 B2 6/2023 Matray
11,827,661 B2 11/2023 Battrell et al.
11,874,280 B2 1/2024 Jackson et al.
11,931,419 B2 3/2024 Matray
11,945,955 B2 4/2024 Matray et al.
12,006,438 B2 6/2024 Singh et al.
12,018,159 B2 6/2024 Matray et al.
2001/0018503 A1 8/2001 Whipple et al.
2002/0012947 A1 1/2002 Bevers et al.
2002/0099013 A1 7/2002 Piccariello et al.
2002/0142329 A1 10/2002 Matray et al.
2003/0054361 A1 3/2003 Heller
2003/0207208 A1 11/2003 Uenishi
2003/0207264 A1 11/2003 Packard et al.
2004/0014981 A1 1/2004 Lugade et al.
2004/0067498 A1 4/2004 Chenna et al.
2004/0096825 A1 5/2004 Chenna et al.
2004/0138467 A1 7/2004 French et al.
2004/0186278 A1 9/2004 Chen et al.
2004/0224372 A1 11/2004 Li et al.
2004/0241768 A1 12/2004 Whitten et al.
2005/0054024 A1 3/2005 Lawrence
2005/0123935 A1 6/2005 Haugland et al.
2006/0008822 A1 1/2006 Manoharan et al.
2006/0035302 A1 2/2006 Lee
2006/0063186 A1 3/2006 Benson et al.
2007/0042398 A1 2/2007 Peng et al.
2007/0077549 A1 4/2007 Buller et al.
2007/0148094 A1 6/2007 Uzgiris
2007/0269902 A1 11/2007 Beechem et al.
2008/0227939 A1 9/2008 Mizoshita et al.
2009/0253792 A1 10/2009 Mickle et al.
2009/0299070 A1 12/2009 Berens et al.
2010/0039684 A1 2/2010 Kolb et al.
2010/0092386 A1 4/2010 Segev
2010/0129800 A1 5/2010 Aymami Bofarull et al.
2010/0192312 A1 8/2010 Cremer et al.
2010/0248385 A1 9/2010 Tan et al.
2011/0014599 A1 * 1/2011 Akhavan-Tafti ..... C07D 417/04 435/5
2011/0224516 A1 9/2011 Romey et al.
2012/0021454 A1 1/2012 Bikker et al.
2012/0116079 A1 5/2012 Lukhtanov et al.
2012/0126175 A1 5/2012 Ueno et al.
2013/0059343 A1 3/2013 Cheung
2013/0102021 A1 4/2013 Beacham et al.
2013/0119363 A1 5/2013 Sasaki et al.
2013/0137755 A1 5/2013 Segev
2013/0202536 A1 8/2013 Mustaev et al.
2013/0244891 A1 9/2013 Waggoner et al.
2014/0023590 A1 1/2014 Gao et al.
2014/0193504 A1 7/2014 Wooley et al.
2014/0275508 A1 9/2014 Scarr et al.
2015/0030541 A1 1/2015 Rogers
2015/0110715 A1 4/2015 Eder et al.
2015/0159198 A1 6/2015 McGall et al.
2015/0232615 A1 8/2015 Kwiatkowski
2015/0258217 A1 9/2015 Caravan
2016/0039850 A1 2/2016 Segev
2016/0176903 A1 6/2016 Segev
2016/0208100 A1 7/2016 Matray et al.

(56) References Cited

U.S. PATENT DOCUMENTS

2016/0264737 A1 9/2016 Bartholomew et al.
2016/0327859 A1 11/2016 Idei et al.
2016/0341736 A1 11/2016 Matray et al.
2016/0347907 A1 12/2016 Dose
2017/0286113 A1 10/2017 Shanbhogue et al.
2017/0292957 A1 10/2017 Matray et al.
2017/0326233 A1 11/2017 Demeule et al.
2018/0065998 A1 3/2018 Battrell et al.
2018/0079909 A1 3/2018 Matray et al.
2018/0092993 A1 4/2018 Desai et al.
2018/0100861 A1 4/2018 Matray et al.
2018/0141935 A1 5/2018 Josel et al.
2018/0163052 A1 6/2018 Matray et al.
2018/0164322 A1 6/2018 Matray et al.
2018/0237641 A1 8/2018 Matray et al.
2018/0312468 A1 11/2018 Zhang et al.
2019/0016898 A1 1/2019 Matray et al.
2019/0136065 A1 5/2019 Singh et al.
2019/0144678 A1 5/2019 Matray et al.
2019/0153232 A1 5/2019 Matray et al.
2019/0177549 A1 6/2019 Matray et al.
2019/0300716 A1 10/2019 Matray et al.
2020/0032139 A1 1/2020 Behrendt et al.
2020/0109287 A1 4/2020 Matray et al.
2020/0164085 A1 5/2020 Brandish et al.
2020/0222554 A1 7/2020 Matray et al.
2020/0284798 A1 9/2020 Matray et al.
2020/0330610 A1 10/2020 Desai et al.
2020/0353089 A1 11/2020 Matray
2020/0353094 A1 11/2020 Matray
2020/0360526 A1 11/2020 Matray
2020/0392345 A1 12/2020 Matray et al.
2021/0032277 A1 2/2021 Matray et al.
2021/0032474 A1 2/2021 Matray et al.
2021/0095130 A1 4/2021 Matray et al.
2021/0096135 A1 4/2021 Matray et al.
2021/0109104 A1 4/2021 Jackson et al.
2021/0128591 A1 5/2021 Matray
2021/0128739 A1 5/2021 Matray
2021/0139440 A1 5/2021 Ramsden et al.
2021/0253864 A1 8/2021 Matray et al.
2021/0261782 A1 8/2021 Matray et al.
2021/0285953 A1 9/2021 Matray et al.
2021/0340380 A1 11/2021 Matray et al.
2021/0395530 A1 12/2021 Matray et al.
2022/0160887 A1 5/2022 Matray et al.
2022/0168433 A1 6/2022 Matray et al.
2022/0168435 A1 6/2022 Matray et al.
2022/0175951 A1 6/2022 Boitano et al.
2022/0220314 A1 7/2022 Singh et al.
2022/0227794 A1 7/2022 Matray et al.
2022/0305127 A1 9/2022 Thomas et al.
2022/0372297 A1 11/2022 Matray et al.
2022/0380603 A1 12/2022 Matray et al.
2022/0402963 A1 12/2022 Matray et al.
2023/0012304 A1 1/2023 Matray et al.
2023/0129481 A1 4/2023 Matray et al.
2024/0043455 A1 2/2024 Battrell et al.
2024/0092820 A1 3/2024 Matray et al.
2024/0132725 A1 4/2024 Sherif
2024/0207423 A1 6/2024 Matray
2024/0210408 A1 6/2024 Jackson et al.
2024/0248094 A1 7/2024 Matray et al.
2024/0255514 A1 8/2024 Matray et al.
2024/0287313 A1 8/2024 Sherif
2024/0287314 A1 8/2024 Matray et al.
2024/0327440 A1 10/2024 Jackson et al.

FOREIGN PATENT DOCUMENTS

CN 103319378 A 9/2013
CN 104072727 A 10/2014
CN 106589005 A 4/2017
CN 107106685 A 8/2017
CN 107709470 A 2/2018
CN 109153860 A 1/2019
EP 0708837 B1 3/2006
GB 2 372 256 A 8/2002
GB 2 554 666 A 4/2018
JP S61207395 A 9/1986
JP H4-282391 A 10/1992
JP 09124599 A * 5/1997
JP 2000-17183 A 1/2000
JP 2003532092 A 10/2003
JP 2011135823 A 7/2011
JP 2014527071 A 10/2014
JP 2016534107 A 11/2016
JP 2017504659 A 2/2017
JP 2017124994 A 7/2017
JP 2018507863 A 3/2018
JP 2018512167 A 5/2018
JP 2018515628 A 6/2018
JP 2019516807 A 6/2019
JP 2019516821 A 6/2019
JP 2021518410 A 8/2021
JP 7069033 B2 5/2022
KR 20030032939 A 4/2003
KR 101041446 B1 6/2011
KR 10-2015-0007795 A 1/2015
KR 20160022358 A 2/2016
KR 20180005650 A 1/2018
KR 10-2020-0133374 A 11/2020
KR 20210032434 A 3/2021
KR 102530707 B1 5/2023
SU 1121931 A1 4/1988
WO 95/02700 A1 1/1995
WO WO 9506731 A2 3/1995
WO WO 9832463 A2 7/1998
WO WO 0173123 A2 10/2001
WO 02/22883 A1 3/2002
WO WO 02083954 A1 10/2002
WO WO 2004007751 A2 1/2004
WO WO 2007094135 A1 8/2007
WO WO 2009113645 A1 9/2009
WO 2010/026957 A1 3/2010
WO WO 2011088193 A2 7/2011
WO 2013/012687 A2 1/2013
WO WO 2014102803 A1 7/2014
WO 2014/147642 A1 9/2014
WO WO 2015091953 A1 6/2015
WO WO 2015155753 A2 10/2015
WO 2016168750 A1 10/2016
WO WO-2016183185 A1 11/2016
WO WO 2017003639 A2 1/2017
WO WO 2017062271 A2 4/2017
WO WO 2017089890 A1 6/2017
WO WO 2017094897 A1 6/2017
WO 2017/173348 A1 10/2017
WO WO 2017173355 A1 10/2017
WO WO 2017177065 A2 10/2017
WO WO 2017197144 A1 11/2017
WO WO 2018045278 A1 3/2018
WO 2018/060722 A1 4/2018
WO WO 2019071208 A1 4/2019
WO WO 2019126691 A1 6/2019
WO WO 2019140227 A1 7/2019
WO WO 2019182765 A1 9/2019
WO WO 2019182766 A1 9/2019
WO WO 2020219959 A1 10/2020
WO 2021/067483 A1 4/2021
WO WO 2021062176 A2 4/2021

OTHER PUBLICATIONS

Machine translation of JP H09-124599A (Year: NA).*

Shaller et al (Chromophoric and Dendritic Phosphoramidites Enable Construction of Functional Dendrimers with Exceptional Brightness and Water Solubility, Chem. Eur. J. 2014, 20, 12165-12171). (Year: 2014).*

Bargh et al., “Cleavable linkers in antibody-drug conjugates,” *Chemical Society Reviews 48*(16):4361-4374, Aug. 21, 2019. (15 pages).-

(56) References Cited

OTHER PUBLICATIONS

Kolpashchikov, "Binary Probes for Nucleic Acid Analysis," *Chemical Reviews 110*(8):4709-4723, Jun. 28, 2010. (15 pages).
Kozytska et al., "Discovery of the novel, homogenous payload platform Dolasynthen for Antibody-Drug Conjugates," Mersana Therapeutics, Abstract #272, 2018. (1 page).
Lee et al., "The spectroscopic analysis for binding of amphipathic and antimicrobial model peptides containing pyrenylalanine and truptophan to lipid bilayer," *Biochimica et Biophysica Acta 984*:174-182, Sep. 4, 1989. (9 pages).
Liso et al., "Polymeric drugs derived from Ibuprofen with improved antiinflammatory profile," *Journal of Biomedical Materials Research 32*:553-560, Dec. 1996. (8 pages).
Liu et al., "Imidazole inhibits autophagy flux by blocking autophagic degradation and triggers apoptosis via increasing FoxO3a-Bim expression," *International Journal of Oncology 46*:721-731, Feb. 2015. (11 pages).
1vnitski et al., "Introducing charge transfer functionality into prebiotically relevant β-sheet peptide fibrils," *Chemical Communications 50*:6733-6736, May 12, 2014. (4 pages).
Marras et al., "Efficiencies of fluorescence resonance energy transfer and contact-mediated quenching in oligonucleotide probes," *Nucleic Acids Research 30*(21):e122, Nov. 1, 2002. (8 pages).
Pawelczyk et al., "Molecular Consortia—Various Structural and Synthetic Concepts for More Effective Therapeutics Synthesis," *International Journal of Molecular Sciences 19*:1104, Apr. 6, 2018. (19 pages).
Wang et al., "Novel dexamethasone-HPMA copolymer conjugate and its potential application in treatment of rheumatoid arthritis," *Arthritis Research & Therapy 9*(1):R2, Jan. 18, 2007. (9 pages).
Wang, "Modern Synthetic Methods and Technologies of Polymers," Common Knowledge Evidence, Tongji University Press, 1st Edition, Jul. 2013, pp. 210-211. (includes portion of Chinese Office Action with English Summary of relevance) (20 pages).
Xu et al., "Synthesis of [D-Pyrenylalanine4,4']gramicidin S by Solid-Phase-Synthesis and Cyclization-Cleavage Method with Oxime Resin," *Chemistry Letters 21*:191-194, Feb. 1992. (4 pages).
"What is an Analyte?," Google Search, dated Mar. 22, 2018, retrieved from https://www.google.com/search?q=what+is+an+analyte&rlz=1C1GCEB_enUS775US775&oq=what+is+an+analyte&aqs=chrome..69i57j015.3231j0j7&s. . . 2 pages.
Arian et al., "1,9-Dialkoxyanthracene as a $^1O_2$-Sensitive Linker," *J. Am. Chem. Soc. 133*:3972-3980, 2011.
Avirah et al., "Infrared Absorbing Croconaine Dyes: Synthesis and Metal Ion Binding Properties," *J. Org. Chem. 73*(1):274-279, 2008.
Babitskaya et al., "Bromoacyl Analogues of Phosphatidycholine with Intramolecular Fluorescence Quenching and Their Use as Substrates for Continuous Monitoring of Phospholipase $A_2$ Activity," *Applied Biochemistry and Microbiology 40*(4):351-356, 2004.
Beaucage et al., "The Functionalization of Oligonucleotides Via Phosphoramidite Derivatives," *Tetrahedron 49*(10):1925-1963, 1993.
Becker et al., "New Thermotropic Dyes Based on Amino-Substituted Perylendicarboximides," *Chem. Eur. J.* 6(21):3984-3990, 2000.
Bergstrom et al., "A NaPi2b Antibody-Drug Conjugate Induces Durable Complete Tumor Regressions in Patient-Derived Xenograft Models of NSCLC," *IASLC 17th World Conference on Lung Cancer*, Vienna, Austria, Dec. 4-7, 2016 (8 pages).
Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015.
Bergstrom et al., "Potent Promise," *Innovations in Pharmaceutical Technology 49*:16-20, 2014.
Bergstrom et al., "XMT-1522 induces tumor regressions in pre-clinical models representing HER2-positive and HER2 low-expressing breast cancer," Mersana Therapeutics, Abstract P4-14-28, 2015, 1 page.
Braeckmans et al., "Three-dimensional fluorescence recovery after photobleaching with the confocal scanning laser microscope," *Biophysical Journal 85*:2240-2252, 2003.
Braga et al., "Intracellular macromolecular mobility measured by fluorescence recovery after photobleaching with confocal laser scanning microscopes," *Molecular Biology of the Cell 15*:4749-4760, 2004.
Brinkley, "A brief survey of methods for preparing protein conjugates with dyes, haptens, and cross-linking reagents," *Bioconjugate Chem 3*:2-13, 1992.
CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications 40*(1):187-214, 1975. (1 page).
Chattopadhyay et al., "Brilliant Violet Fluorophores: A New Class of Ultrabright Fluorescent Compounds for Immunofluorescence Experiments," *Cytometry Part A 81A*:456-466, 2012.
Chong et al., "Oxygen Quenching of Pyrene-Lipid Fluorescence in Phosphatidylcholine Vesicles—A Probe for Membrane Organization," *Biophys. J.* 47:613-621, 1985.
Cuppoletti et al., "Oligomeric fluorescent labels for DNA," *Bioconjug. Chem.* 16(3):528-534, 2005.
Dai et al., "DNA-polyfluorophore excimers as sensitive reporters for esterases and lipases," *Chem. Commun.* 46:1221-1223, 2010.
Dioubankova et al., "Oligonucleotides containing new fluorescent 1-phenylethynylpyrene and 9,10-bis(phenylethynyl)anthracene uridine-2'-carbamates: synthesis and properties," *Tetrahedron 60*:4617-4626, 2004.
DiVittorio et al., "Synthetic peptides with selective affinity for apoptotic cells," *Org. Biomol. Chem.* 4:1966-1976, 2006.
Doi et al., "Hetero-Selective DNA-Like Duplex Stabilized by Donor-Acceptor Interactions," *Chem. Eur. J.* 21:15974-15980, 2015.
Dubrovsky, "Semiconductor nanoparticles as reporters in multiplexed immunoassay and cell analysis," *International Journal of Nanoscience 8*(1 & 2):163-167, 2009.
Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem 22*:1309-1319, 2011.
Gao et al., "Libraries of Composite Polyfluors Built from Fluorescent Deoxyribosides," *Journal of the American Chemical Society 124*:11590-11591, 2002.
Gao et al., "Modified DNA Analogues That Sense Light Exposure with Color Changes," *Journal of the American Chemical Society 126*:12748-12749, 2004.
Gordon et al., "Analysis of simulated and experimental fluorescence recovery after photobleaching. Data for two diffusing components," *Biophysical Journal 68*:766-778, 1995.
Hanhela et al., "Synthesis and Evaluation of Fluorescent Materials for Colour Control of Peroxyoxalate Chemiluminescence. III. Yellow and Red Fluorescent Emitters," *Australian Journal of Chemistry 34*:1701-1717, 1981.
Haraguchi, "Live Cell Imaging: Approaches for Studying Protein Dynamics in Living Cells," *Cell Structure And Function 27*:333-334, 2002.
Jain et al. "Current ADC Linker Chemistry," *Pharm. Res.* 32:3526-3540, 2015.
Johansson, "Choosing Reporter-Quencher Pairs for Efficient Quenching Through Formation of Intramolecular Dimers," *Methods in Molecular Biology 335*:17-29, 2006.
Koo et al., "Fluorescent DNA chemosensors: identification of bacterial species by their volatile metabolites," *Chemical Communications 47*:11435-11437, 2011.
Kozma et al., "Fluorescent Ligands for Adenosine Receptors," *Bioorganic & Medicinal Chemistry Letters 23*: 26-36, 2013.
Lee et al., "Monitoring the Hydrophobic Interactions of Internally Pyrene-Labeled Poly(ethylene oxide)s in Water by Fluorescence Spectroscopy," *Macromolecules 31*:9193-9200, 1998.
Leung et al., "7-Amino-4-Methyl-6-Sulfocoumarin-3-Acetic Acid: A Novel Blue Fluorescent Dye for Protein Labeling," *Bioorganic & Medicinal Chemistry Letters 9*: 2229-2232, 1999.
Li et al., "Polymeric Drugs: Advances in the development of pharmacologically active polymers," *Journal of Controlled Release 219*:369-382, 2015.

(56) References Cited

OTHER PUBLICATIONS

Li et al., "Responsive nanogel-based dual fluorescent sensors for temperature and $Hg^{2+}$ ions with enhanced detection sensitivity," *J. Mater. Chem.* 20:10716-10723, 2010.
Liu et al., "Detection of prostate-specific membrane antigen on HUVECs in response to breast tumor-conditioned medium," *International Journal of Oncology 38*:1349-1355, 2011.
Liu et al., "DNA-Based Micelles: Synthesis, Micellar Properties and Size-Dependent Cell Permeability," *Chem. Eur. J.* 16:3791-3797, 2010 (14 Pages).
Luo et al., "Sensitive and rapid quantification of C-reactive protein using quantum dot-labeled microplate immunoassay," *Journal of Translational Medicine 10*(24):1-9, 2012.
Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.
Masuko et al., "Fluorescence resonance energy transfer from pyrene to perylene labels for nucleic acid hybridization assays under homogenous solution conditions," *Nucleic Acids Research 28*(8):e34, 2000 (8 pages).
Mersana Therapeutics, URL=http://www.mersana.com, download date Jan. 3, 2019, 9 pages.
Molotkovsky et al., "Perylenoyl- and Anthrylvinyl-Labeled Lipids as Membrane Probes," *Biochimica et Biophysica Acta 778*:281-288, 1984.
Nussbaumer et al., "Amplification of Chirality by Supramolecular Polymerization of Pyrene Oligomers," *Angewandte Chemie International Edition 50*:5490-5494, 2011.
Paris et al., "Probing DNA sequences in solution with a monomer-excimer fluorescence color change," *Nucleic Acids Research 26*(16):3789-3793, 1998.
Petreus et al., "Polyester imides containing main-chain phosphorus," *Revue Roumaine de Chimie 34*(8):971-978, 1994 (with English Abstract).
Pownall et al., "Kinetics of Spontaneous and Plasma-Stimulated Sphingomyelin Transfer," *Biochimica et Biophysica Acta 712*:169-176, 1982.
PubChem, "US20100012929A1-20100121-C00010_4," SID No. 140452858, retrieved Mar. 29, 2016 from URL https://pubchem.ncbi.nlm.nih.gov/substance/140452858#sectio . . . , 6 pages.
Ren et al., "An Antisense Oligodeoxynucleotide-Doxorubicin Conjugate: Preparation and Its Reversal Multidrug Resistance of Human Carcinoma Cell Line In Vitro," *Nucleosides, Nucleotides & Nucleic Acids 23*(10):1595-1607, 2004.
RN 230952-79-1, Registry Database Compound, 1999.
Saito et al., "Dual-labeled oligonucleotide probe for sensing adenosine via FRET: A novel alternative to SNPs genotyping," *Chem. Commun.*:2133-2135, 2007.
Singh et al., "Multiplexed measurement of membrane protein populations," *Caplus 2003*:769075, 2003. (2 pages).
Stewart et al., "The Fluorescence of a Chelating Two-Photon-Absorbing Dye is Enhanced with the Addition of Transition Metal Ions but Quenched in the Presence of Acid," *Proc. Of SPIE 9939*(993904):1-10, 2016.
Stuart et al., "Site-Specific DNA-Doxorubicin Conjugates Display Enhanced Cytotoxicity to Breast Cancer Cells," *Bioconjugate Chemistry 25*:406-413, 2014.
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, 2002.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 2, 20105, 23 pages).
Tram et al., "Oligonucleotide Labeling Using BODIPY Phosphoramidite," *Nucleosides, Nucleotides & Nucleic Acids 30*(1):1-11, 2011.
Vinogradov et al., "Total synthesis and biochemical characterization of mirror image barnase," *Chem Sci. 6*: 2997-3002, 2015.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wilson et al., "Efficient Quenching of Oligomeric Fluorophores on a DNA Backbone," *Journal of the American Chemical Society 129*(50): 15426-15427, 2007.
Wilson et al., "Oligodeoxyfluorosides: Strong Sequence of Dependence of Fluorescence Emission," *Tetrahedron 63*(17):3427-3433, 2007 (18 Pages).
Yurkovetskiy et al., "Advantages of Polyacetal Polymer-based Antibody Drug Conjugates: Application to Low Expression Targets," Mersana Therapeutics, technical paper #2645, 2014, 1 page.
Zhang et al., "FRET Imaging of Enzyme-Responsive HPMA Copolymer Conjugate," *Macromolecular Bioscience 17*(1600125):1-8, 2017.
Aviñó et al., "Solid-phase synthesis of oligomers carrying several chromophore units linked by phosphodiester backbones," *Bioorganic & Medicinal Chemistry Letters 18*:2306-2310, 2008.
Bag et al., "Triazolyl-donor-acceptor chromophore-decorated unnatural amino acids and peptides: FRET events in a β-turn conformation," *Chem. Commun.* 50:433-435, 2014.
Boldyrev et al., "Synthesis and Characteristics of New Fluorescent Probes Based on Cardiolipin," *Russian Journal of Bioorganic Chemistry 35*(2):219-224, 2009.
Breul et al., "Fluorescent monomers as building blocks for dye labeled polymers: synthesis and application in energy conversion, biolabeling and sensors," Chem. Soc. Rev. 42(12):5366-5407, 2013.
Buckhout-White et al., "Assembling programmable FRET-based photonic networks using designer DNA scaffolds," *Nature Communications 5*:5615, Dec. 11, 2014. (16 pages).
CAPLUS Accession No. 1991:467753, Mielewczyk et al., "5' end fluorescent labelling of oligonucleotides with riboflavin-derived phosphitylating reagent," *Acta Biochimica Polonica 36*(3-4):225-233, 1989. (1 page).
CAPLUS Accession No. 1995:665426, Chen et al., "Synthesis of Novel Phosphoramidite Reagents for the Attachment of Antisense Oligonucleotides to Various Regions of the Benzophenanthridine Ring System," *Bioconjugate Chemistry 6*(4):473-482, Jul. 1, 1995. (1 page).
CAPLUS Accession No. 1995:733249, WO9506731A2, filed Mar. 9, 1995. (1 page).
CAPLUS Accession No. 1995:849926, Reed et al., "Structure-Activity Relationships of Cytotoxic Cholesterol-Modified DNA Duplexes," *Journal of Medicinal Chemistry 38*(22):4587-4596, Oct. 27, 1995. (1 page).
CAPLUS Accession No. 1997:497709, Puri et al., "Synthesis of 5'-polyarene-tethered oligo-DNAs and the thermal stability and spectroscopic properties of their duplexes and triplexes," *Tetrahedron 53*(30):10409-10432, Jul. 28, 1997. (1 page).
CAS Registry No. 862288-26-4, American Chemical Society, 2021. (1 page).
Chang et al., "A General Approach for Generating Fluorescent Probes to Visualize Piconewton Forces at the Cell Surface," *J. Am. Chem. Soc.* 138:2901-2904, 2016. (4 pages).
Chen et al., "Synthesis and properties of new segmented block poly(urethane-urea)s containing phosphatidylcholine analogues and polybutadienes," *Macro-Molecular Chemistry and Physics 197*(5):1587-1597, May 1996. (11 pages).
Chen et al., "Synthesis of Novel Phosphoramidite Reagents for the Attachment of Antisense Oligonucleotides to Various Regions of the Benzophenanthridine Ring System," *Bioconjugate Chemistry 6*(4):473-482, Jul. 1, 1995. (10 pages).
Ciccotelli et al., "Polyguanine-conjugated antigens for scavenger receptor targeting and self-adjuvanting vaccines (VAC13P.1125)," *The Journal of Immunology 194*(Suppl. 1):214.5, May 1, 2015 [Abstract]. (1 page).

(56) References Cited

OTHER PUBLICATIONS

Damian et al., "Synthesis and DNA Interaction of Platinum Complex/Peptide Chimera as Potential Drug Candidates," *Eur. J. Org. Chem.* 6161-6170, 2010.
De Vos et al., "New Non Nucleosidic Phosphoramidites for the Solid Phase Multi-Labelling of Oligonucleotides: Comb- and Multifork-Like Structures," *Nucleosides & Nucleotides 13*(10):2245-2265, 1994.
Drescher et al., "General Synthesis and Aggregation Behaviour of New Single-Chain Bolaphospholipids: Variations in Chain and Headgroup Structures," *Chemistry—A European Journal 14*(22):6796-6804, 2008.
Dropulic et al., "Update on New Antivirals Under Development for the Treatment of Double-Stranded DNA Virus Infections," Clinical Pharmacology & Therapeutics 88(5):610-619, Nov. 2010.
Finniss et al., "A versatile acid-labile linker for antibody-drug conjugates," Med. Chem, Commun; 5; Apr. 1, 2014, 4 pages.
Franzini et al., "Identification of Structure-Activity Relationships from Screening a Structurally Compact DNA-Encoded Chemical Library," *Angewandte Chemie International Edition 54*:3927-3931, Feb. 3, 2015 [with supporting information]. (41 pages).
Griesang et al., "Four-Color, Enzyme-Free Interrogation of DNA Sequences with Chemically Activated, 3'-Fluorphore-Labeled Nucleotides," *Angew. Chem. Int. Ed.* 45:6144-6148, 2006.
Gupta et al., "Dendrimers: Novel Polymeric Nanoarchitectures for Solubility Enhancement," *Biomacromolecules 7*(3):649-658, Mar. 2006 [Published online Feb. 15, 2006]. (10 pages).
Guryev et al., "Control of the Fluorescence of Dye-Antibody Conjugates by (2-Hydroxypropyl)-β-cyclodextrin in Fluorescence Microscopy and Flow Cytometry," *Analytical Chemistry 83*:7109-7114, Aug. 16, 2011.
Hasegawa et al., "Cysteine, histidine and glycine exhibit anti-inflammatory effects in human coronary arterial endothelial cells," *Clinical and Experimental Immunology 167*:269-274, Jan. 11, 2012. (6 pages).
Irani et al., "Molecular properties of human IgG subclasses and their implications for designing therapeutic monoclonal antibodies against infectious diseases," *Molecular Immunology 67*:171-182, 2015.
Kashida et al., "A Cationic Dye Triplet as a Unique "Glue" That Can Connect Fully Matched Termini of DNA Duplexes," *Chem. Eur. J.* 17:2614-2622, 2011.
Khandare et al., "Polymer-drug conjugates: Progress in polymeric prodrugs," *Progress in Polymer Science 31*(4):359-397, Apr. 2006. (39 pages).
Krueger at al., "Fluorescent Amino Acids: Modular Building Blocks for the Assembly of New Tools for Chemical Biology," *ChemBioChem 14*:788-799, 2013.
Lapeyre et al., "Aryldithioethyloxycarbonyl (Ardec): A New Family of Amine Protecting Groups Removable under Mild Reducing Conditions and Their Applications to Peptide Synthesis," *Chem. Eur. J.* 12:3655-3671, 2006.
Lewis et al., "Orientation Control of Fluorescence Resonance Energy Transfer Using DNA as a Helical Scaffold," *J. Am. Chem. Soc.* 127(28):10002-10003, 2005.
Liu et al., "Increased Cytotoxicity and Decreased In Vivo Toxicity of FdUMP[10] Relative to 5-FU," *Nucleosides & Nucleotides 18*(8):1789-1802, Aug. 1999. (14 pages).
Liu et al., "Structure-based programming of lymph-node targeting in molecular vaccines," *Nature 507*:519-522, Mar. 27, 2014 [Published online Feb. 16, 2014]. (15 pages).
McKinlay et al., "Cell-Penetrating, Guanidinium-Rich Oligophosphoesters: Effective and Versatile Molecular Transporters for Drug and Probe Delivery," *J. Am. Chem. Soc.* 138:3510-3517, Feb. 22, 2016.
Midoux et al., "Chemical vectors for gene delivery: a current review on polymers, peptides and lipids containing histidine or imidazole as nucleic acids carriers," *British Journal of Pharmacology 157*:166-178, May 2009. (13 pages).
Mielewczyk et al., "5' end fluorescent labelling of oligonucleotides with riboflavin-derived phosphitylating reagent," *Acta Biochimica Polonica 36*(3-4):225-233, 1989. (9 pages).
Moss, "Nomenclature of Fused and Bridged Fused Ring Systems," *Pure & Appl. Chem.* 70(1):143-216, 1998.
Mthembu et al., "Breaking a Couple: Disulfide Reducing Agents," *ChemBioChem 21*, 2020. (10 pages).
Nolting, "Linker Technology for Antibody-Drug Conjugates," in Ducry (ed.), *Antibody-Drug Conjugates,* Humana Press, Totowa, NJ, 2013, Ch. 5, pp. 71-100.
Oh et al., "Low-dose guanidine and pyridostigmine: relatively safe and effective long-term symptomatic therapy in Lambert-Eaton myasthenic syndrome," *Muscle & Nerve 20*:1146-1152, Sep. 1997. (7 pages).
Pelegrin et al., "Antiviral Monoclonal Antibodies: Can They Be More Than Simple Neutralizing Agents?" *Trends in Microbiology 23*(10):653-665, Oct. 2015.
Petersen et al., "Acyclic, achiral enamide nucleoside analogues. The importance of the C═C bond in the analogue for its ability to mimic natural nucleosides," *Organic & Biomolecular Chemistry 1*:3293-3296, Sep. 4, 2003. (4 pages).
Phares et al., "Improving the Stability and Sensing of Electrochemical Biosensors by Employing Trithiol-Anchoring Groups in a Six-Carbon Self-Assembled Monolayer," *Anal. Chem. 81*(3):1095-1100, Feb. 1, 2009.
Poupart et al., "Aminopropargyl derivative of terpyridine-bis(methylenamine) tetraacetic acid chelate of europium (Eu (TMT)-AP3): a new reagent for fluorescent labelling of proteins and peptides," Org. Biomol. Chem. 4:4165-4177, Oct. 2006.
Puri et al., "Synthesis of 5'-polyarene-tethered oligo-DNAs and the thermal stability and spectroscopic properties of their duplexes and triplexes," *Tetrahedron 53*(30):10409-10432, Jul. 28, 1997. (24 pages).
Reed et al., "Structure-Activity Relationships of Cytotoxic Cholesterol-Modified DNA Duplexes," *Journal of Medicinal Chemistry 38*(22):4587-4596, Oct. 27, 1995. (10 pages).
Rochat et al., "Water-Soluble Cationic Conjugated Polymers: Response to Electron-Rich Bioanalytes," *J. Am. Chem. Soc.* 135:17703-17706, 2013.
Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.
Samal et al., "Cationic polymers and their therapeutic potential," *Chemical Society Reviews 41*:7147-7194, Aug. 2012. (48 pages).
Shuey et al., "Cyclohexanediol Bisphosphates as Models for Phospholipid-Metal Ion Binding Sites," *Bioorganic Chemistry 21*:95-108, Mar. 1993. (14 pages).
Shuman et al., "Bacterial DNA repair by non-homologous end joining," *Nature Reviews Microbiology 5*:852-861, Nov. 2007.
STIC Search Report from American Chemical Society, for U.S. Appl. No. 17/255,353, dated Sep. 7, 2023. (143 pages).
Striebel et al., "Enhancing sensitivity of human herpes virus diagnosis with DNA microarrays using dendrimers," *Experimental and Molecular Pathology 77*:89-97, Oct. 2004 [Published online Jul. 15, 2004]. (9 pages).
Sun et al., "Dual-Color Fluorescence Imaging of Magnetic Nanoparticles in Live Cancer Cells Using Conjugated Polymer Probes," *Scientific Reports 6*:22368, 2016. (12 pages).
Sun et al., "High yield production of high molecular weight poly-(ethylene glycol)/ α-cyclodextrin polyrotaxanes by aqueous one-pot approach," *Polymer 53*:2884-2889, 2012.
Sun et al., "Self-assembled biodegradable micellar nanoparticles of amphiphilic and cationic block copolymer for siRNA delivery," *Biomaterials 29*:4348-4355, available online Aug. 2008. (8 pages).
Sun et al., "Ultrabright and Multicolorful Fluorescence of Amphiphilic Polyethyleneimine Polymer Dots for Efficiently Combined Imaging and Therapy," *Scientific Reports 3*:3036, 2013. (6 pages).
Tabujew et al., "Chapter One: Functionalization of Cationic Polymers for Drug Delivery Applications," *RSC Polymer Chemistry Series 13*, 2015. (29 pages).

(56) References Cited

OTHER PUBLICATIONS

Teyssot et al., "Aromatic Nitrogen Donors for Efficient Copper(1)-NHC CuAAC under Reductant-Free Conditions," Eur. J. Org. Chem. 3507-3515, 2010.
Vybornyi et al., "Formation of Two-Dimensional Supramolecular Polymers by Amphiphilic Pyrene Oligomers," *Angew. Chem. Int. Ed.* 52:114488-11493, 2013.
Wang et al., Fluorescence-Based Evaluation of the Partitioning of Lipids and Lipidated Peptides into Liquid-Ordered Lipid Microdomains: A Model for Molecular Partitioning into "Lipid Rafts," *Biophysical Journal 79*:919-933, Aug. 2000.
Winiger et al., "Long-Distance Electronic Energy Transfer in Light-Harvesting Supramolecular Polymers,"*Angew. Chem. Int. Ed.* 53:13609-13613, 2014.
Wu Yi et al., "$^{Py}$A-Modified Oligodeoxyadenylates: Expanded Fluorescence Phenomena and Structural Formation," *Chemistry—An Asian Journal 7*:60-63, Nov. 2011. (4 pages).
Yu et al., "Targeted Delivery of an Anti-Inflammatory PDE4 Inhibitor to Immune Cells via an Antibody-drug Conjugate," Molecular Therapy 24(12):2078-2089, Dec. 2016.
Zhao et al., "Mussel-Inspired One-Pot Synthesis of a Fluorescent and Water-Soluble Polydopamine-Polyethyleneimine Copolymer," Macromol. Rapid Commun. 36:909-915, 2015.
Neidle et al. (Eds.), "Chapter 7: Acridine-based Anticancer Drugs," Molecular Aspects of Anticancer Drug-DNA Interactions, Topics in Molecule in Structural Biology, vol. 2, pp. 270-311, 1994. (52 pages).
Wagenknecht, "Fluorescent DNA Base Modifications and Substitutes: Multiple Fluorophore Labeling and the DETEQ Concept," Annals of the New York Academy of Sciences 1130(1):122-130, May 2008. (9 pages).

* cited by examiner

POLYMERIC DYES HAVING A BACKBONE COMPRISING ORGANOPHOSPHATE UNITS

BACKGROUND

Technical Field

The present invention is generally directed to polymeric fluorescent or colored dyes, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for dyes having an increased molar brightness. Ideally, such dyes and biomarkers should be intensely colored or fluorescent and should be available in a variety of colors and fluorescent wavelengths. The present invention fulfills this need and provides further related advantages.

BRIEF SUMMARY

In brief, embodiments of the present invention are generally directed to compounds useful as water soluble, fluorescent and/or colored dyes and/or probes that enable visual detection of analyte molecules, such as biomolecules, as well as reagents for their preparation. Methods for visually detecting analyte molecules using the dyes are also described.

Embodiments of the presently disclosed dyes include two or more fluorescent and/or colored moieties covalently linked by linkers (e.g., $L^{1a}$, $L^{1b}$, $L^2$, $L^3$, $L^4$, $L^5$, $L^6$ and $L^7$). In contrast to previous reports of dimeric and/or polymeric dyes, the present dyes are significantly brighter than the corresponding monomeric dye compound. While, not wishing to be bound by theory, it is believed that the linker moiety provides sufficient spatial separation between the fluorescent and/or colored moieties such that intramolecular fluorescence quenching is reduced and/or eliminated.

The water soluble, fluorescent or colored dyes of embodiments of the invention are intensely colored and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In one embodiment, compounds having the following structure (I) are provided:

(I)

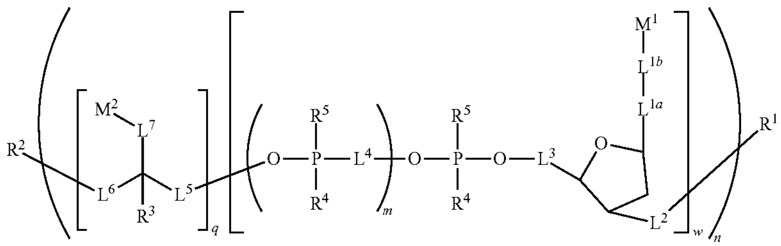

or a stereoisomer, tautomer or salt thereof, wherein $R^1$, $R^2$, $R^3$, $R^4$, $R^5$, $L^{1a}$, $L^{1b}$, $L^2$, $L^3$, $L^4$, $L^5$, $L^6$, $L^7$, $M^1$, $M^2$, q, w, m and n are as defined herein. Compounds of structure (I) find utility in a number of applications, including use as fluorescent and/or colored dyes in various analytical methods.

In another embodiment, a method for staining a sample is provided, the method comprises adding to said sample a compound of structure (I) in an amount sufficient to produce an optical response when said sample is illuminated at an appropriate wavelength.

In still other embodiments, the present disclosure provides a method for visually detecting an analyte molecule, comprising:

(a) providing a compound of structure (I); and (b) detecting the compound by its visible properties.

Other disclosed methods include a method for visually detecting a biomolecule, the method comprising:

(a) admixing a compound of structure (I) with one or more biomolecules; and (b) detecting the compound by its visible properties.

Other embodiments provide a method for visually detecting an analyte, the method comprising:

(a) providing a compound as disclosed herein, wherein $R^1$ or $R^2$ comprises a linker comprising a covalent bond to a targeting moiety having specificity for the analyte;

(b) admixing the compound and the analyte, thereby associating the targeting moiety and the analyte; and (c) detecting the compound by its visible properties.

Other embodiments are directed to a composition comprising a compound of structure (I) and one or more analyte molecule, such as a biomolecule. Use of such compositions in analytical methods for detection of the one or more biomolecules is also provided.

These and other aspects of the invention will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
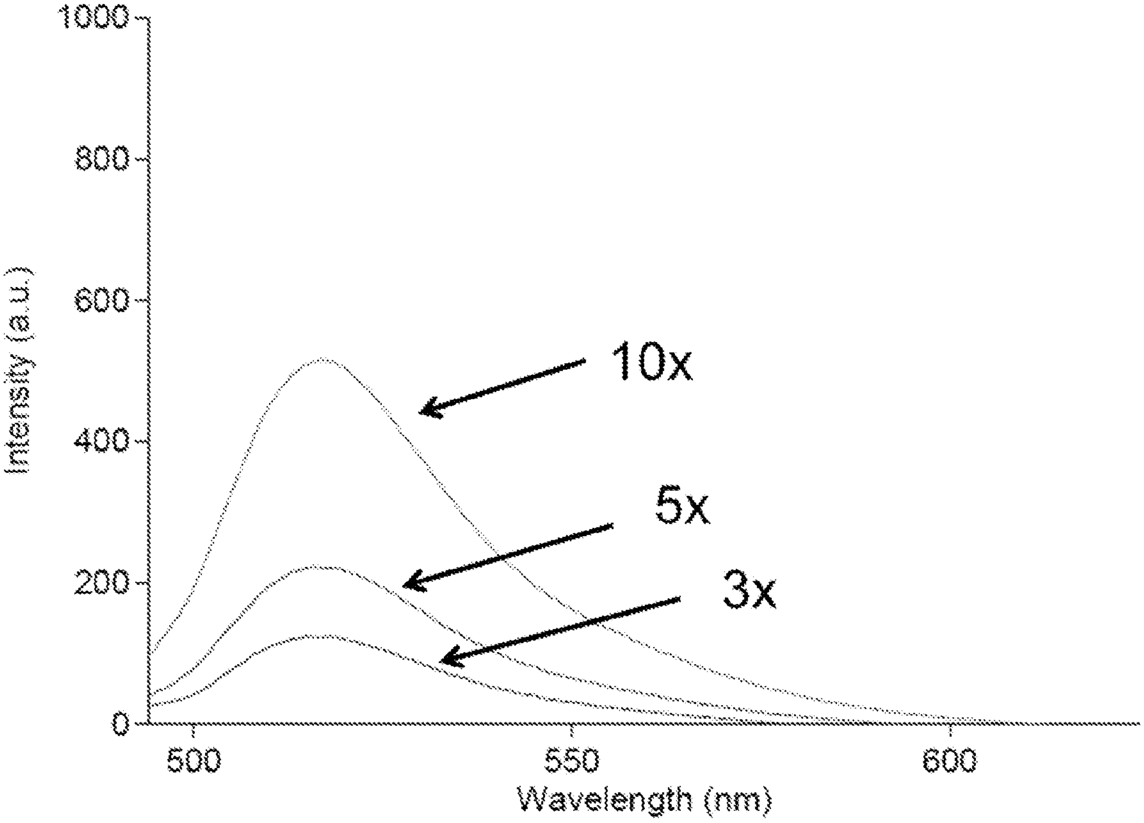
FIG. 1 shows fluorescence intensity for an polymer compound comprising Alexa Fluor 488 moieties (3×, 5× and 10×, respectively).
Figure 2A:
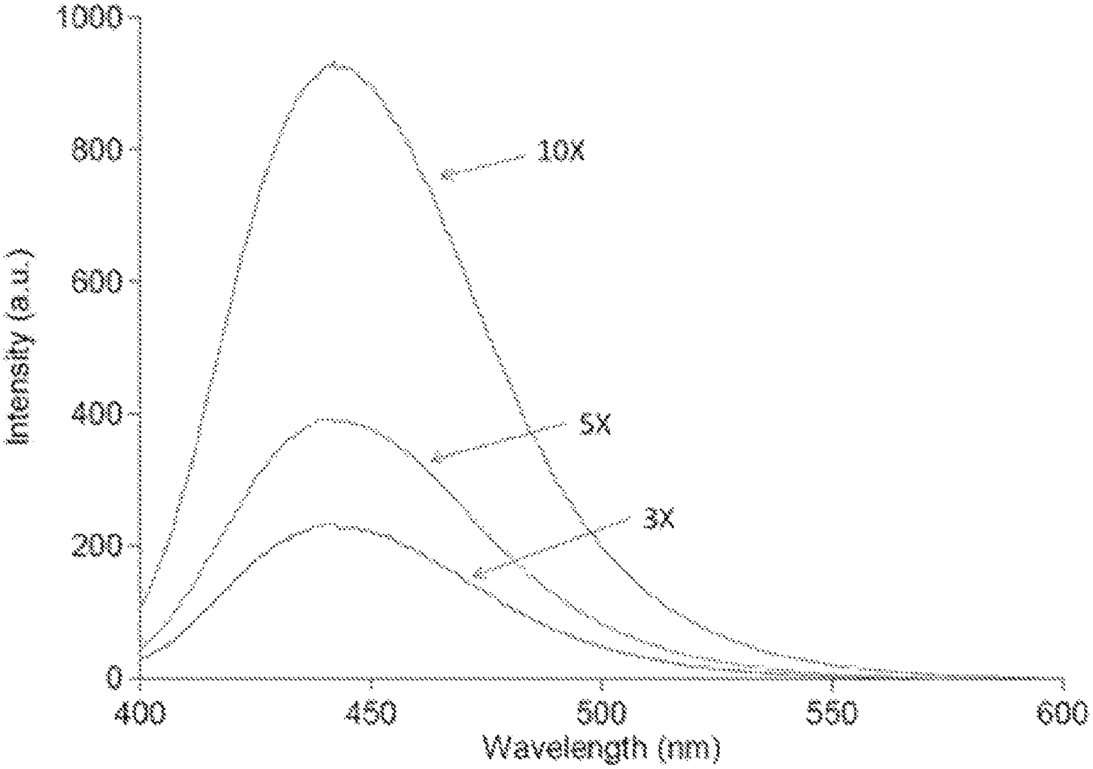
FIGS. 2A-B show spectral intensity and a PAGE readout for Alexa Fluor 350 moieties (3×, 5× and 10×, respectively).
Figure 2B:
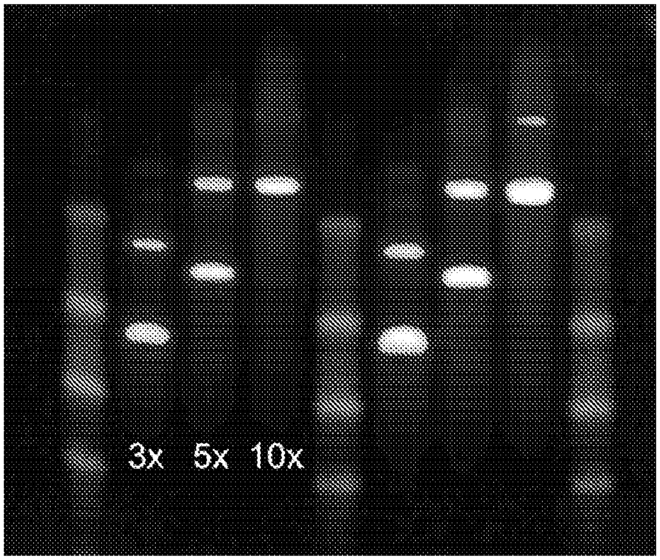
Figure 3A:
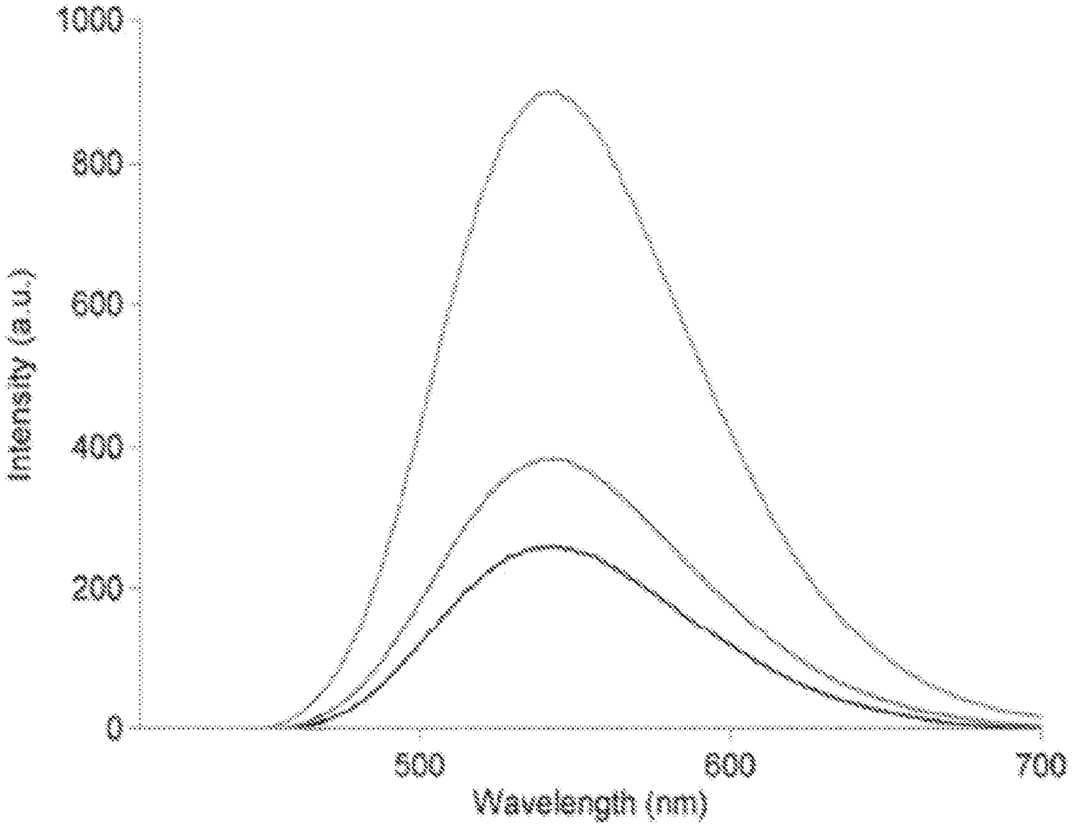
FIGS. 3 A-B depict spectral intensity and a PAGE readout for Pacific Orange moieties (3×, 5× and 10×, respectively); the PAGE readout provides a comparison to fluorescein.
Figure 3B:
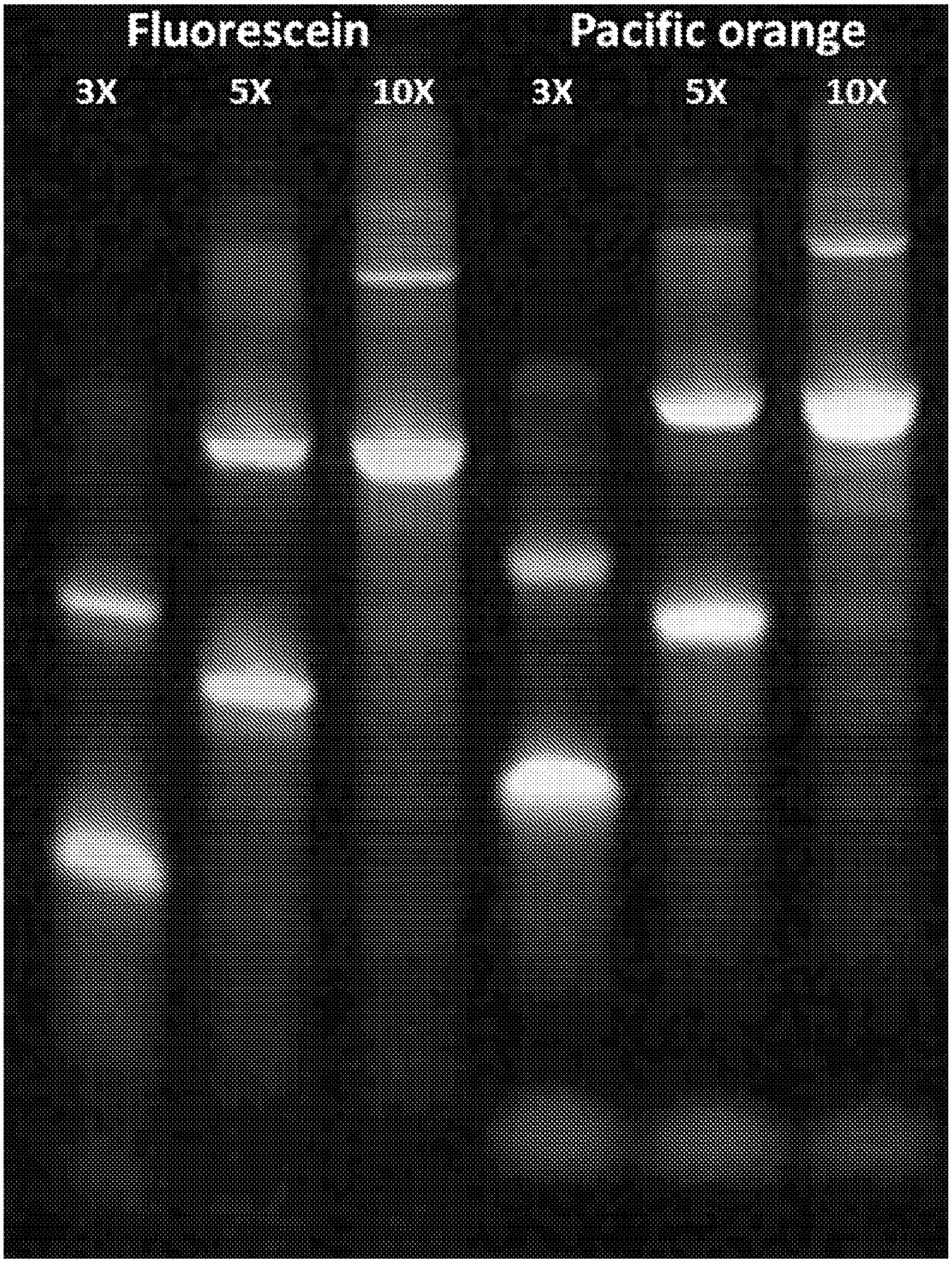
Figure 4:
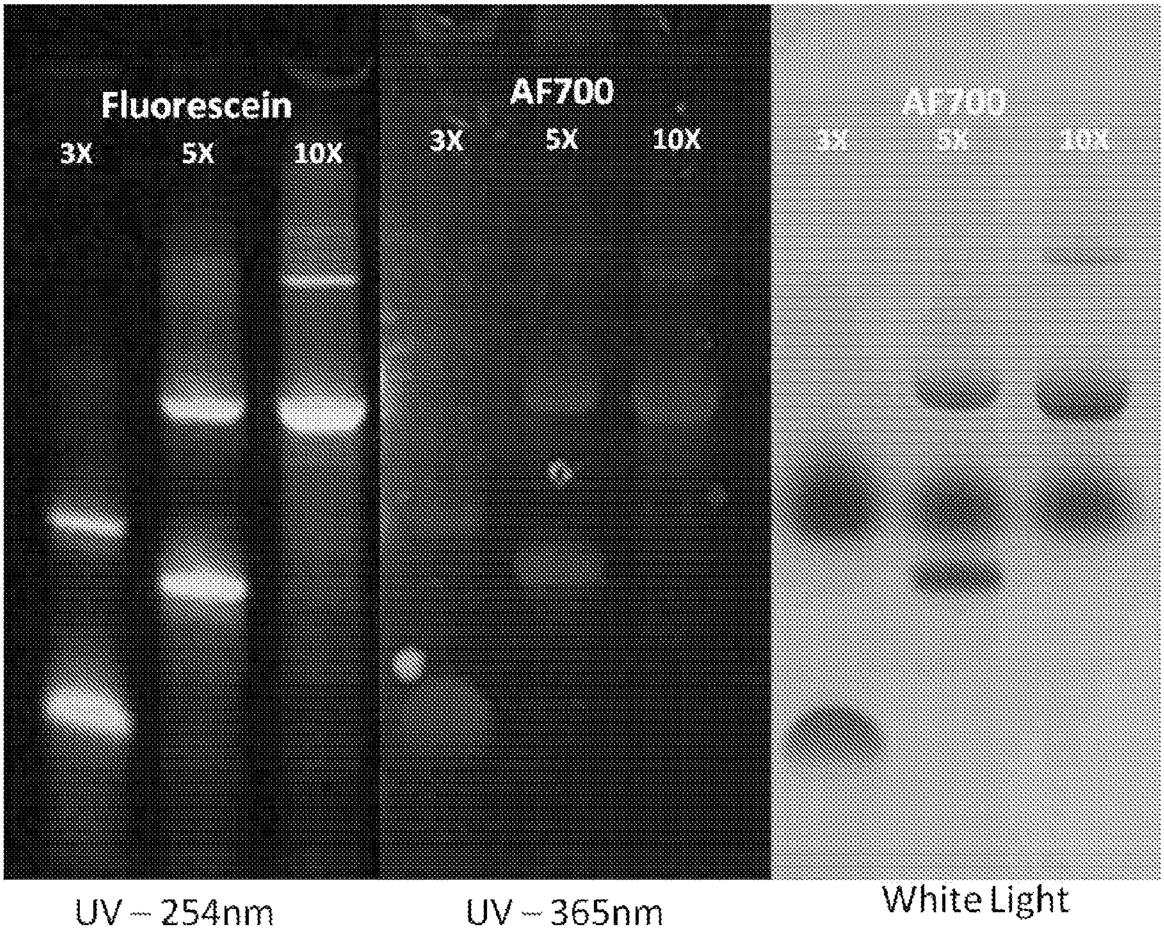
FIG. 4 illustrates a comparison between polymer compounds comprising fluorescein and Alexa Fluor 700 (each at 3×, 5× and 10×) using 254 nm, 365 nm and white light, respectively.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the $—NH_2$ group.

"Carboxy" refers to the $—CO_2H$ group.

"Cyano" refers to the —CN group.

"Formyl" refers to the —C(=O)H group.

"Hydroxy" or "hydroxyl" refers to the —OH group.

"Imino" refers to the =NH group.

"Nitro" refers to the —$NO_2$ group.

"Oxo" refers to the =O group.

"Sulfhydryl" refers to the —SH group.

"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen-carbon bond. The carbon-oxygen-carbon bond may be on the terminal end (as in an alkoxy group) or the carbon oxygen bond may be internal (i.e., C—O—C). Alkylethers include at least one carbon-oxygen-carbon bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —$OR_a$ where $R_a$ is an alkyl group as defined above containing one to twelve carbon atoms. Unless stated otherwise specifically in the specification, an alkoxy group is optionally substituted.

"Alkoxyalkylether" refers to a group of the formula —$OR_aR_b$ where $R_a$ is an alkylene group as defined above containing one to twelve carbon atoms, and $R_b$ is an alkylether group as defined herein. Unless stated otherwise specifically in the specification, an alkoxyalkylether group is optionally substituted, for example substituted with an alcohol or —OP(=$R_a$)($R_b$)$R_c$, wherein each of $R_a$, $R_b$ and $R_c$ is as defined for compounds of structure (I).

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —$OR_a$ where $R_a$ is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., Si, N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C," "HEG," and "PEG 1K" linking groups illustrated below:

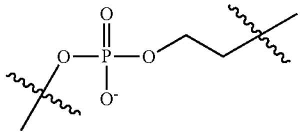

"C linker"

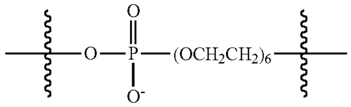

"HEG linker"

-continued

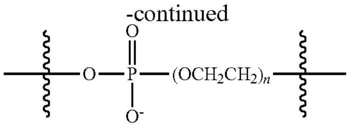

n = 11-28

"PEG 1K linker"

Multimers of the above C-linker, HEG linker and/or PEG 1K linker are included in various embodiments of heteroalkylene linkers. In some embodiments of the PEG 1K linker, n ranges from 19-25, for example n is 19, 20, 21, 22, 23, 24, or 25. Multimers may comprise, for example, the following structure:

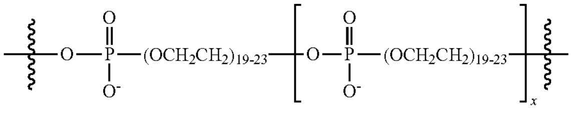

wherein x is 0 or an integer greater than 0, for example, x ranges from 0-100 (e.g., 1, 2, 3, 4, 5, 6, 7, 8, 9 or 10).

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O—)(=O)O— or —OP(O—)(=O)O— and multimers and combinations thereof.

"Phosphate" refers to the —OP(=O)($R_a$)$R_b$ group, wherein $R_a$ is OH, O— or $OR_c$; and $R_b$ is OH, O—, $OR_c$, a thiophosphate group or a further phosphate group, wherein $R_c$ is a counter ion (e.g., $Na^+$ and the like).

"Phosphoalkyl" refers to the —OP(=O)($R_a$)$R_b$ group, wherein $R_a$ is OH, O— or $OR_c$; and $R_b$ is —Oalkyl, wherein $R^c$ is a counter ion (e.g., $Na^+$ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined for compounds of structure (I).

"Phosphoalkylether" refers to the —OP(=O)($R_a$)$R_b$ group, wherein $R_a$ is OH, O— or $OR_c$; and $R_b$ is —Oalkylether, wherein $R_c$ is a counter ion (e.g., $Na^+$ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined for compounds of structure (I).

"Thiophosphate" refers to the —OP(=$R_a$)($R_b$)$R_c$ group, wherein $R_a$ is O or S, $R_b$ is OH, O—, S—, $OR_d$ or $SR_d$; and $R_c$ is OH, SH, O—, S—, $OR_d$, $SR_d$, a phosphate group or a further thiophosphate group, wherein $R_d$ is a counter ion (e.g., $Na^+$ and the like) and provided that: i) $R_a$ is S; ii) $R_b$ is S— or $SR_d$; iii) $R_c$ is SH, S— or $SR_d$; or iv) a combination of i), ii) and/or iii).

"Thiophosphoalkyl" refers to the —OP(=$R_a$)($R_b$)$R_c$ group, wherein $R_a$ is O or S, $R_b$ is OH, O—, S—, $OR_d$ or $SR_d$; and $R_c$ is —Oalkyl, wherein $R_d$ is a counter ion (e.g., $Na^+$ and the like) and provided that: i) $R_a$ is S; ii) $R_b$ is S— or $SR_d$; or iii) $R_a$ is S and $R_b$ is S— or $SR_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined for compounds of structure (I).

"Thiophosphoalkylether" refers to the —OP(=$R_a$)($R_b$)$R_c$ group, wherein $R_a$ is O or S, $R_b$ is OH, O—, S—, $OR_d$ or $SR_d$; and $R_c$ is —Oalkylether, wherein $R_d$ is a counter ion (e.g., $Na^+$ and the like) and provided that: i) $R_a$ is S; ii) $R_b$ is S— or $SR_d$; or iii) $R_a$ is S and $R_b$ is S— or $SR_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=$R_a$)($R_b$)$R_c$, wherein each of $R_a$, $R_b$ and $R_c$ is as defined for compounds of structure (I).

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

The suffix "-ene" refers to a particular structural feature (e.g., alkyl, aryl, heteroalkyl, heteroaryl) attached to the rest of the molecule through a single bond and attached to a radical group through a single bond. In other words, the suffix "-ene" refers to a linker having the structural features of the moiety to which it is attached. The points of attachment of the "-ene" chain to the rest of the molecule and to the radical group can be through one atom of or any two atoms within the chain. For example, a heteroarylene refers to a linker comprising a heteroaryl moiety as defined herein.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1,3-butadiene has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. In some embodiments of the disclosure, exemplary conjugates (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, $\alpha,\beta$-unsaturated carbonyl, alkene, maleimide, $\alpha$-haloimide, epoxide, aziridine, tetrazine, tetrazole, phosphine, biotin, thiirane and the like.

"Bio-conjugation" or "bio-conjugate" and related variations refer to a chemical reaction strategy for forming a stable covalent bond between two molecules. The term "bio-conjugation" is generally used when one of the molecules is a biomolecule (e.g., an antibody), but can be used to describe forming a covalent bond with a non-biomolecule (e.g., a polymeric resin). The product or compound resulting from such a reaction strategy is a "conjugate," "bio-conjugate" or a grammatical equivalent.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 $M^{-1}$ $cm^{-1}$. The compounds of the invention may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of this disclosure, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Non-limiting examples of photostable visible dyes suitable for use in the compounds and methods of the invention include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the invention are useful for a wide variety of analytical applications, such as biochemical and biomedical applications, in which there is a need to determine the presence, location, or quantity of a particular analyte (e.g., biomolecule). In another aspect, therefore, the invention provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the invention, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" or "solid support residue" refers to any solid substrate known in the art for solid-phase support of molecules, for example a "microparticle" refers to any of a number of small particles useful for attachment to compounds of the invention, including, but not limited to, glass beads, magnetic beads, polymeric beads, non-polymeric beads, and the like. In certain embodiments, a microparticle comprises polystyrene beads.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments disclosed herein are also meant to encompass all compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively.

Isotopically-labeled compounds of structure (I) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present invention include all solvates of the described compounds. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compounds of the invention may be true solvates, while in other cases the compounds of the invention may merely retain adventitious water or another solvent or be a mixture of water plus some adventitious solvent.

Embodiments of the compounds of the disclosure (e.g., compounds of structure I), or their salts, tautomers or solvates may contain one or more stereocenters and may thus give rise to enantiomers, diastereomers, and other stereoisomeric forms that may be defined, in terms of absolute stereochemistry, as (R)- or (S)- or, as (D)- or (L)- for amino acids. Embodiments of the present invention are meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present invention includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

Compounds

As noted above, in one embodiment of the present invention, compounds useful as fluorescent and/or colored dyes in various analytical methods are provided. In other embodiments, compounds useful as synthetic intermediates for preparation of compounds useful as fluorescent and/or colored dyes are provided. In general terms, embodiments of the present invention are directed to dimers and higher polymers of fluorescent and/or colored moieties. The fluorescent and or colored moieties are linked by a linking moiety. Without wishing to be bound by theory, it is believed the linker helps to maintain sufficient spatial distance between the fluorescent and/or colored moieties such that intramolecular quenching is reduced or eliminated, thus resulting in a dye compound having a high molar "brightness" (e.g., high fluorescence emission).

Accordingly, in some embodiments the compounds have the following structure (A):

(A)

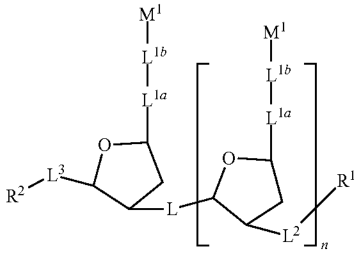

wherein L is a linker (e.g., heteroalkylene) sufficient to maintain spatial separation between one or more (e.g., each) $M^1$ group so that intramolecular quenching is reduced or eliminated, and $R^1$, $R^2$, $L^{1a}$, $L^{1b}$, $L^2$, $L^3$, $M^1$ and n are as defined for structure (I). In some embodiments of structure (A), L is a linker comprising one or more ethylene glycol or polyethylene glycol moieties.

In different embodiments the compounds have the following structure (B):

(B)

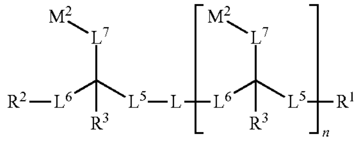

wherein L is a linker (e.g., heteroalkylene) sufficient to maintain spatial separation between one or more (e.g., each) $M^2$ group so that intramolecular quenching is reduced or eliminated, and $R^1$, $R^2$, $R^3$, $L^5$, $L^6$, $L^7$, $L^3$, $M^2$ and n are as defined for structure (I). In some embodiments of structure (B), L is a linker comprising one or more ethylene glycol or polyethylene glycol moieties.

In other embodiments is provided a compound having the following structure (I):

(I)

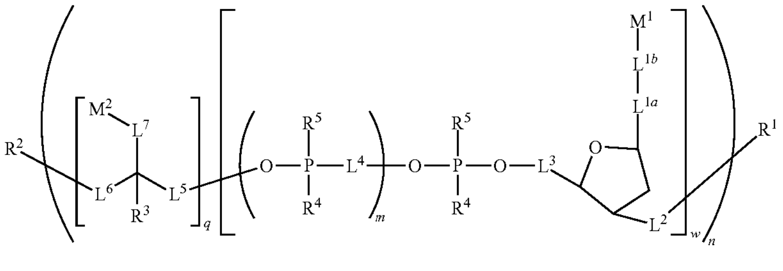

or a stereoisomer, salt or tautomer thereof, wherein:

$M^1$ and $M^2$ are, at each occurrence, independently a fluorescent or colored moiety comprising two or more double bonds and at least one degree of conjugation;

$L^{1a}$ is, at each occurrence, independently a heteroalkylene or heteroarylene linker;

$L^{1b}$, $L^2$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^1$ and $R^2$ are each independently H, OH, SH, alkyl, alkoxy, alkylether, heteroalkyl, —OP(=$R_a$)($R_b$)$R_c$, Q, or a protected form thereof, or L';

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, an integer of one or greater;

n is an integer of one or greater;

q and w are, at each occurrence, independently 0 or 1 provided that q and w are not both 0 at each occurrence; and at least one occurrence of $M^1$ or $M^2$ have one of the following structures:

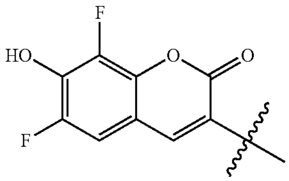
;

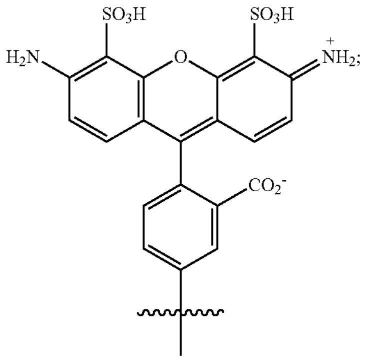

-continued

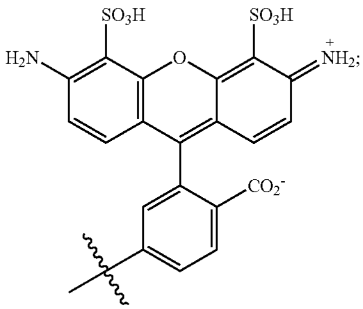

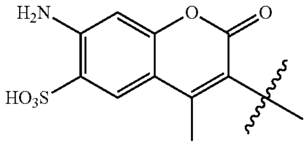
;

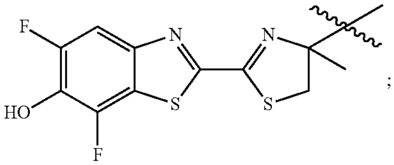
;

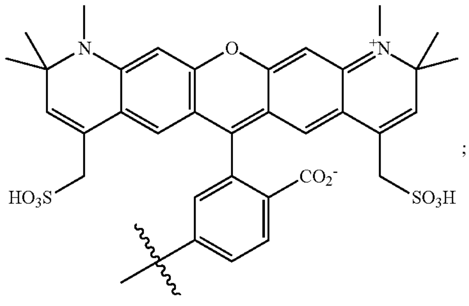
;

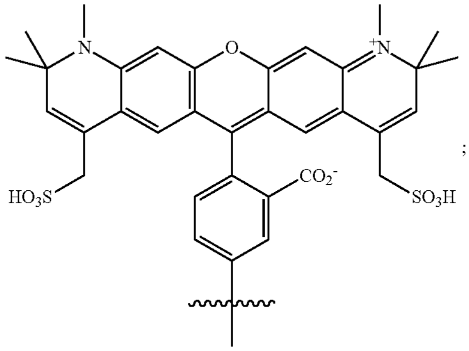
;

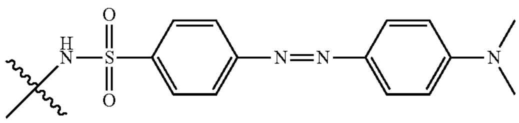
;

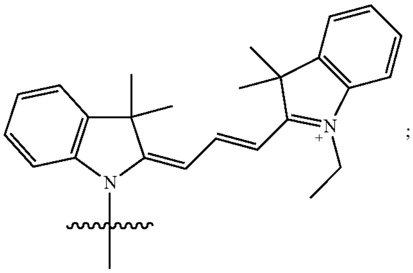
;

-continued

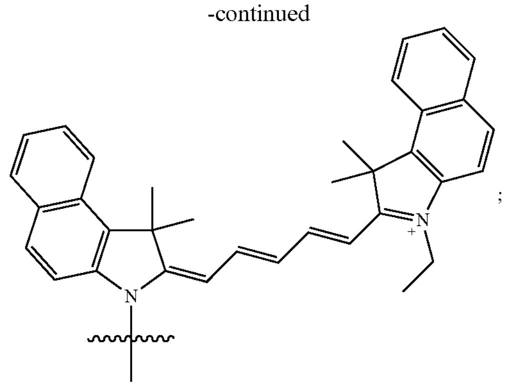

;

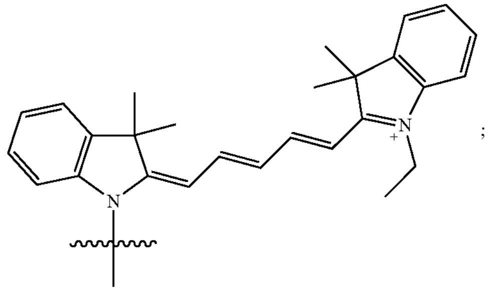

;

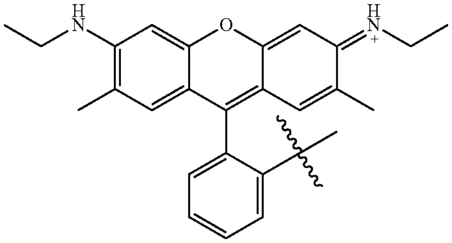

;

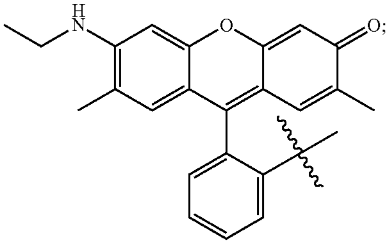

;

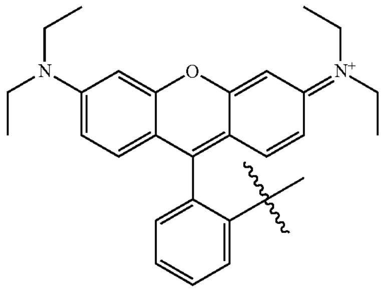

;

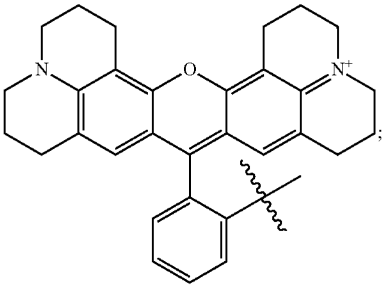

;

-continued

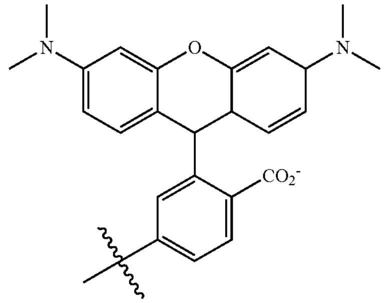

; or

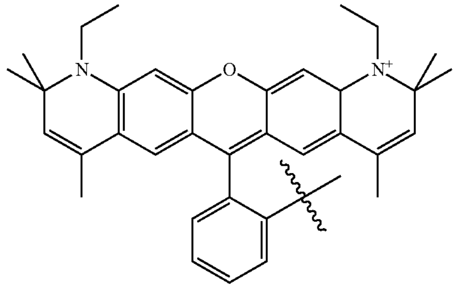

.

The various linkers and substituents (e.g., $M^1$, $M^2$, Q, $R^1$, $R^2$, $R^3$, $R_c$, $L^{1a}$, $L^{1b}$, $L^2$, $L^3$, $L^4$, $L^5$, $L^6$ and $L^7$) in the compound of structure (I) are optionally substituted with one more substituent. For example, in some embodiments the optional substituent is selected to optimize the water solubility or other property of the compound of structure (I). In certain embodiments, each chromophore, alkyl, alkoxy, alkylether, heteroarylene, heteroalkyl, alkylene, alkenylene, alkynylene, heteroalkylene, heteroalkenylene, heteroalkynylene, alkoxyalkylether, phosphoalkyl, thiophosphoalkyl, phosphoalkylether and thiophosphoalkylether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments the optional substituent is —OP(═Ra)(Rb)Rc, where Ra, Rb and Rc are as defined for the compound of structure (I).

In some embodiments, at least one occurrence of $L^{1a}$ is an optionally substituted 5-7 membered heteroarylene linker. In some more specific embodiments, $L^{1a}$ is, at each occurrence independently an optionally substituted 5-7 membered heteroarylene linker. In some embodiments, $L^{1a}$ is a 6-membered heteroarylene. In some embodiments, $L^{1a}$ comprises two N atoms and two O atoms. In certain embodiments, $L^{1a}$ is, at each occurrence, substituted. In some related embodiments, $L^{1b}$ is substituted, for example, $L^{1b}$ is substituted with oxo, alkyl (e.g., methyl, ethyl, etc.) or combinations thereof. In more specific embodiments, $L^{1a}$ is, at each occurrence, substituted with at least one oxo. In some embodiments, $L^{1a}$ has one of the following structures:

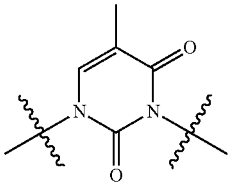

or

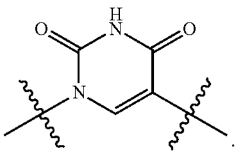

.

In some embodiments, $L^{1b}$ is, at each occurrence, independently an optional alkylene, alkenylene, alkynylene, heteroalkylene, heteroalkenylene, heteroalkynylene, alkyleneheteroarylenealkylene, alkyleneheterocyclylenealkylene, alkylenecarbocyclylenealkylene, heteroalkyleneheteroarylenealkylene, heteroalkyleneheterocyclylenealk lene, heteroalkylenecarbocyclylenealkylene, heteroalkyleneheteroaryleneheteroalkylene, heteroalkyleneheterocyclyleneheteroalkylene, heteroalkylenecarbocyclyleneheteroalkylene, alkyleneheteroaryleneheteroalkylene, alkyleneheterocyclyleneheteroalkylene, alkylenecarbocyclyleneheteroalkylene, heteroarylene, heterocyclylene, carbocyclylene, alkyleneheteroarylene, alkyleneheterocyclylene, heteroarylenealkylene, alkylenecarbocyclylene, carbocyclylenealkylene, heteroalkyleneheteroarylene, heteroalkyleneheterocyclylene, heteroaryleneheteroalkylene, heteroalkylenecarbocyclylene, carbocyclyleneheteroalkylene or heteroatomic linker. In some embodiments, $L^{1b}$ is an optionally substituted heteroalkenylene linker.

In some embodiments, at least one occurrence of $L^{1b}$ is substituted. In certain embodiments, $L^{1b}$ is substituted at each occurrence. In some more specific embodiments, $L^{1b}$ is substituted with oxo.

In other embodiments, $L^{1b}$ is at each occurrence, independently a linker comprising a functional group capable of formation by reaction of two complementary reactive groups (e.g., triazolyl, amide, etc.), for example a Q group.

The optional linkers $L^{1b}$ and $L^7$ can be used as a point of attachment of the $M^1$ and $M^2$ moieties to the remainder of the compound. For example, in some embodiments a synthetic precursor to the compound of structure (I) is prepared, and the $M^1$ and $M^2$ moieties are attached to the synthetic precursor using any number of facile methods known in the art, for example methods referred to as "click chemistry." For this purpose any reaction which is rapid and substantially irreversible can be used to attach $M^1$ and $M^2$ to the synthetic precursor to form a compound of structure (I). Exemplary reactions include the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, strain-promoted cycloalkyne-azide cycloaddition (Cu-free click), reaction of a strained alkene with an azide, tetrazine or tetrazole, alkene and azide [3+2]cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothioscyanate or the like. In some embodiments the reaction to form $L^{1b}$ or $L^7$ may be performed in an aqueous environment.

Accordingly, in some embodiments $L^{1b}$ or $L^7$ are at each occurrence, independently a linker comprising a functional group capable of formation by reaction of two complementary reactive groups, for example a functional group which is the product of one of the foregoing "click" reactions. In various embodiments, for at least one occurrence of $L^{1b}$ or $L^7$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group, for example, via a reaction of an amine with an N-hydroxysuccinimide ester or isothiocyanate.

In other embodiments, for at least one occurrence of $L^{1b}$ or $L^7$, the functional group can be formed by reaction of an alkyne and an azide. In other embodiments, for at least one occurrence of $L^{1b}$ or $L^7$, the functional group can be formed by reaction of an amine (e.g., primary amine) and an N-hydroxysuccinimide ester or isothiocyanate.

In more embodiments, for at least one occurrence of $L^{1b}$ or $L^7$, the functional group comprises an alkene, ester, amide, thioester, disulfide, carbocyclic, heterocyclic or heteroaryl group. In more embodiments, for at least one occurrence of $L^{1b}$ or $L^7$, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of $L^{1b}$ or $L^7$, $L^{1b}$ or $L^7$ are linkers comprising a triazolyl functional group. In some related embodiments, $L^{1b}$ or $L^7$, at each occurrence, independently comprises a triazolyl functional group. While in other embodiments, at least one occurrence of $L^{1b}$ or $L^7$ is a linker comprising an amide or thiourea functional group.

In still other embodiments, for at least one occurrence of $L^1$, $L^{1b}$-$M^1$ has the following structure:

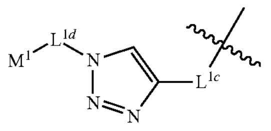

wherein $L^{1c}$ and $L^{1d}$ are each independently optional linkers.

In different embodiments, for at least one occurrence of $L^{1b}$, $L^{1b}$-$M^1$ has the following structure:

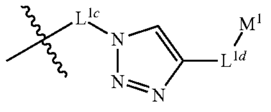

wherein $L^{1c}$ and $L^{1d}$ are each independently optional linkers.

In various embodiments of the foregoing, $L^{1c}$ or $L^{1d}$, or both, is absent.

In other embodiments, $L^{1c}$ or $L^{1d}$, or both, is present.

In some embodiments $L^{1c}$ and $L^{1d}$, when present, are each independently alkylene or heteroalkylene. For example, in some embodiments $L^{1c}$ and $L^{1d}$, when present, independently have one of the following structures:

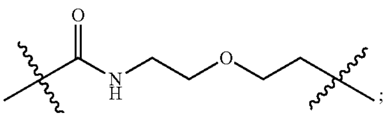
;

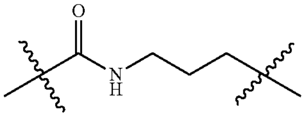
or

-continued

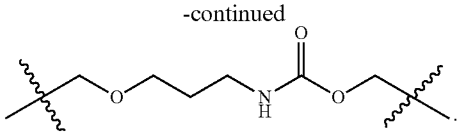

.

In still other embodiments, for at least one occurrence of $L^7$, $L^7$-$M^2$ has the following structure:

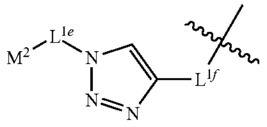

wherein $L^{1e}$ and $L^{1f}$ are each independently optional linkers.

In different embodiments, for at least one occurrence of $L^7$, $L^7$-$M^2$ has the following structure:

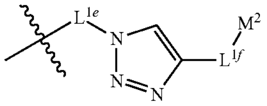

wherein $L^{1e}$ and $L^{1f}$ are each independently optional linkers.

In various embodiments of the foregoing, $L^{1e}$ or $L^{1f}$, or both, is absent. In other embodiments, $L^{1e}$ or $L^{1f}$, or both, is present.

In some embodiments $L^{1e}$ and $L^{1f}$, when present, are each independently alkylene or heteroalkylene. For example, in some embodiments $L^{1e}$ and $L^{1f}$, when present, independently have one of the following structures:

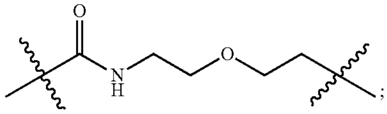

;

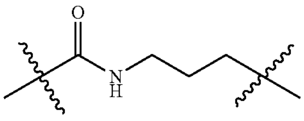

or

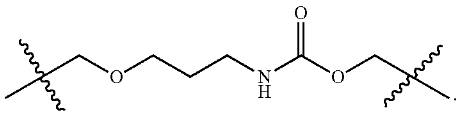

.

In still other different embodiments of structure (I), $L^{1b}$ is at each occurrence, independently an optional alkylene or heteroalkylene linker. In certain embodiments, $L^{1b}$ has one of the following structures:

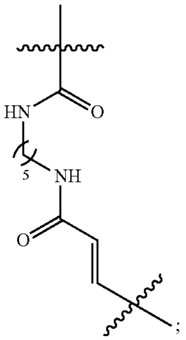

;

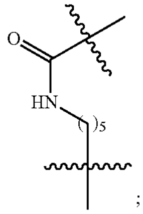

;

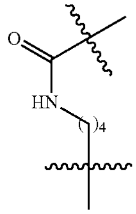

or

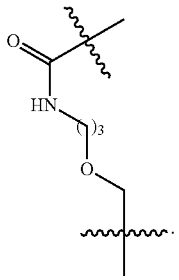

.

In some embodiments, at least one occurrence of $L^7$ is an optionally substituted heteroalkylene linker. In certain embodiments, $L^7$ is, at each occurrence, independently an optionally substituted heteroalkylene. In more specific embodiments, $L^7$ comprises an amide or a triazolyl functional group.

In still other different embodiments of structure (I), $L^7$ is at each occurrence, independently an optional alkylene or heteroalkylene linker. In certain embodiments, at least one occurrence of $L^7$ has one of the following structures:

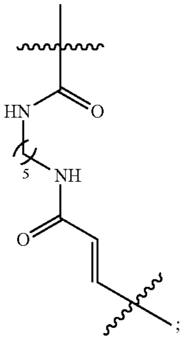

;

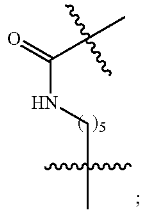

;

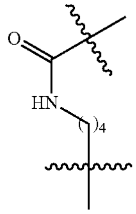

or

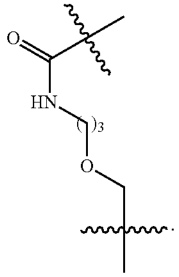

.

In some related embodiments, each occurrence of $L^7$ has one of the following structures:

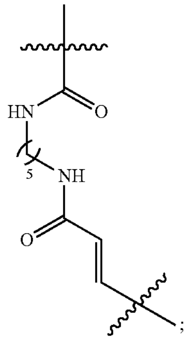;

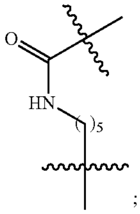;

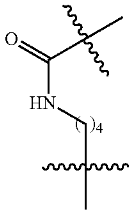

or

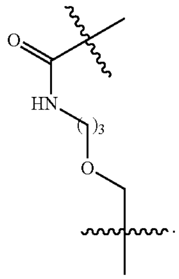

In some embodiments, at least one occurrence of $L^7$ has the following structure:

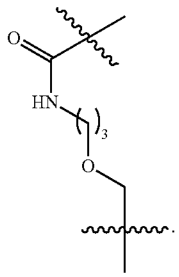

In some related embodiments, each occurrence of $L^7$ has the following structure:

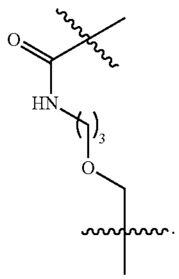

In some embodiments, at least one occurrence of $L^{1b}$ and/or $L^7$ has one of the following structures:

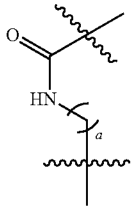

or

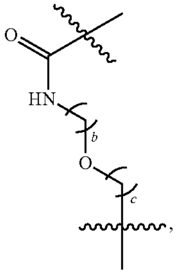, wherein a, b, and c are each independently an integer ranging from 1-6.

In some embodiments, each occurrence of $L^{1b}$ and/or $L^7$ has one of the following structures:

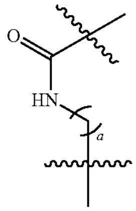

or

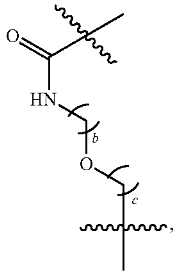, wherein a, b, and c are each independently an integer ranging from 1-6.

In some embodiments, at least one occurrence of $L^{1b}$ and/or $L^7$ has one of the following structures:

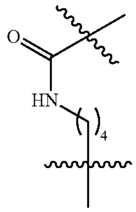

or

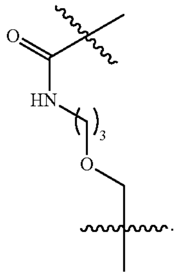

In still other different embodiments of structure (I), $L^{1b}$ and/or $L^7$ is at each occurrence, independently an optional alkylene or heteroalkylene linker. In certain embodiments, $L^{1b}$ and/or $L^7$ has one of the following structures:

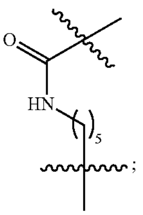;

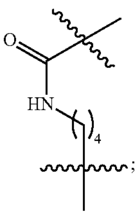;

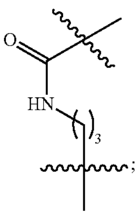;

-continued

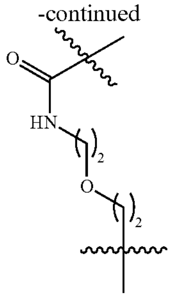

In some embodiments, at least one occurrence of $L^3$ is an alkylene linker. In some embodiments, at least one occurrence of $L^3$ is an alkylene linker. In more specific embodiments, $L^3$ or is an alkylene linker at each occurrence. In certain embodiments, the alkylene linker is a methylene linker.

In some embodiments, at least one occurrence of $L^2$ is absent. In more specific embodiments, $L^2$ is absent at each occurrence.

In certain embodiments, at least one occurrence of $L^5$ or $L^6$ is, independently a heteroalkylene linker. In some more specific embodiments, $L^5$ is a heteroalkylene linker at each occurrence and at least one occurrence of $L^6$ is absent. In some embodiments, at least one occurrence of $L^4$ comprises alkylene oxide. In some embodiments, at least one occurrence of $L^5$ or $L^6$ independently comprises alkylene oxide. In some of the foregoing embodiments, the alkylene oxide is ethylene oxide, for example, polyethylene oxide. In certain embodiments, at least one occurrence of $L^5$ or $L^6$ is an alkylene linker (e.g., methylene). In some more specific embodiments, $L^5$ or $L^6$ is an alkylene linker at each occurrence (e.g., methylene).

In certain embodiments, at least one occurrence of $L^5$ is a heteroalkylene linker. In some more specific embodiments, $L^5$ is a heteroalkylene linker at each occurrence. In some embodiments, at least one occurrence of $L^5$ comprises alkylene oxide, for example, ethylene oxide (e.g., polyethylene oxide). In certain embodiments, at least one occurrence of $L^5$ is an alkylene linker (e.g., methylene). In some more specific embodiments, $L^5$ is an alkylene linker at each occurrence (e.g., methylene). In certain embodiments, at least one occurrence of $L^5$ is absent. In some more specific embodiments, $L^5$ is absent at each occurrence.

In certain embodiments, at least one occurrence of $L^6$ is a heteroalkylene linker. In some more specific embodiments, $L^6$ is a heteroalkylene linker at each occurrence. In some embodiments, at least one occurrence of $L^6$ comprises alkylene oxide. In some of the foregoing embodiments, the alkylene oxide is ethylene oxide, for example, polyethylene oxide. In certain embodiments, at least one occurrence of $L^6$ is an alkylene linker (e.g., methylene). In some more specific embodiments, $L^6$ is an alkylene linker at each occurrence (e.g., methylene). In certain embodiments, at least one occurrence of $L^6$ is absent. In some more specific embodiments, $L^6$ is absent at each occurrence.

In certain embodiments, at least one occurrence of $L^5$ or $L^6$ comprises a phosphodiester moiety. In more specific embodiments, each occurrence of $L^5$ or $L^6$ comprises a phosphodiester moiety. In more embodiments, $L^2$, $L^3$, $L^4$ or $L^6$ are, at each occurrence, independently $C_1$-$C_6$ alkylene, $C_2$-$C_6$ alkenylene or $C_2$-$C_6$ alkynylene.

In some embodiments, at least one occurrence of $L^5$ is heteroalkylene. In some embodiments, $L^5$ is heteroalkylene at each occurrence, for example, a heteroalkylene comprising one of the following structures:

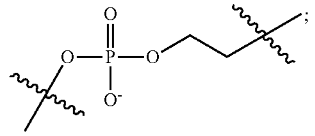

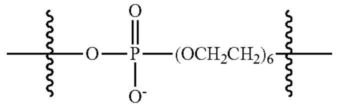

or

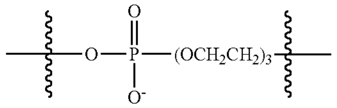

In some embodiments, at least one occurrence of $L^6$ is heteroalkylene. In some embodiments, $L^6$ is heteroalkylene at each occurrence, for example, a heteroalkylene comprising one of the following structures:

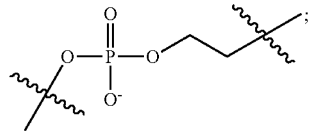

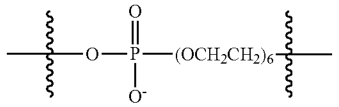

or

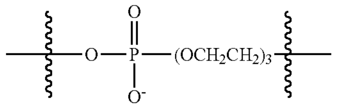

In some of the foregoing embodiments, a heteroalkylene (e.g., $L^3$, $L^4$, $L^5$ or $L^6$) comprises the following structure

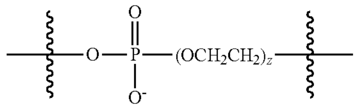

wherein z is an integer ranging from 20 to 30. In certain embodiments, the average z is 23. In certain embodiments, the average z is 24. In certain embodiments, the average z is 25. In certain embodiments, the average z is 26. In certain embodiments, the average z is 27. In some embodiments, the average z is 21, 22, 23, 24 or 25. In some embodiments, z is 24 or 25. In some embodiments, the average z is 21, 22, 23, 24, 25, 26 or 27.

In some embodiments, at least one occurrence of $L^5$ or $L^6$ independently comprises the following structure:

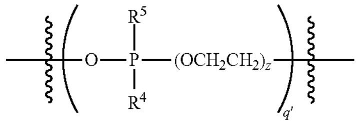

wherein q' is an integer from 1-20; and z is an integer from 1-100.

In some of the foregoing embodiments, z is an integer from 3 to 6. In some embodiments, z is an integer from 22 to 26, for example 22, 23, 24, 25, or 26. In some more specific embodiments, the average z is 23 or 24. In some embodiments, z is 24 or 25. In some embodiments, the average z is 21, 22, 23, 24, 25, 26 or 27.

In some of the foregoing embodiments, q' is 1. In other embodiments, q' is from 2 to 9.

In some embodiments, at least one occurrence of $R^3$ is H. In more specific embodiments, $R^3$ is H at each occurrence.

In some embodiments of structure (I), at least one occurrence of q is 0. In some embodiments of structure (I), q is 0 at each occurrence. In some related embodiments, the compound has the following structure (Ia):

(Ia)

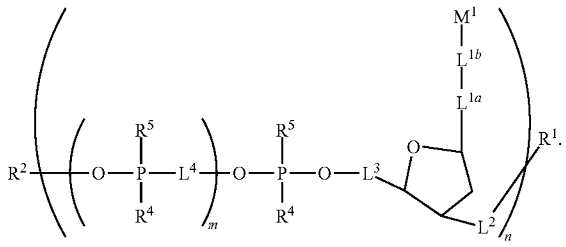

In some other embodiments, the compound has one of the following structures (Ib) or (Ic):

(Ia)

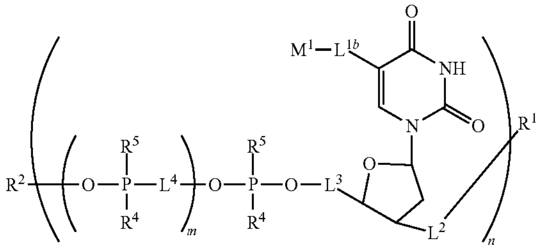

or (Ib)

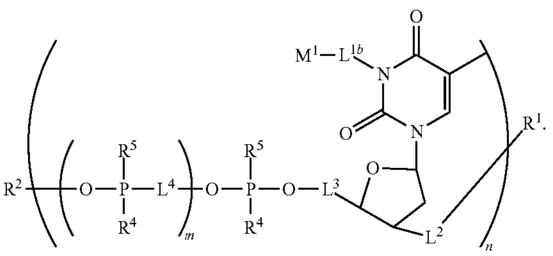

wherein:

$L^{1b}$ is, at each occurrence, independently an optionally substituted alkylene or an optionally substituted heteroalkylene linker.

In some embodiments, the compound has one of the following structures (Id) or (Ie):

(Id)

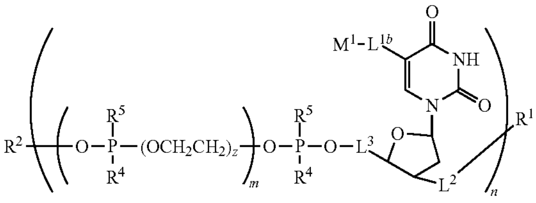

or (Ie)

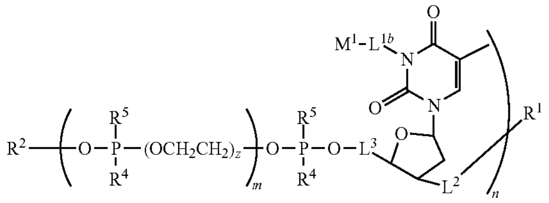

wherein:

z is an integer from 1 to 100.

In some embodiments, z is 24 or 25. In some embodiments, the average z is 21, 22, 23, 24, 25, 26 or 27.

In some embodiments, $L^{1b}$, at each occurrence, independently comprises an amide functional group or a triazolyl functional group.

In some embodiments of structure (I), at least one occurrence of m is 0. In some embodiments of structure (I), m is 0 at each occurrence. In some related embodiments, the compound has one of the following structures (If):

(If)

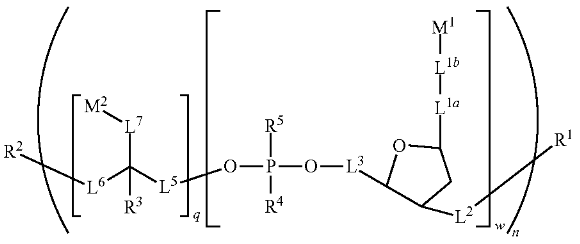

In some more specific embodiments, the compound has one of the following structures (Ig) or (Ih):

(Ig)

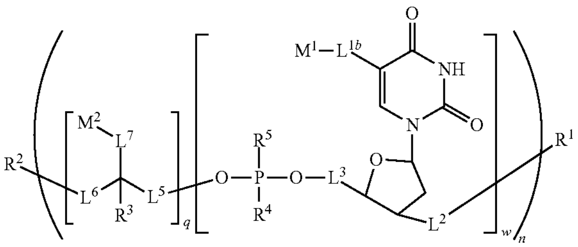

-continued (Ih)

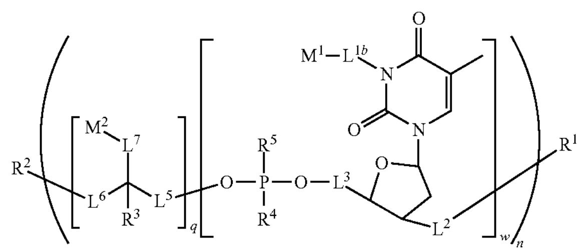

In some more specific embodiments, the compound has one of the following structures (Ij) or (Ik):

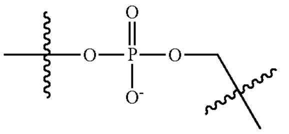

or

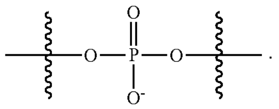

In some more specific embodiments of structures (If), (Ig), (Ih), (Ij) or (Ik), each occurrence of $L^6$ comprises one of the following structures:

(Ij)

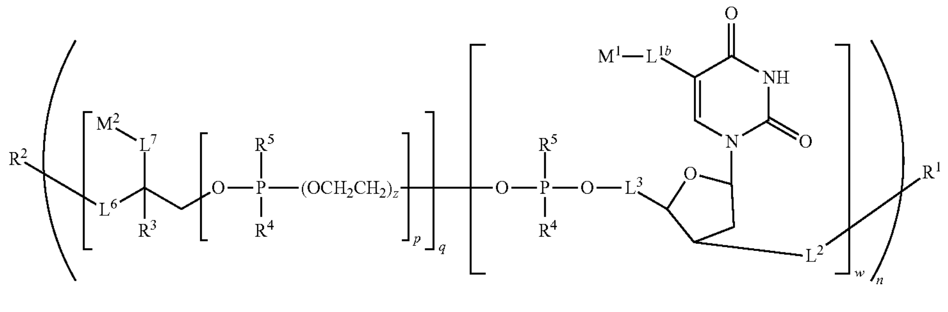

(Ik)

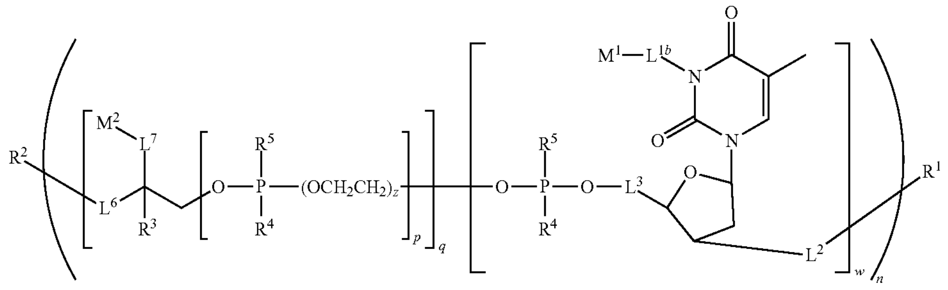

wherein z is, at each occurrence, independently an integer from 1 to 100; and p is, at each occurrence, independently an integer of zero or greater.

In some embodiments of structures (Ij) or (Ik), at least one occurrence of z ranges from 3 to 6. In some more specific embodiments of structures (Ij) or (Ik), z ranges from 3 to 6 at each occurrence. For example, in some of the foregoing embodiments, z is 3 or z is 6. In some embodiments, z is 24 or 25. In some embodiments, the average z is 21, 22, 23, 24, 25, 26 or 27.

In some embodiments of structures (Ij) or (Ik), at least one occurrence of p ranges from 1 to 20. In some more specific embodiments of structures (Ij) or (Ik), p ranges from 1 to 20 at each occurrence. For example, in some of the foregoing embodiments, p is 2, 3, 4, 5, 6, 7, 8, 9 or 10.

In some of the foregoing embodiments of structures (If), (Ig), (Ih), (Ij) or (Ik), at least one occurrence of $L^6$ comprises one of the following structures:

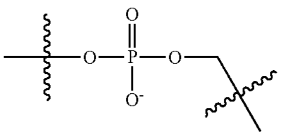

or

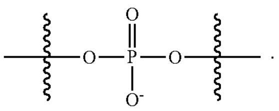

In some embodiments of structure (I), at least one occurrence of w is 0. In some embodiments of structure (I), w is 0 at each occurrence. In some related embodiments, the compound has one of the following structures (Im):

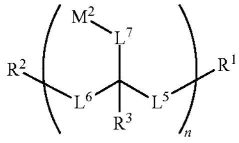

(Im)

In some more specific embodiments, the compound has the following structure (In):

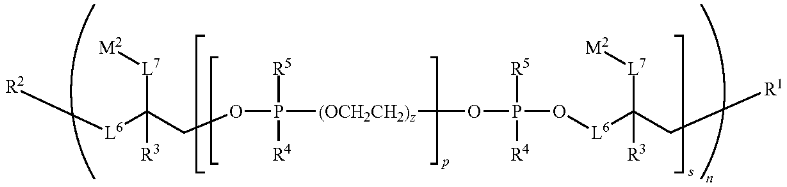

(In)

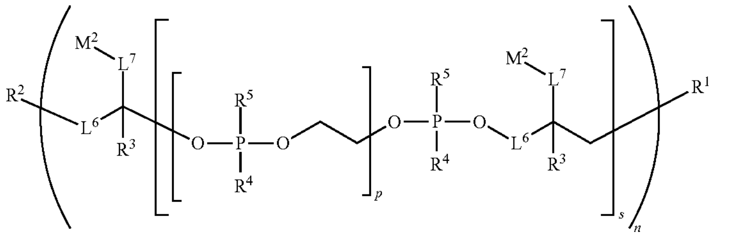

(Io)

wherein:

s is, at each occurrence, independently an integer of 0 or greater;

z is, at each occurrence, independently an integer from 1 to 100;

p is, at each occurrence, independently an integer of zero or greater; and $L^7$ is, at each occurrence, independently an optionally substituted heteroalkylene linker.

In some embodiments, z is 6 and p is 3. In some embodiments, the average z ranges from 21 to 25, for example 21, 22, 23, 24, or 25. In some embodiments, z is 3. In some embodiment, z is 24 or 25. In some embodiments, the average z is 21, 22, 23, 24, 25, 26 or 27. In some embodiments, z is 25 and s is 4. In some embodiments, z is 25 s is 4 and n is 1.

In some of the foregoing embodiments, $L^6$ is absent, for example, at each occurrence. In some of the foregoing embodiments of structures (Im) or (In), at least one occurrence of L comprises one of the following structures:

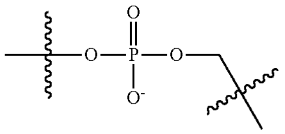

or

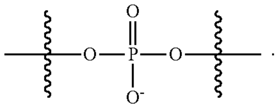

.

In some more specific embodiments of structures (Im) or (In), each occurrence of $L^6$ comprises one of the following structures:

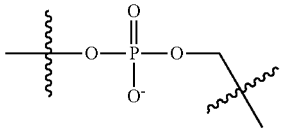

or

-continued

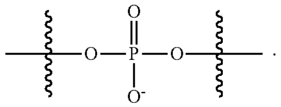

.

In different embodiments of structures (Im) or (In), at least one occurrence of $L^6$ is alkylene, for example, methylene. In some related embodiments of structures (Im) or (In), $L^6$ is alkylene at each occurrence, for example, methylene.

In some embodiments of the structures (In) or (Io), at least one occurrence of $L^6$ is heteroalkylene. In some embodiments of the structures (In) or (Io), $L^6$ is heteroalkylene at each occurrence, for example, a heteroalkylene comprising one of the following structures:

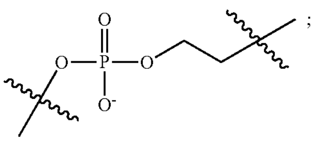

;

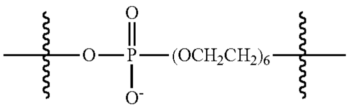

or

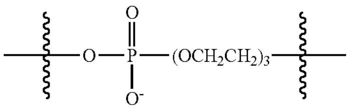

In some of the foregoing embodiments of structures (Im) or (In), at least one occurrence of $L^5$ comprises one of the following structures:

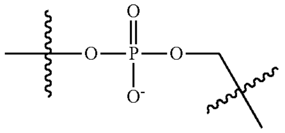

or

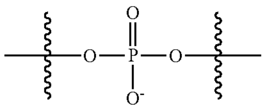

In some more specific embodiments of structures (Im) or (In), each occurrence of $L^5$ comprises one of the following structures:

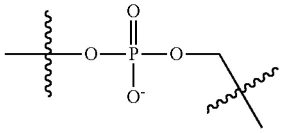

or

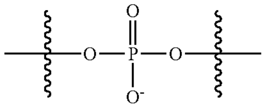

In different embodiments of structures (Im) or (In), at least one occurrence of $L^5$ is alkylene, for example, methylene. In some related embodiments of structures (Im) or (In), $L^5$ is alkylene at each occurrence, for example, methylene.

In some embodiments of the structures (In) or (Io), at least one occurrence of $L^5$ is heteroalkylene. In some embodiments of the structures (In) or (Io), $L^5$ is heteroalkylene at each occurrence, for example, a heteroalkylene comprising one of the following structures:

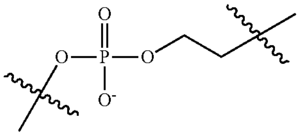

;

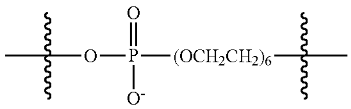

or

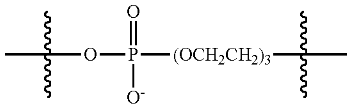

In some of the foregoing embodiments, $L^6$ is absent.

In some of the foregoing embodiments of the structures (In) or (Io), a heteroalkylene (e.g., $L^3$, $L^4$, $L^5$ or $L^6$) comprises the following structure:

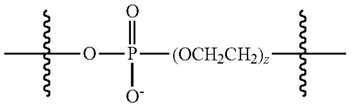

wherein z is an integer ranging from 20 to 30. In certain embodiments, the average z is 24 or 25. In some embodiments, the average z is 21, 22, 23, 24, 25, 26 or 27.

In still other embodiments of any of the compounds of structures (I), (Ia), (Ib), (Ic), (Id), (Je), (If), (Ig), (Ih), (Ij), (Ik), (Im). (In) or (Io), $R^5$ is, at each occurrence, independently OH, $O^-$ or $OR_d$. It is understood that "$OR_d$" and "$SR_d$" are intended to refer to $O^-$ and $S^-$ associated with a cation. For example, the disodium salt of a phosphate group may be represented as:

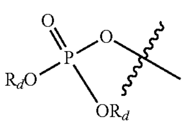

, where $R_d$ is sodium ($Na^+$).

In other embodiments of any of the compounds of structures (I), (Ia), (Ib), (Ic), (Id), (Je), (If), (Ig), (Ih), (Ij), (Ik), (Im). (In) or (Io) at least one occurrence of $R^4$ is oxo. In other embodiments of any of the compounds of structure (I), $R^4$ is, at each occurrence, oxo.

In other various embodiments, R and $R^2$ are each independently OH or $—OP(=R_a)(R_b)R_c$. In some different embodiments, $R^1$ or $R^2$ is OH or $—OP(=R_a)(R_b)R_c$, and the other of $R^1$ or $R^2$ is Q or a linker comprising a covalent bond to Q.

In still more different embodiments of any of the foregoing compounds of structures (I), (Ia), (Ib), (Ic), (Id), (Je), (If), (Ig), (Ih), (Ij), (Ik), (Im). (In) or (Io) $R^1$ and $R^2$ are each independently $—OP(=R_a)(R_b)R_c$. In some of these embodiments, $R_c$ is OL'.

In other embodiments, $R^1$ and $R^2$ are each independently $—OP(=R_a)(R_b)OL'$, and L' is an alkylene or heteroalkylene linker to: Q, a targeting moiety, an analyte (e.g., analyte molecule), a solid support, a solid support residue, a nucleoside or a further compound of structure (I).

The linker L' can be any linker suitable for attaching Q, a targeting moiety, an analyte (e.g., analyte molecule), a solid support, a solid support residue, a nucleoside or a further compound of structure (I) to the compound of structure (I). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

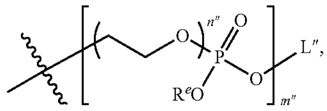

, wherein:

m" and n" are independently an integer from 1 to 10;

$R^e$ is H, an electron pair or a counter ion;

L" is $R^e$ or a direct bond or linkage to: Q, a targeting moiety, an analyte (e.g., analyte molecule), a solid support, a solid support residue, a nucleoside or a further compound of structure (I).

In some embodiments, m" is an integer from 4 to 10, for example 4, 6 or 10. In other embodiments n" is an integer from 3 to 6, for example 3, 4, 5 or 6. In some embodiments, n" is an integer from 18-28, for example, from 21-23.

In some other embodiments, L" is an alkylene, alkyleneheterocyclylene, alkyleneheterocyclylenealkylene, alkylenecyclylene, alkylenecyclylenealkylene, heteroalkylene, heteroalkyleneheterocyclylene, heteroalkyleneheterocyclyleneheteroalkylene, heteroalkylenecyclylene, or heteroalkylenecycleneheteroalkylene moiety. In some other certain embodiments, L" comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In other more specific embodiments of any of the foregoing compounds of structure (I), $R^1$ or $R^2$ has one of the following structures:

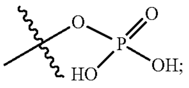

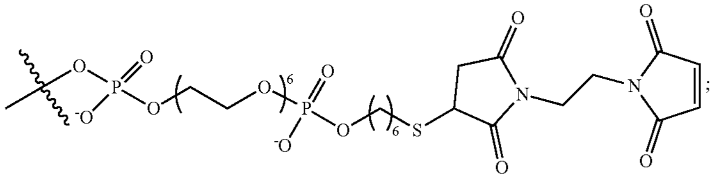

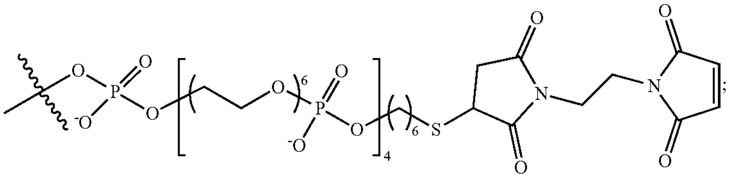

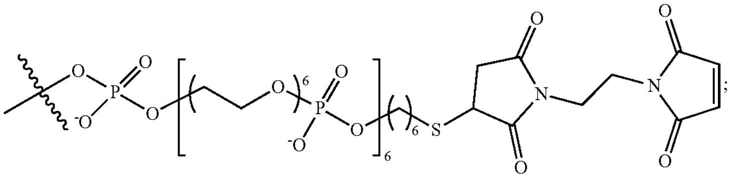

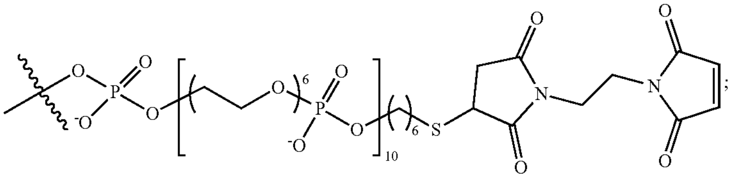

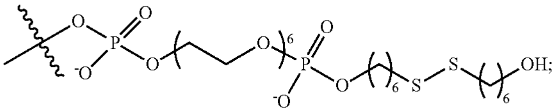

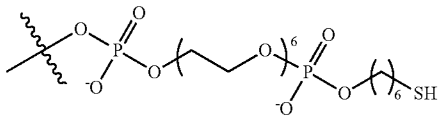

or

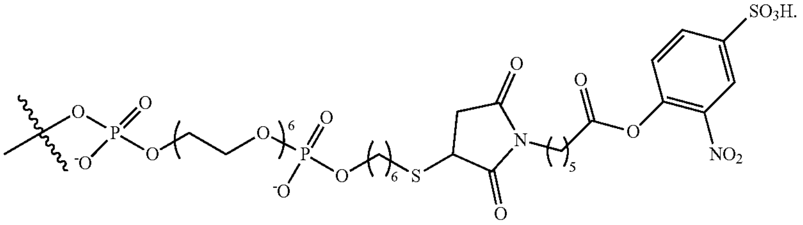

In other more specific embodiments of any of the foregoing compounds of structure (I), $R^1$ or $R^2$ has one of the following structures:

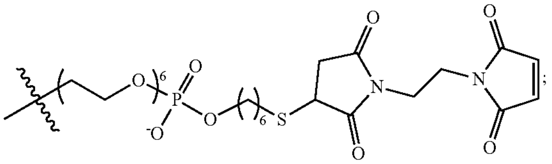

-continued

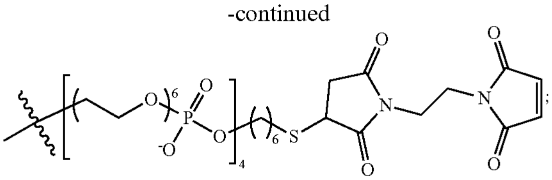
;
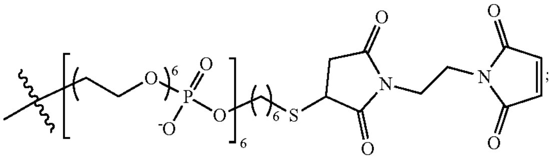
;
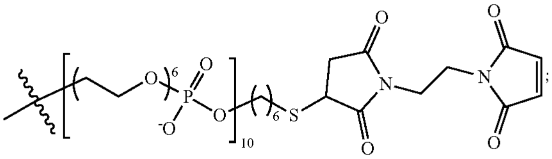
;
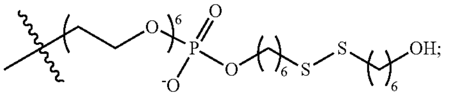

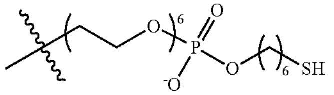
or

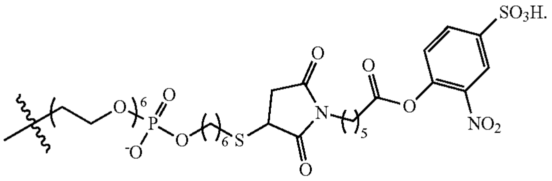

Certain embodiments of compounds of structure (I) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (I). Accordingly, in some embodiments $R^1$ or $R^2$ has the following structure:

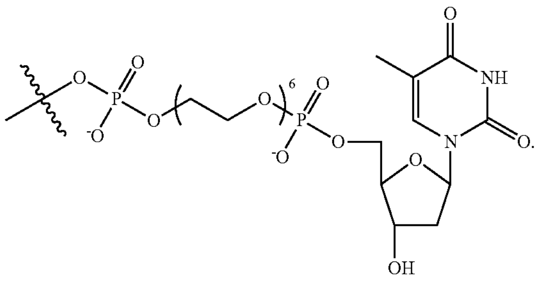

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) (e.g., in the $R^1$ or $R^2$ position), and Q and Q' comprise complementary reactive groups such that reaction of the compound of structure (I) and the further compound of structure (I) results in covalently bound dimer of the compound of structure (I). Multimer compounds of structure (I) can also be prepared in an analogous manner and are included within the scope of embodiments of the invention.

The type of Q group and connectivity of the Q group to the remainder of the compound of structure (I) is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

Exemplary Q moieties are provided in Table 1 below.

TABLE 1

Exemplary Q Moieties

| Structure | Class |
|---|---|
| 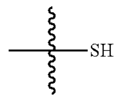 | Sulfhydryl |
| 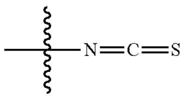 [SMILES: *N=C=S] | Isothiocyanate |

TABLE 1-continued
Exemplary Q Moieties
| Structure | Class |
|---|---|
| 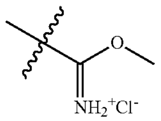 | Imido-ester |
| 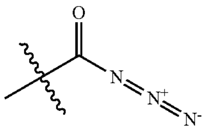 [SMILES: *C(=O)N=[N+]=[N-]] | Acyl Azide |
| 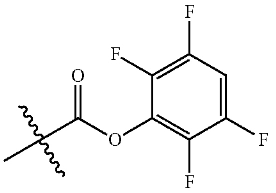 [SMILES: *C(=O)Oc1c(F)c(F)cc(F)c1F] | Activated Ester |
| 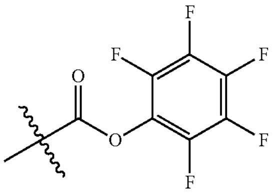 [SMILES: *C(=O)Oc1c(F)c(F)c(F)c(F)c1F] | Activated Ester |
| 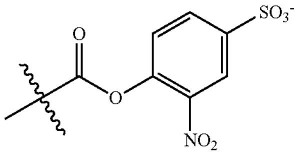 | Activated Ester |
| 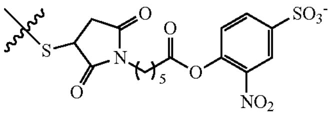 | Activated Ester |
| 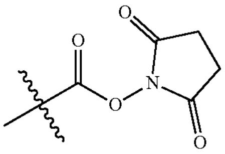 [SMILES: *C(=O)ON1C(=O)CCC1=O] | Activated Ester |
| 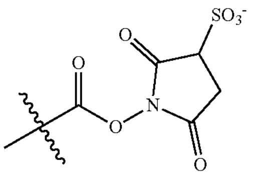 | Activated Ester |
| 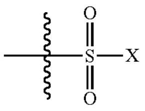 X = halo | Sulfonyl halide |
TABLE 1-continued
Exemplary Q Moieties
| Structure | Class |
|---|---|
| 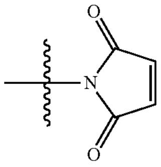 [SMILES: *N1C(=O)C=CC1=O] | Maleimide |
| 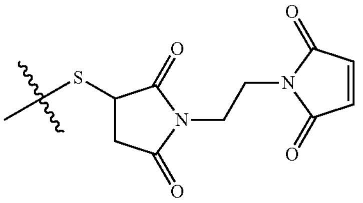 [SMILES: *SC1CC(=O)N(CCN2C(=O)C=CC2=O)C1=O] | Maleimide |
| 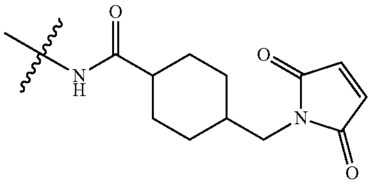 [SMILES: *NC(=O)C1CCC(CN2C(=O)C=CC2=O)CC1] | Maleimide |
| 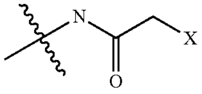 X = halo | α-haloimide |
| 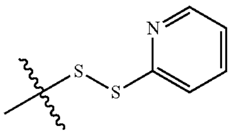 [SMILES: *SSc1ccccn1] | Disulfide |
| 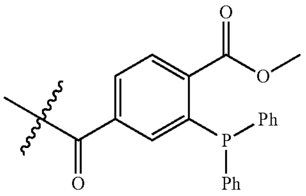 [SMILES: *C(=O)c1ccc(C(=O)OC)c(P(c2ccccc2)c2ccccc2)c1] | Phosphine |
| 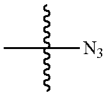 [SMILES: *N=[N+]=[N-]] | Azide |
| 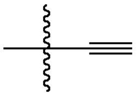 [SMILES: *C#C] | Alkyne |
| 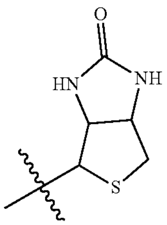 [SMILES: *C1SCC2NC(=O)NC21] | Biotin |

TABLE 1-continued

| Exemplary Q Moieties | |
|---|---|
| Structure | Class |
| 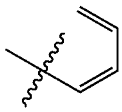 [SMILES: */C=C\C=C] | Diene |
| 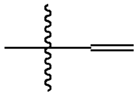 [SMILES: *C=C] | Alkene/ dienophile |
| 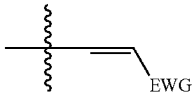 EWG = eletron withdrawing group | Alkene/ dienophile |
| —$NH_2$ | Amino |

It should be noted that in some embodiments, wherein Q is SH, the SH moiety will tend to form disulfide bonds with another sulfhydryl group, for example on another compound of structure (I). Accordingly, some embodiments include compounds of structure (I), which are in the form of disulfide dimers, the disulfide bond being derived from SH Q groups.

Also included within the scope of certain embodiments are compounds of structure (I), wherein one, or both, of $R^1$ and $R^2$ comprises a linkage to a further compound of structure (I). For example, wherein one or both of $R^1$ and $R^2$ are —$OP(=R_a)(R_b)R_c$, and $R_c$ is OL', and L' is a linker comprising a covalent bond to a further compound of structure (I). Such compounds can be prepared by preparing a first compound of structure (I) having for example about 10 "$M^1$" and/or "$M^2$" moieties (i.e., n=10) and having an appropriate "Q" for reaction with a complementary Q' group on a second compound of structure (I). In this manner, compounds of structure (I), having any number of "$M^1$" and/or "$M^2$" moieties, for example 100 or more, can be prepared without the need for sequentially coupling each monomer. Exemplary embodiments of such compounds of structure (I) have the following structure (I')

(I')

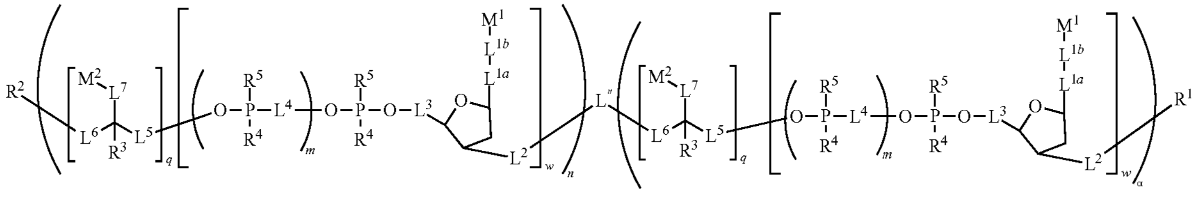

wherein:

each occurrence of $R^1$, $R^2$, $R^3$, $R^4$, $R^5$, $L^{1a}$, $L^{1b}$, $L^2$, $L^3$, $L^4$, $L^5$, $L^6$, $L^7$, $M^1$, $M^1$, q, m, w and n are independently as defined for a compound of structure (I);

L" is a linker comprising a functional group resulting from reaction of a Q moiety with a corresponding Q' moiety; and α is an integer greater than 1, for example from 1 to 100, or 1 to 10.

Compounds of structure (I') are derivable by those of ordinary skill in the art, for example by dimerizing or polymerizing compounds of structure (I) provided herein.

In other embodiments, the Q moiety is conveniently masked (e.g., protected) as a disulfide moiety, which can later be reduced to provide an activated Q moiety for binding to a desired analyte molecule or targeting moiety. For example, the Q moiety may be masked as a disulfide having the following structure:

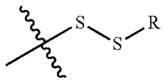

wherein R is an optionally substituted alkyl group. For example, in some embodiments, Q is provided as a disulfide moiety having the following structure:

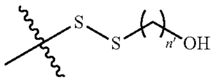

where n is an integer from 1 to 10.

In some other embodiments, one of $R^1$ or $R^2$ is OH or —$OP(=R_a)(R_b)R_c$, and the other of $R^1$ or $R^2$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In some embodiments, the targeting moiety is an antibody or cell surface receptor antagonist. In still different embodiments, the solid support is a polymeric bead or non-polymeric bead.

The fluorescence intensity can also be tuned by selection of different values of the variables n, m, q, p, s and w. In certain embodiments, n is an integer from 1 to 100. In other embodiments, n is an integer from 1 to 10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In certain embodiments, m is an integer from 1 to 100. In other embodiments, m is an integer from 7 to 12. In some embodiments, m is an integer from 20 to 26. In some embodiments, m is an integer from 3 to 6. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11.

In certain embodiments, w is an integer from 1 to 100. In other embodiments, w is an integer from 7 to 12. In some embodiments, w is an integer from 20 to 26. In some embodiments, w is an integer from 3 to 6. In some embodiments, w is 3. In some embodiments, w is 4. In some embodiments, w is 5. In some embodiments, w is 6. In some embodiments, w is 7. In some embodiments, w is 8. In some embodiments, w is 9. In some embodiments, w is 10. In some embodiments, w is 11.

In certain embodiments, p is an integer from 1 to 100. In other embodiments, p is an integer from 7 to 12. In some embodiments, p is an integer from 20 to 26. In some embodiments, p is an integer from 3 to 6. In some embodiments, p is 3. In some embodiments, p is 4. In some embodiments, p is 5. In some embodiments, p is 6. In some embodiments, p is 7. In some embodiments, p is 8. In some embodiments, p is 9. In some embodiments, p is 10. In some embodiments, p is 11.

In certain embodiments, s is an integer from 1 to 100. In other embodiments, s is an integer from 7 to 12. In some embodiments, s is an integer from 20 to 26. In some embodiments, s is an integer from 3 to 6. In some embodiments, s is 3. In some embodiments, s is 4. In some embodiments, s is 5. In some embodiments, s is 6. In some embodiments, s is 7. In some embodiments, s is 8. In some embodiments, s is 9. In some embodiments, s is 10. In some embodiments, s is 11.

In certain embodiments, q is an integer from 1 to 100. In other embodiments, q is an integer from 7 to 12. In some embodiments, q is an integer from 20 to 26. In some embodiments, q is an integer from 3 to 6. In some embodiments, q is 3. In some embodiments, q is 4. In some embodiments, q is 5. In some embodiments, q is 6. In some embodiments, q is 7. In some embodiments, q is 8. In some embodiments, q is 9. In some embodiments, q is 10. In some embodiments, q is 11.

$M^1$ and $M^2$ are selected based on the desired optical properties, for example based on a desired color and/or fluorescence emission wavelength. In some embodiments, $M^1$ and $M^2$ are the same at each occurrence; however, it is important to note that each occurrence of $M^1$ and $M^2$ need not be an identical $M^1$ and $M^2$, and certain embodiments include compounds wherein $M^1$ and $M^2$ are not the same at each occurrence. For example, in some embodiments each $M^1$ and $M^2$ are not the same and the different $M^1$ and $M^2$ moieties are selected to have absorbance and/or emissions for use in fluorescence resonance energy transfer (FRET) methods. For example, in such embodiments the different $M^1$ and $M^2$ moieties are selected such that absorbance of radiation at one wavelength causes emission of radiation at a different wavelength by a FRET mechanism. Exemplary $M^1$ and $M^2$ moieties can be appropriately selected by one of ordinary skill in the art based on the desired end use. Exemplary $M^1$ and $M^2$ moieties for FRET methods include fluorescein and 5-TAMRA (5-carboxytetramethylrhodamine, succinimidyl ester) dyes.

$M^1$ or $M^2$ may be attached to the remainder of the molecule from any position (i.e., atom) on $M^1$ or $M^2$, respectively. One of skill in the art will recognize means for attaching $M^1$ or $M^2$ to the remainder of molecule. Exemplary methods include the "click" reactions described herein.

In some embodiments, $M^1$ and $M^2$ are, at each occurrence, independently a fluorescent or colored moiety (e.g., a chromophore). Any fluorescent and/or colored moiety may be used, for examples those known in the art and typically employed in colorimetric, UV, and/or fluorescent assays may be used. Examples of $M^1$ and $M^2$ moieties which are useful in various embodiments of the invention include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary $M^1$ and $M^2$ moieties include: Cyanine dyes, xanthate dyes (e.g., Hex, Vic, Nedd, Joe or Tet); Yakima yellow; Redmond red; tamra; texas red and Alexa Fluor® dyes.

In still other embodiments of any of the foregoing, $M^1$ or $M^2$ at one or more occurrences independently comprises three or more aryl or heteroaryl rings, or combinations thereof, for example four or more aryl or heteroaryl rings, or combinations thereof, or even five or more aryl or heteroaryl rings, or combinations thereof. In some embodiments, $M^1$ and $M^2$ at one or more occurrences independently comprise six aryl or heteroaryl rings, or combinations thereof. In further embodiments, the rings are fused. For example in some embodiments, $M^1$ and $M^2$ at one or more occurrences independently comprise three or more fused rings, four or more fused rings, five or more fused rings, or even six or more fused rings.

In some embodiments, $M^1$ or $M^2$ are, at one or more occurrences, independently cyclic. For example, in some embodiments $M^1$ and $M^2$ are, at one or more occurrences, independently carbocyclic. In other embodiment, $M^1$ and $M^2$ are, at one or more occurrences, independently heterocyclic. In still other embodiments of the foregoing, $M^1$ and $M^2$ are, at one or more occurrences, independently comprises an aryl moiety. In some of these embodiments, the aryl moiety is multicyclic. In other more specific examples, the aryl moiety is a fused-multicyclic aryl moiety, for example which may comprise at least 2, at least 3, at least 4, or even more than 4 aryl rings.

In other embodiments of any of the foregoing compounds of structure (I), (Ia), (Ib), (Ic), (Id), (Ie), (If), (Ig), (Ih), (Ij), (Ik), (Im), (In) or (I'), $M^1$ or $M^2$ at one or more occurrences, independently comprises at least one heteroatom. For example, in some embodiments, the heteroatom is nitrogen, oxygen or sulfur.

In still more embodiments of any of the foregoing, $M^1$ and $M^2$, at one or more occurrences, independently comprise at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, $M^1$ or $M^2$, at one or more occurrences, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyldimethyl-difluorobora-diaza-indacene)phenyl, (bis-fluorophenyl-difluorobora-diaza-indacene)phenyl, quaterphenyl, bi-benzothiazole, ter-benzothiazole, bi-naphthyl, bi-anthracyl, squaraine, squarylium, 9, 10-ethynylanthracene or ter-naphthyl moiety. In other embodiments, $M^1$ and $M^2$ are, at one or more occurrences, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, $M^1$ and $M^2$ are, at one or more occurrences, independently a coumarin dye, resorufin dye, dipyrrometheneboron difluoride dye, ruthenium bipyridyl dye, energy transfer dye, thiazole orange dye, polymethine or N-aryl-1,8-naphthalimide dye.

In still more embodiments of any of the foregoing, $M^1$ and $M^2$ at one or more occurrences are the same. In other embodiments, each $M^1$ and $M^2$ are different. In still more embodiments, one or more $M^1$ and $M^2$ are the same and one or more M and $M^2$ are different.

In some embodiments, $M^1$ and $M^2$ are, at one or more occurrences, independently pyrene, perylene, perylene monoimide or 6-FAM or a derivative thereof. In some other embodiments, $M^1$ or $M^2$, at one or more occurrences, independently has one of the following structures:

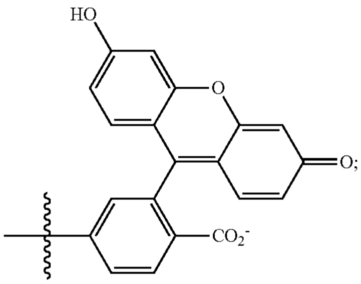

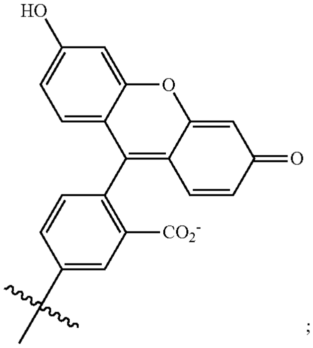

;

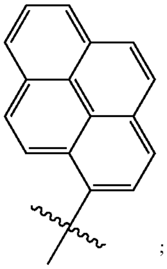

;

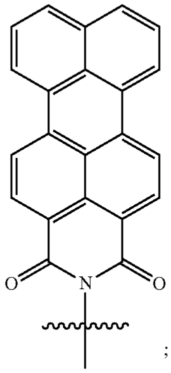

;

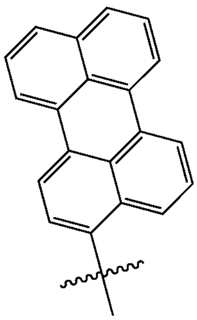

;

-continued

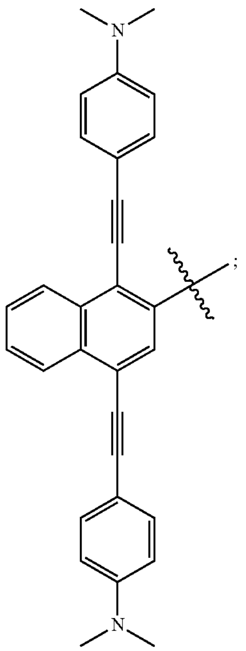

;

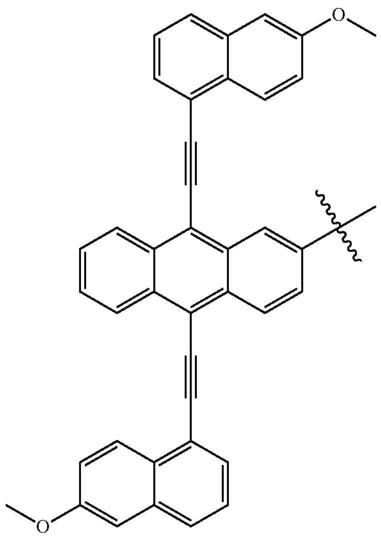

or

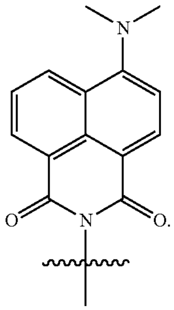

Although $M^1$ and $M^2$ moieties comprising carboxylic acid groups are depicted in the anionic form ($CO_2^-$) above, one of skill in the art will understand that this will vary depending on pH, and the protonated form (i.e., —$CO_2H$) is included in various embodiments.

In some other embodiments, $M^1$ or $M^2$, at each occurrence, independently has one of the following structures:

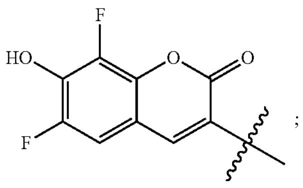
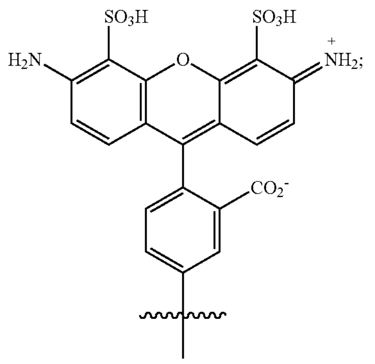
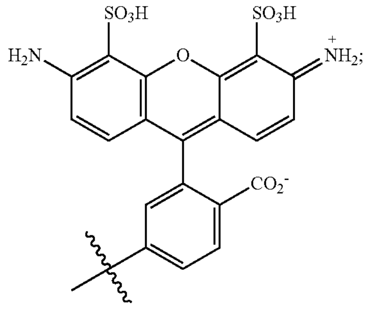
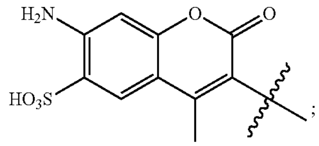
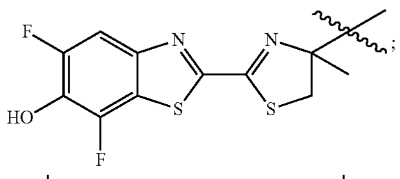
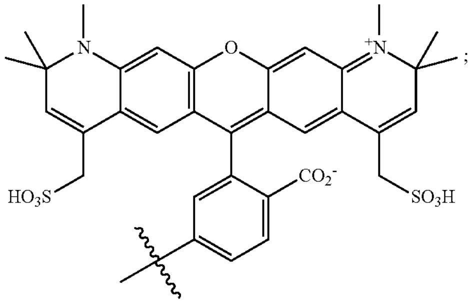
-continued
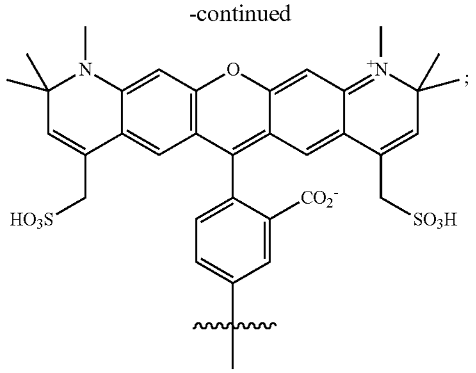
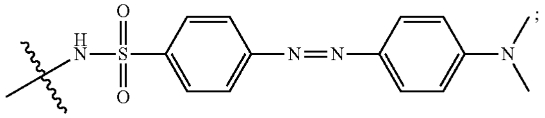
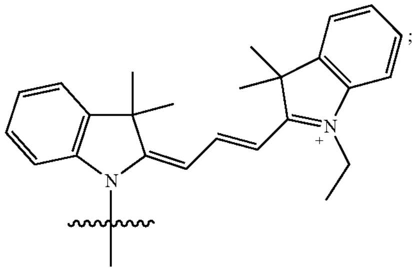
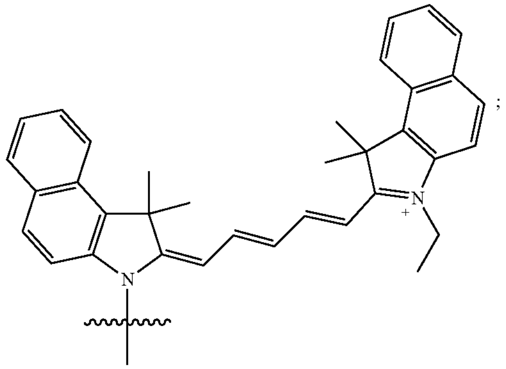
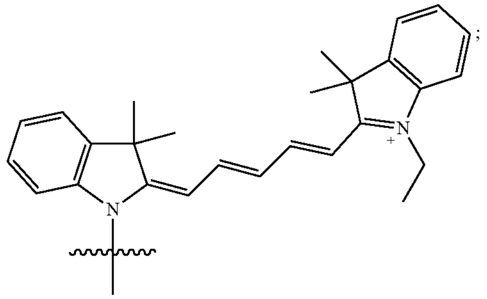
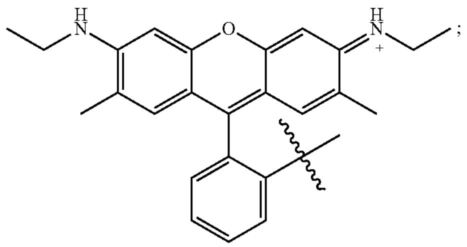

-continued
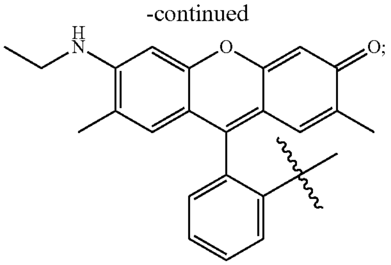
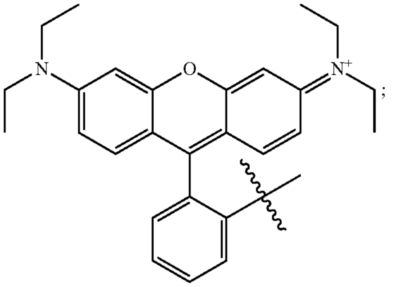
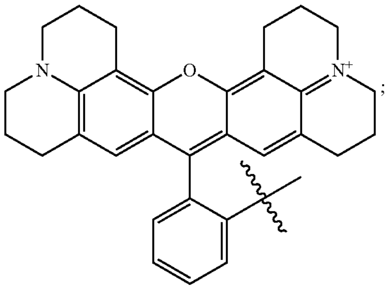
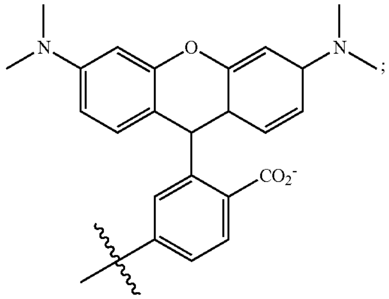
or
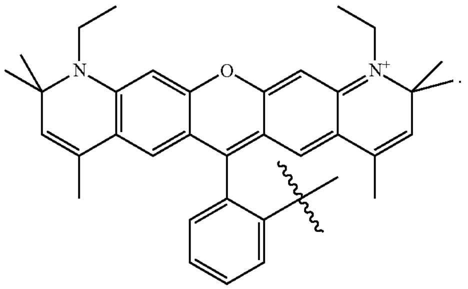
In some embodiments, $M^1$ or $M^2$ at one or more occurrences, independently has one of the following structures:
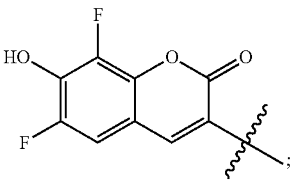
-continued
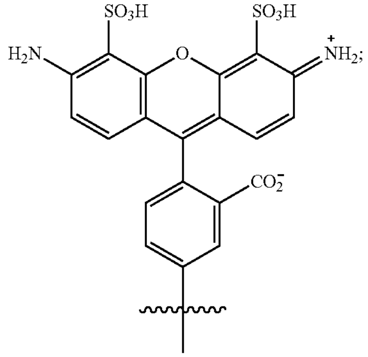
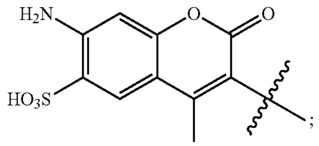
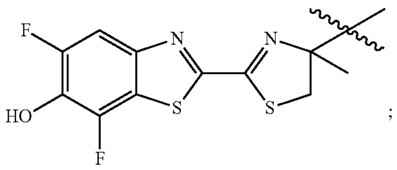
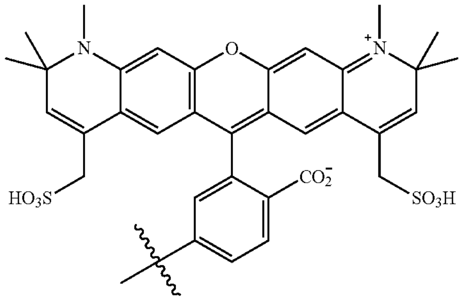
or
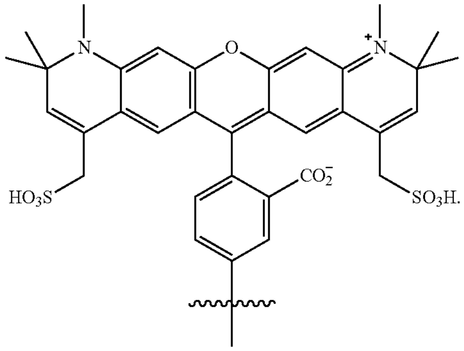
In some embodiments, $M^1$ and $M^2$ at each occurrence, independently have one of the following structures:
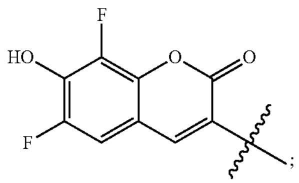

-continued

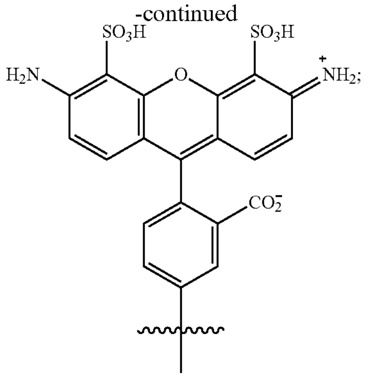

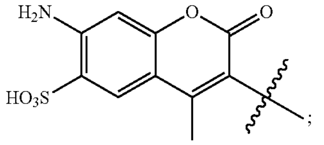

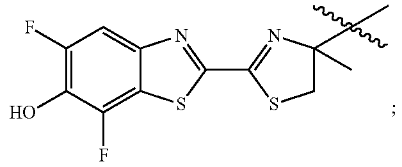

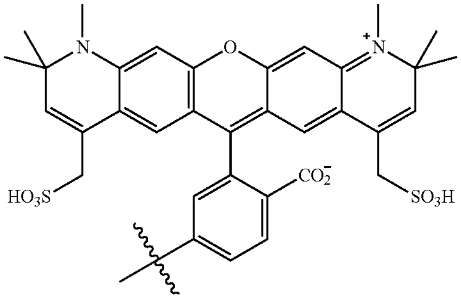

or

-continued

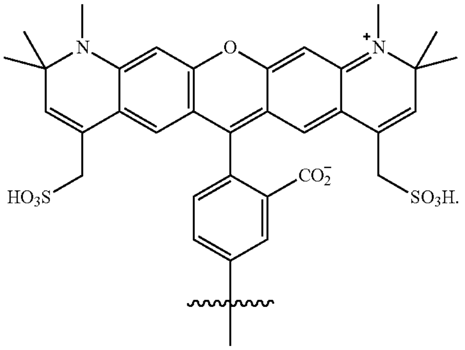

For ease of illustration, various compounds comprising carboxy/carboxylic acid and/or sulfate/sulfonic acid moieties are depicted in the anionic or protonated state, respectively (e.g., —$CO_2^-$ and —$SO_3H$). One of skill in the art will readily understand that the charge is dependent on pH and the uncharged (e.g., protonated or salt, such as sodium, potassium, lithium or other cation) forms are also included in the scope of embodiments of the invention. Certain $M^1$ and/or $M^2$ moieties have an overall positive a charge. As such, in certain embodiments the $M^1$ and/or $M^2$ moieties may be associated with an appropriate counter anion (e.g., $PF_6^-$, $Cl^-$, $F^-$, $NO_3^-$, $SO_3^-$ and the like).

In certain embodiments, $-L^{1a}-L^{1b}-M^1$ at each occurrence, independently has one of the following structures

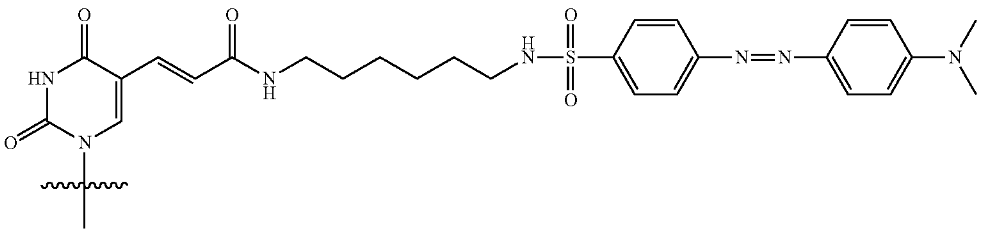

or

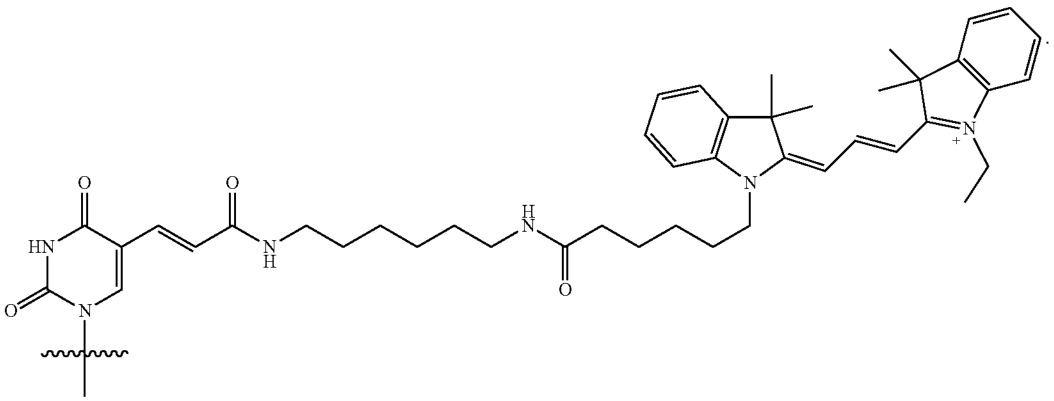

In some embodiments, $-L^7-M^2$ at each occurrence, independently has one of the following structures:
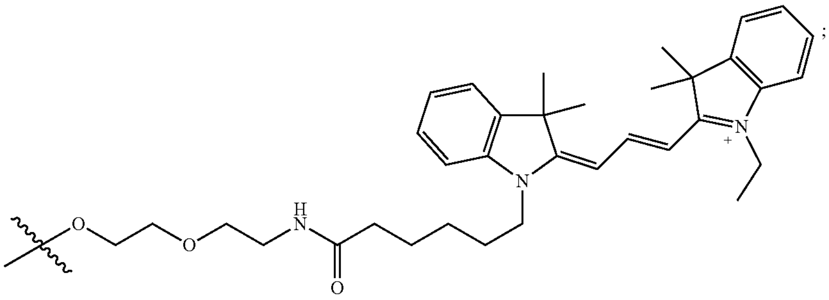
;
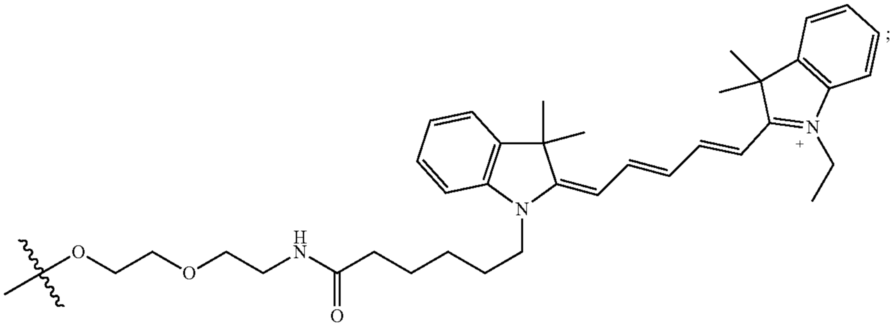
;
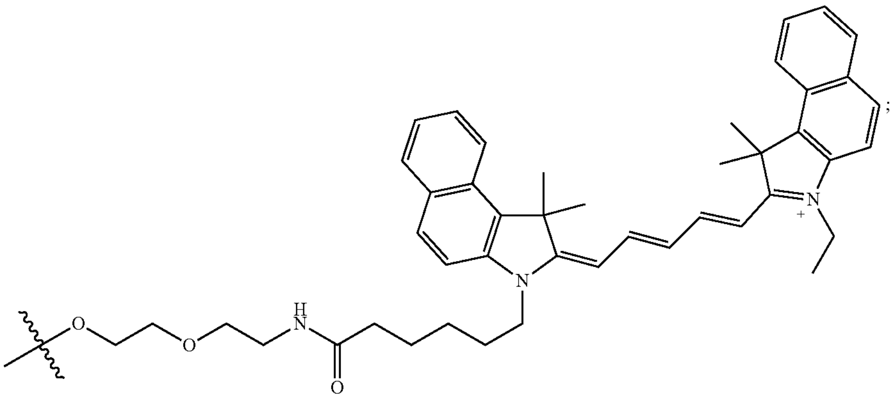
;
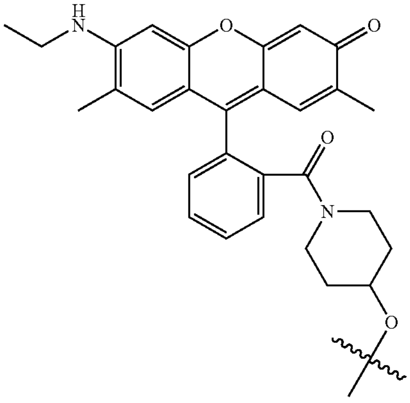
;
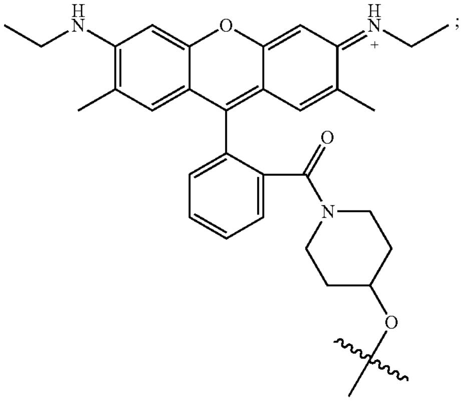
;

-continued

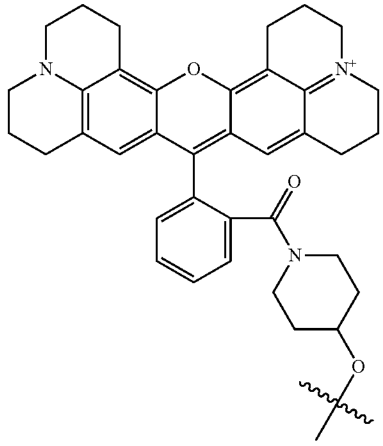

;

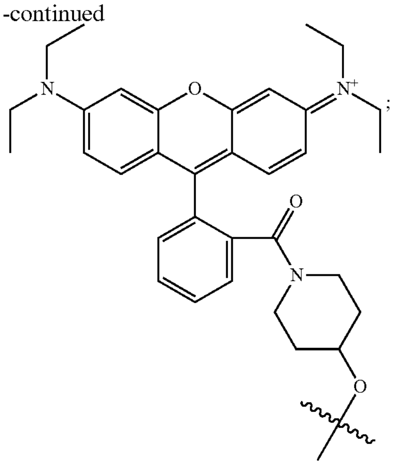

;

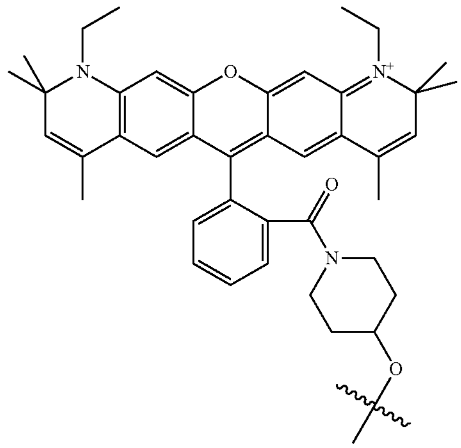

or

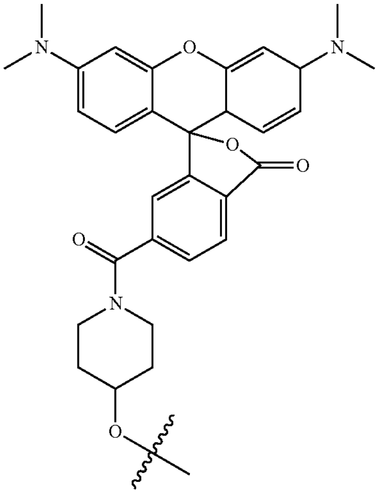

.

In some specific embodiments, the compound is a compound selected from Table 2. The compounds in Table 2 were prepared according to the procedures set forth in the Examples and using techniques known in the art (e.g., automated DNA synthesis) and their identity confirmed by mass spectrometry.

TABLE 2

Exemplary Compounds of Structure I

| No. | MW. Found Calc. | Structure |
|---|---|---|
| I-1 | 15623.0<br>15619.5 | 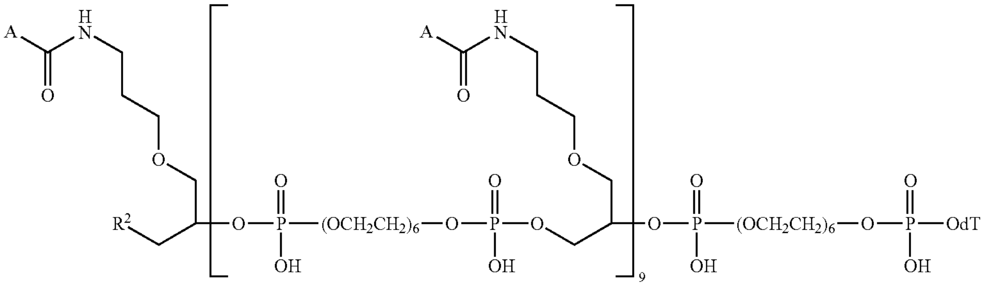<br>$R^2$ = 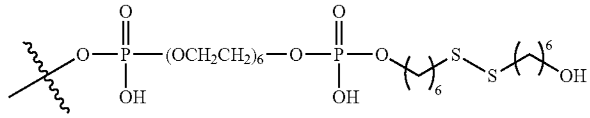 |

TABLE 2-continued
Exemplary Compounds of Structure I
| No. | MW. Found Calc. | Structure |
| --- | --- | --- |
| I-2 | 8078.0 (avg) 8083.8 (avg) | 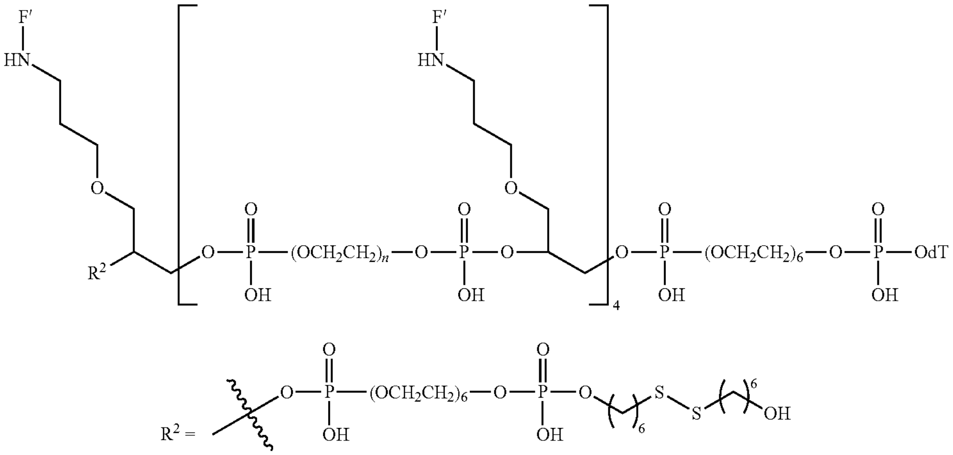 n = 22-26 |
| I-3 | 7408.0 (avg) 7410.8 (avg) | 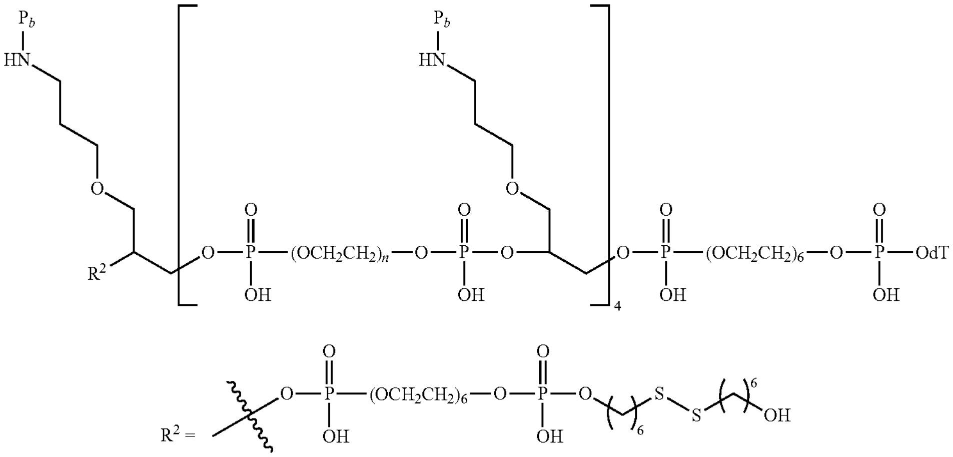 n = 22-26 |
| I-4 | 8906.2 (avg) 8903 (avg) | 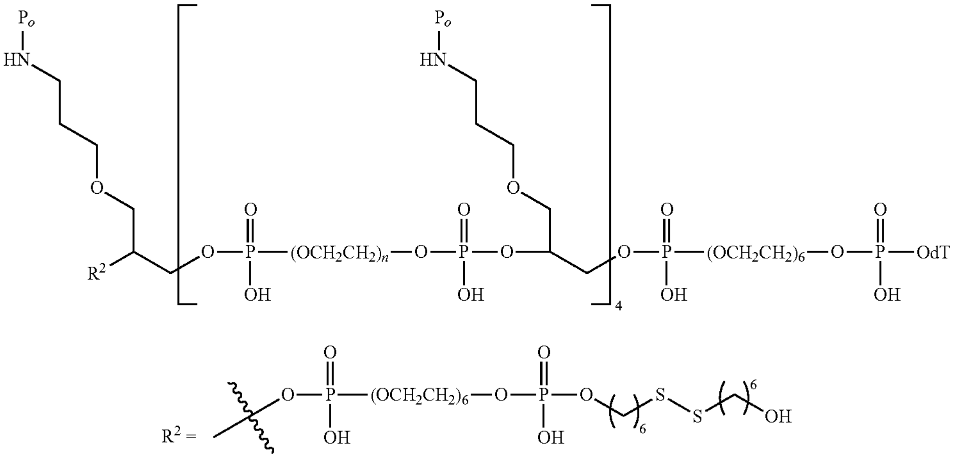 n = 22-26 |

TABLE 2-continued
Exemplary Compounds of Structure I
| No. | MW. Found Calc. | Structure |
|---|---|---|
| I-5 | 8874.0 (avg) 8873.8 (avg) | 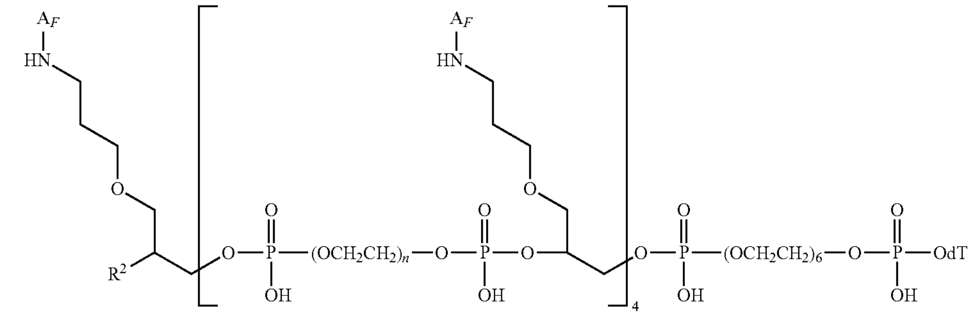<br>$R^2$ = 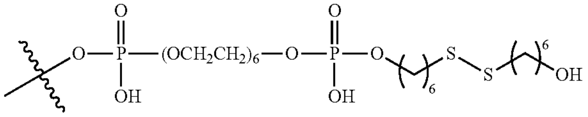<br>n = 22-26 |
| I-6 | 7771.7 (avg) 7770.0 (avg) | 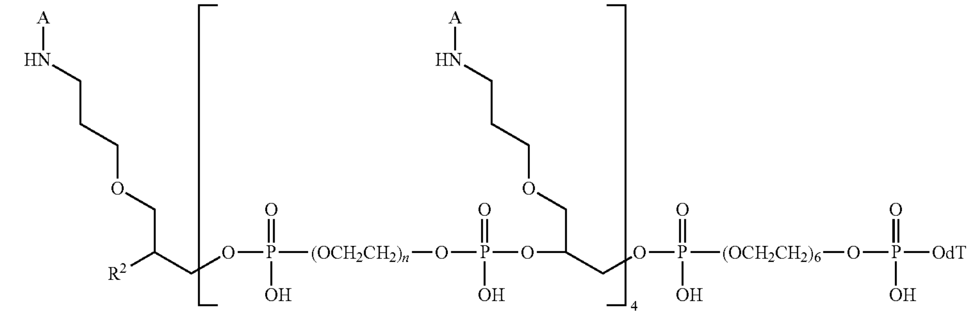<br>$R^2$ = 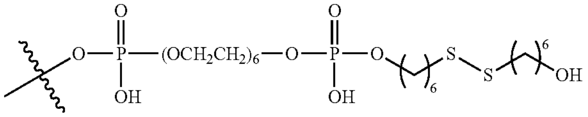<br>n = 22-26 |
As used throughout the application F, F' and F" refer to a fluorescein moiety having the following structures, respectively:
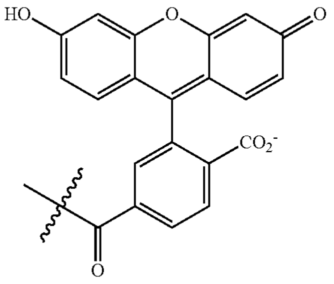
F
-continued
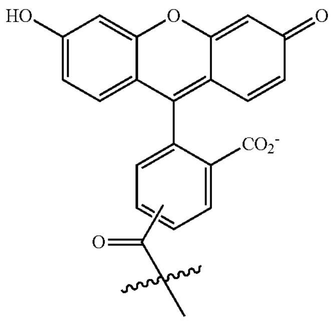
F'

-continued

F''

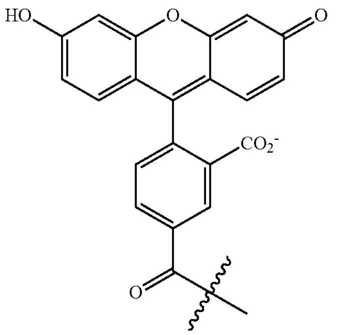

In some embodiments, $M^1$ or $M^2$ is, at one or more occurrences, independently F, F' or F''. It is well known in the art that fluorescein moieties tautomerize between quinoid, zwitterionic, and lactoid forms. Although the structures above are depicted as having a —$CO_2^-$ moiety, one of skill in the art will readily understand that the form is dependent on pH and each form (e.g., quinoid, zwitterionic, and lactoid) are also included in the scope of embodiments of the invention.

As used throughout this disclosure dT refers to the following structure:

dT

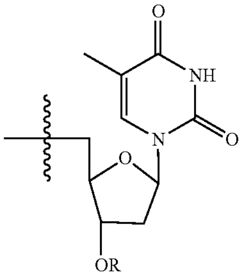

wherein:

R is H or a direct bond. In some embodiments, $R^1$ or $R^2$ comprises dT. In more specific embodiments, $R^1$ comprises dT. In some embodiments, $R^2$ comprises dT.

As used throughout this disclosure, B and B' refer to the following structures, respectively:

B

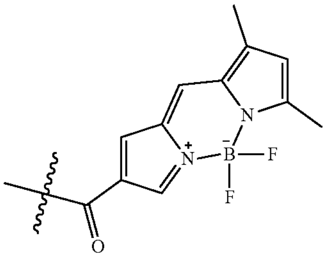

-continued

B'

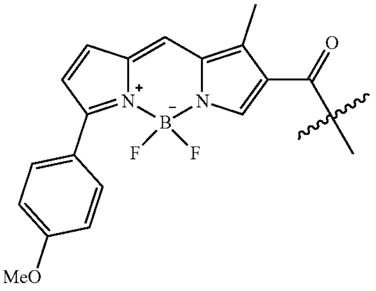

In some embodiments, $M^1$ or $M^2$ is, at one or more occurrences, independently B or B'. In certain embodiments, $M^1$ is, at each occurrence, independently B or B'. In some embodiments, $M^2$ is, at each occurrence, independently B or B'.

As used throughout this disclosure, T refers to the following structure:

T

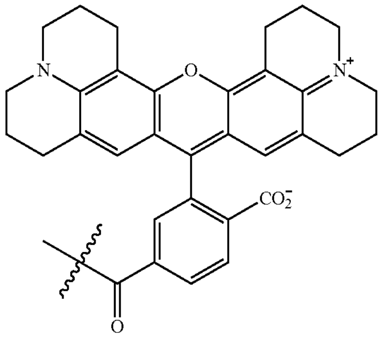

In specific embodiments, $M^1$ or $M^2$ is, at one or more occurrences, independently T. In certain embodiments, $M^1$ is, at each occurrence, independently T. In some embodiments, $M^2$ is, at each occurrence, independently T.

As used throughout this disclosure, C refers to the following structure:

C

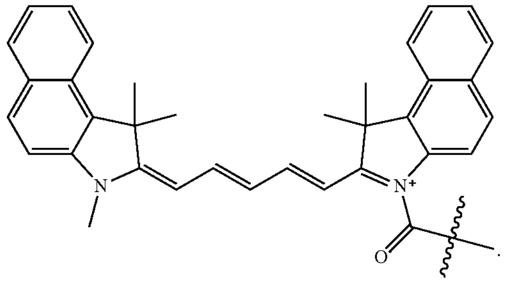

In some embodiments, $M^1$ or $M^2$ is, at one or more occurrences, independently C. In certain embodiments, $M^1$ is, at each occurrence, independently C. In some embodiments, $M^2$ is, at each occurrence, independently C.

As used throughout this disclosure, Y refers to the following structure:

Y

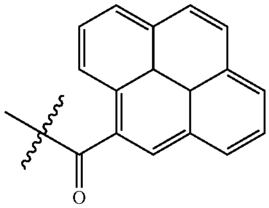

In some embodiments, $M^1$ or $M^2$ is, at one or more occurrences, independently Y. In certain embodiments, $M^1$ is, at each occurrence, independently Y. In some embodiments, $M^2$ is, at each occurrence, independently Y.

As used throughout this disclosure, A refers to the following structure:

A

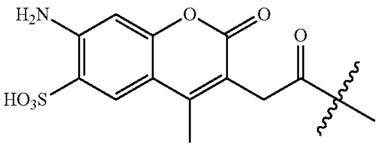

In some embodiments, $M^1$ or $M^2$ is, at one or more occurrences, independently A. In certain embodiments, $M^1$ is, at each occurrence, independently A. In some embodiments, $M^2$ is, at each occurrence, independently A.

As used throughout this disclosure, $P_b$ refers to the following structure:

$P_b$

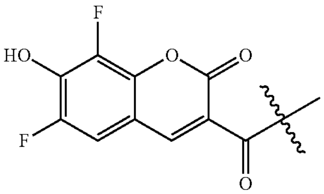

In some embodiments, $M^1$ or $M^2$ is, at one or more occurrences, independently $P_b$. In certain embodiments, $M^1$ is, at each occurrence, independently $P_b$. In some embodiments, $M^2$ is, at each occurrence, independently $P_b$.

As used throughout this disclosure, $P_0$ refers to the following structure:

$P_o$

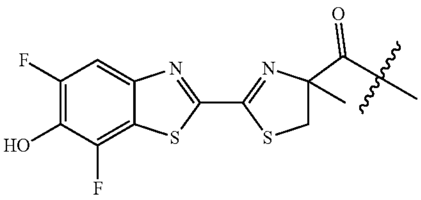

In some embodiments, $M^1$ or $M^2$ is, at one or more occurrences, independently $P_o$. In certain embodiments, $M^1$ is, at each occurrence, independently $P_o$. In some embodiments, $M^2$ is, at each occurrence, independently $P._o$ As used throughout this disclosure, $A_F$ refers to the following structure:

$A_F$

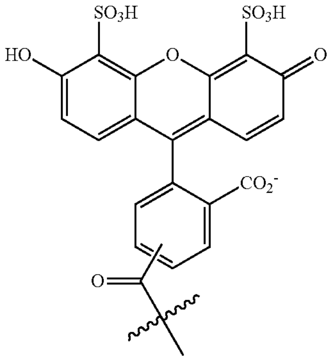

In some embodiments, $M^1$ or $M^2$ is, at one or more occurrences, independently $A_F$. In certain embodiments, $M^1$ is, at each occurrence, independently $A_F$. In some embodiments, $M^2$ is, at each occurrence, independently $A_F$.

Some embodiments include any of the foregoing compounds, including the specific compounds provided in Table 2, conjugated to a targeting moiety, such as an antibody.

The present disclosure generally provides compounds having increased fluorescence emission relative to earlier known compounds. Accordingly, certain embodiments are directed to a fluorescent compound comprising n' fluorescent moieties $M^1$ and/or $M^2$, wherein the fluorescent compound has a peak fluorescence emission upon excitation with a predetermined wavelength of ultraviolet light of at least 85% of n' times greater than the peak fluorescence emission of a single $M^1$ or $M^2$ moiety upon excitation with the same wavelength of ultraviolet light, and wherein n' is an integer of 2 or more. Fluorescent compounds include compounds which emit a fluorescent signal upon excitation with light, such as ultraviolet light.

In some embodiments, the fluorescent compound has a peak fluorescence emission of at least 90% of n' times greater, 95% of n' times greater, 97% of n' times greater or 99% of n' times greater than the peak fluorescence emission of a single $M^1$ and/or $M^2$ moiety.

In some embodiments, n' is an integer from 2 to 100, for example 2-10.

In some embodiments, the n' $M^1$ and/or $M^2$ moieties have, independently, one of the following structures:

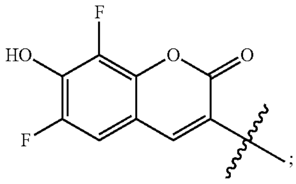

;

-continued
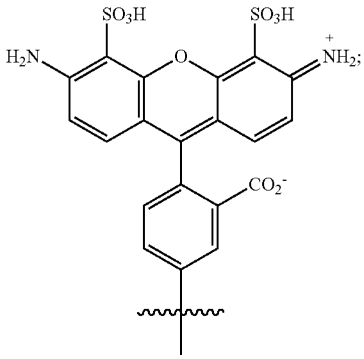
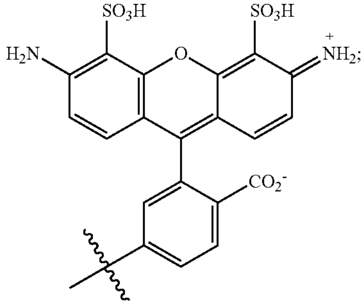
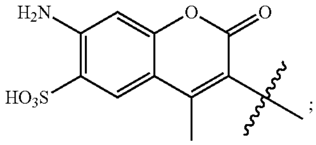
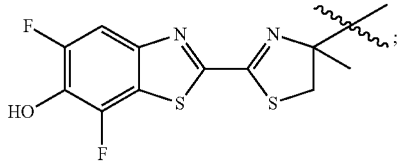
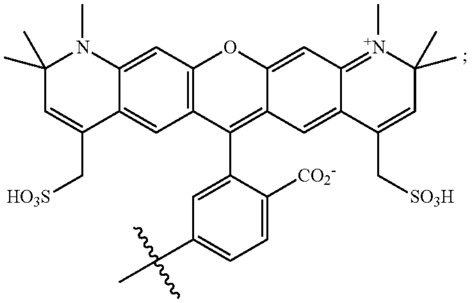
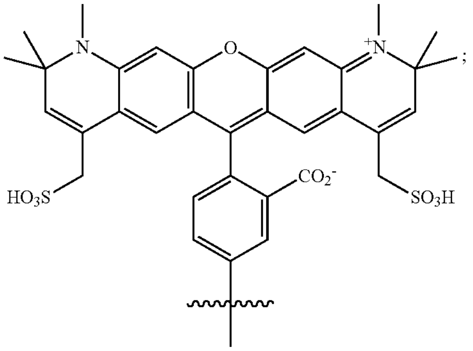
-continued
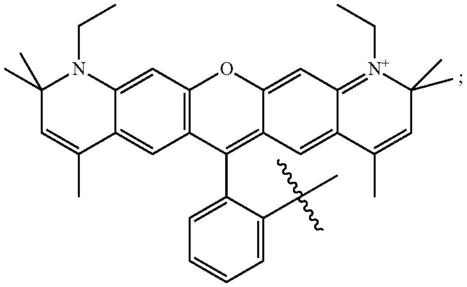
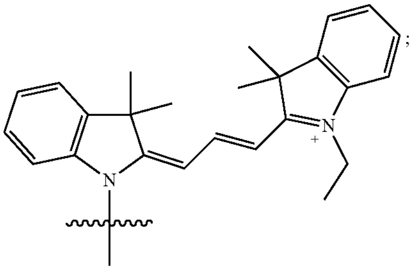
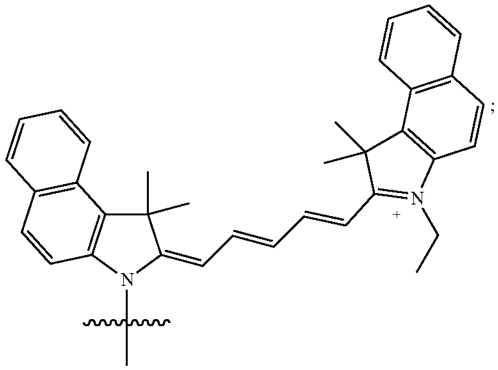
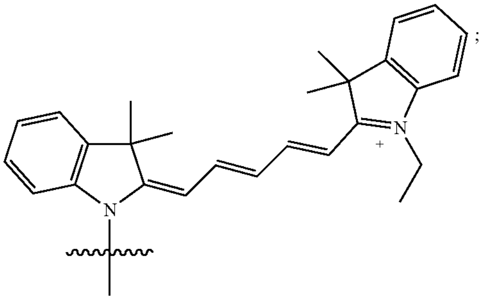
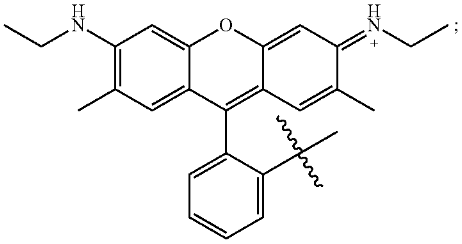
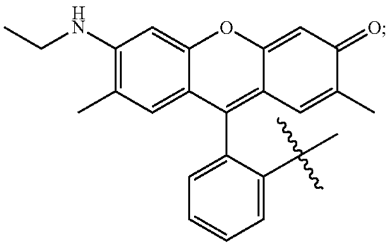

-continued
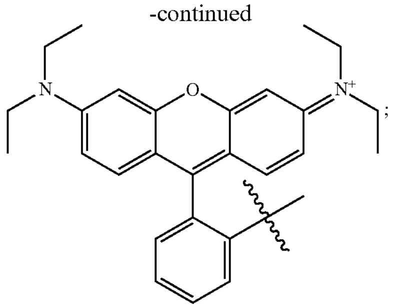
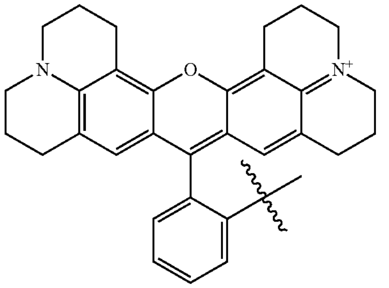
or
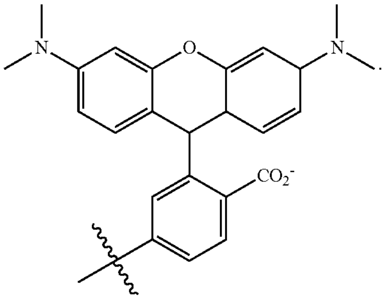
In other embodiments, the single $M^1$ or $M^2$ moiety has, independently, one of the following structures:
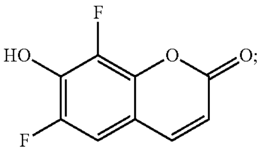
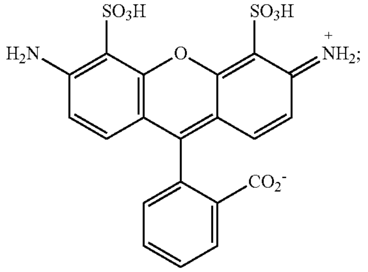
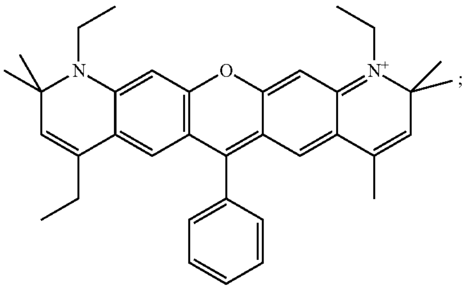
-continued
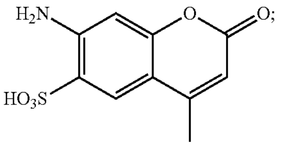
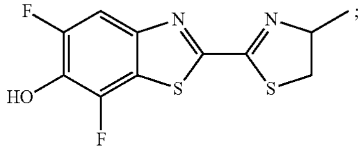
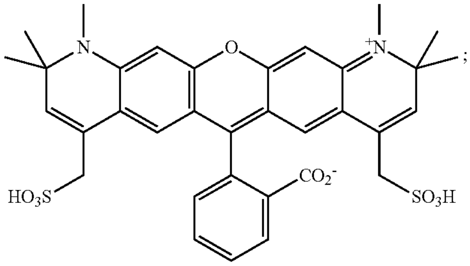
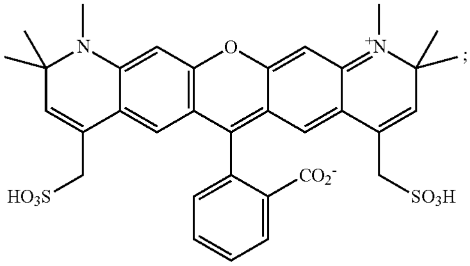
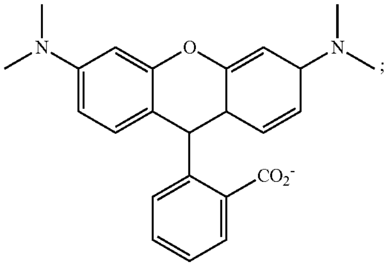
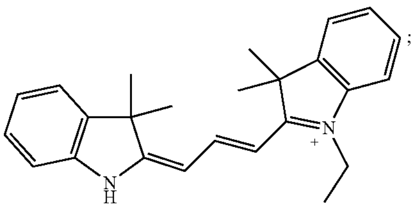
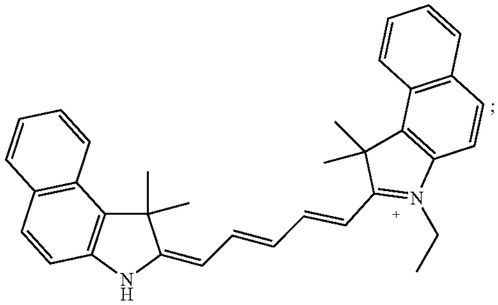

-continued
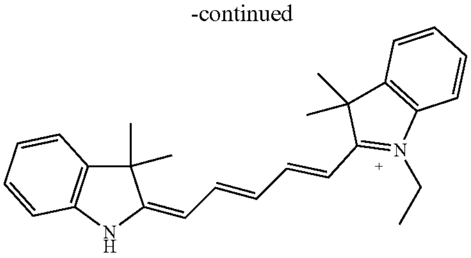
;
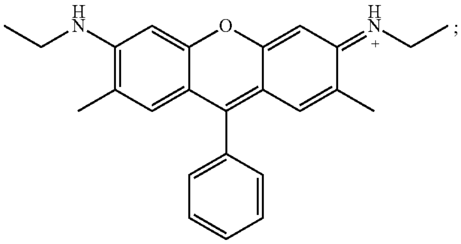
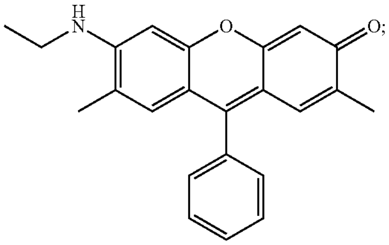
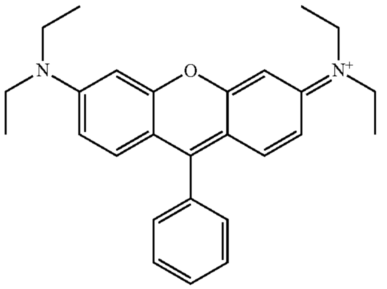
or
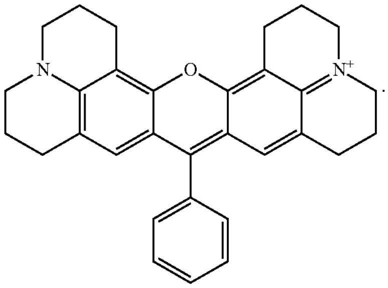
.
In some other embodiments, the n' $M^1$ and/or $M^2$ moieties have, at one or more occurrences, independently, one of the following structures:
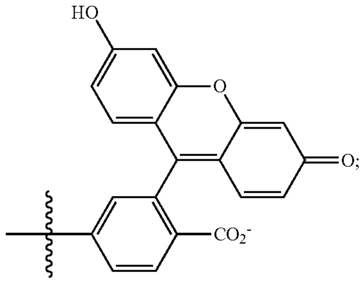
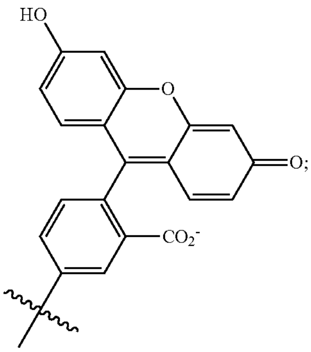
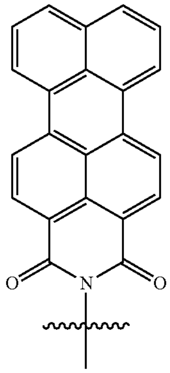
;
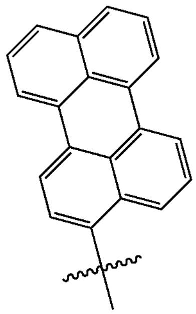
;
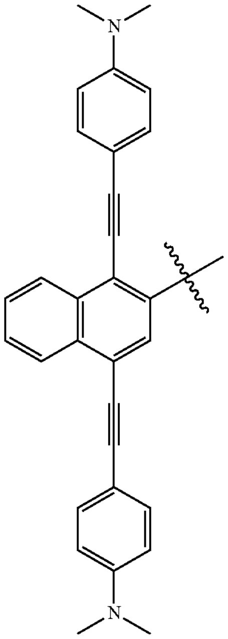
;

-continued

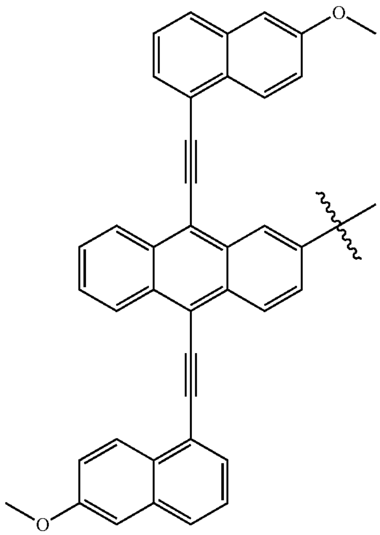

or

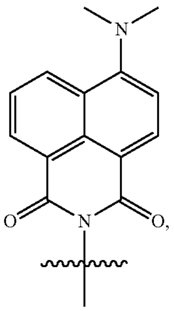

wherein  indicates a point of attachment to the fluorescent compound.

In other embodiments, the single $M^1$ or $M^2$ moiety has, independently, one of the following structures:

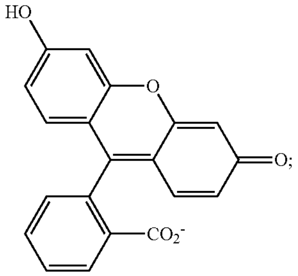

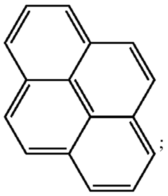

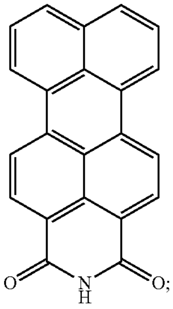

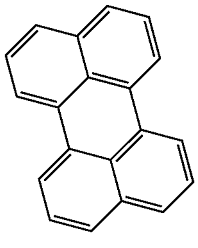

;

-continued

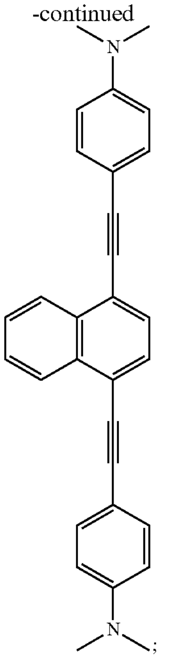

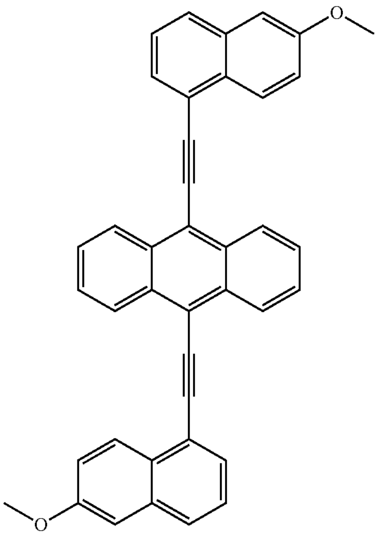

or

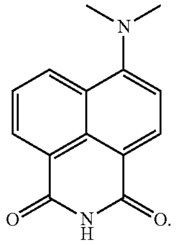 [SMILES: CN(C)c1ccc2c3c(cccc13)C(=O)NC2=O]

In other embodiments, the single $M^1$ or $M^2$ moiety has, independently, one of the following structures:

In still more embodiments, the fluorescent compound comprises at least one ethylene oxide moiety. Compositions comprising the fluorescent compound of any one of claims and an analyte are also provided.

The presently disclosed compounds are "tunable," meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of $L^{1a}$, $L^{1b}$, $L^2$, $L^3$, $L^4$, $L^5$, $L^6$, $L^7$, $M^1$, $M^2$, q, w, m and n is believed to play an important role in the molar fluorescence of the compounds. Accordingly, in one embodiment is provided a method for obtaining a compound having a desired molar fluorescence, the method comprising selecting $M^1$ or $M^2$ moieties having a known fluorescence, preparing a compound of structure (I) comprising the $M^1$ or $M^2$ moieties, and selecting the appropriate variables for $L^{1a}$, $L^{1b}$, $L^2$, $L^3$, $L^4$, $L^5$, $L^6$, $L^7$, $M^1$, $M^2$, q, w, m and n to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9×, 10× or even higher relative to the parent fluorophore. Various embodiments include preparing compounds having the desired fold increase in fluorescence relative to the parent fluorophore by proper selection of $M^1$, $M^2$, $L^{1a}$, $L^{1b}$, $L^3$, $L^4$, q, w, m and n.

For ease of illustration, various compounds comprising phosphorous moieties (e.g., phosphate and the like) are depicted in the anionic state (e.g., $-OPO(OH)O^-$, $-OPO_3^{2-}$). One of skill in the art will readily understand that the charge is dependent on pH and the uncharged (e.g., protonated or salt, such as sodium or other cation) forms are also included in the scope of embodiments of the invention.

Compositions comprising any of the foregoing compounds (e.g., a compound of structure (I)) and one or more analyte molecules (e.g., biomolecules) are provided in various other embodiments. In some embodiments, use of such compositions in analytical methods for detection of the one or more analyte molecules is also provided.

Methods

In still other embodiments, the compounds are useful in various analytical methods. For example, in certain embodiments the disclosure provides a method of staining a sample, the method comprising adding to said sample a compound of structure (I), for example wherein one of $R^1$ or $R^2$ is a linker comprising a covalent bond to an analyte molecule (e.g., biomolecule) or microparticle, and the other of $R^1$ or $R^2$ is H, OH, alkyl, alkoxy, alkylether or $-OP(=R_a)(R_b)R_c$, in an amount sufficient to produce an optical response when said sample is illuminated at an appropriate wavelength.

In some embodiments of the foregoing methods, $R^1$ is a linker comprising a covalent linkage to an analyte molecule, such as a biomolecule. For example, in some embodiments the biomolecule is a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^1$ is a linker comprising a covalent linkage to a solid support such as a microparticle. For example, in some embodiments the microparticle is a polymeric bead or non-polymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:

(a) providing a compound of structure (I), for example, wherein one of $R^1$ or $R^2$ is a linker comprising a covalent bond to the analyte molecule, and the other of $R^1$ or $R^2$ is H, OH, alkyl, alkoxy, alkylether or $-OP(=R_a)(R_b)R_c$; and (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:

(a) admixing any of the foregoing compounds with one or more analyte molecules; and (b) detecting the compound by its visible properties.

In other embodiments is provided a method for visually detecting an analyte molecule, the method comprising:

(a) admixing the compound of structure (I), wherein $R^1$ or $R^2$ is Q or a linker comprising a covalent bond to Q, with the analyte molecule;

(b) forming a conjugate of the compound and the analyte molecule; and (c) detecting the conjugate by its visible properties.

Other exemplary methods include a method for detecting an analyte, the method comprising:

(a) providing a compound of structure (I), wherein $R^1$ or $R^2$ comprises a linker comprising a covalent bond to a targeting moiety having specificity for the analyte;

(b) admixing the compound and the analyte, thereby associating the targeting moiety and the analyte; and (c) detecting the compound, for example by its visible or fluorescent properties.

In certain embodiments of the foregoing method, the analyte is a particle, such as a cell, and the method includes use of flow cytometry. For example, the compound may be provided with a targeting moiety, such as an antibody, for selectively associating with the desired cell, thus rendering the cell detectable by any number of techniques, such as visible or fluorescence detection. Appropriate antibodies can be selected by one of ordinary skill in the art depending on the desired end use. Exemplary antibodies for use in certain embodiments include UCHT-1 and MOPC-21.

Embodiments of the present compounds thus find utility in any number of methods, including, but not limited: cell counting; cell sorting; biomarker detection; quantifying apoptosis; determining cell viability; identifying cell surface antigens; determining total DNA and/or RNA content; identifying specific nucleic acid sequences (e.g., as a nucleic acid probe); and diagnosing diseases, such as blood cancers.

In addition to the above methods, embodiments of the compounds of structure (I) find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by including a targeting moiety, such as an antibody or sugar or other moiety that preferentially binds cancer cells, in a compound of structure (I) to; imaging in surgical procedures; binding of histones for identification of various diseases; drug delivery, for example by replacing the $M^1$ or $M^2$ moieties in a compound of structure (I) with an active drug moiety; and/or contrast agents in dental work and other procedures, for example by preferential binding of the compound of structure (I) to various flora and/or organisms.

It is understood that any embodiment of the compounds of structure (I), as set forth above, and any specific choice set forth herein for a $R^1$, $R^2$, $R^3$, $R^4$, $R^5$, $L^{1a}$, $L^{1b}$, $L^2$, $L^3$, $L^4$, $L^5$, $L^6$, $L^7$, $M^1$, $M^2$, q, w, m and/or n variable in the compounds of structure (I), as set forth above, may be independently combined with other embodiments and/or variables of the compounds of structure (I) to form embodiments of the invention not specifically set forth above. In addition, in the event that a list of choices is listed for any particular $R^1$, $R^2$, $R^3$, $R^4$, $R^5$, $L^{1a}$, $L^{1b}$, $L^2$, $L^3$, $L^4$, $L^5$, $L^6$, $L^7$, $M^1$, $M^2$, q, w, m and/or n variable in a particular embodiment and/or claim, it is understood that each individual choice may be deleted from the particular embodiment and/or claim and that the remaining list of choices will be considered to be within the scope of the invention.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Furthermore, all compounds of the invention which exist in free base or acid form can be converted to their salts by treatment with the appropriate inorganic or organic base or acid by methods known to one skilled in the art. Salts of the compounds of the invention can be converted to their free base or acid form by standard techniques.

The following Reaction Schemes illustrate exemplary methods of making compounds of this invention. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

REACTION SCHEME I

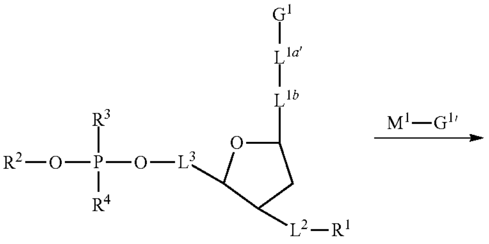

a

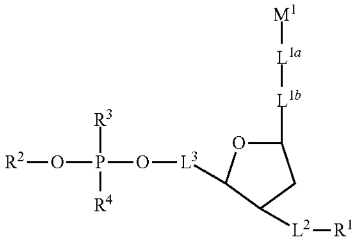

b

Reaction Scheme I illustrates a method for preparation of intermediates useful for preparation of compounds of structure (I). Referring to reaction Scheme I, wherein $L^{1a'}$, $L^{1a}$, $L^{1b}$, $L^2$, $L^3$, $G^1$ and $M^1$ are as defined above, and $R^1$ and $R^2$ are as defined above, or are protected variants thereof, a compound of structure a, which can be purchased or prepared by well-known techniques, is reacted with M-$G^{1'}$ to yield compounds of structure b. Here, $G^1$ and $G^{1'}$ represent functional groups having complementary reactivity (i.e., functional groups which react to form a covalent bond). $G^{1'}$ may be pendant to $M^1$ or a part of the structural backbone of $M^1$. $G^1$ and $G^{1'}$ may be any number of functional groups described herein, such as alkyne and azide, respectively, amine and activated ester, respectively or amine and isothiocyanate, respectively, and the like. $M^2$ can be attached to form a compound of structure (I) in an analogous manner by selecting appropriate reagents according to Reaction Scheme I above.

Additionally, compounds of the present disclosure can be prepared according to the methods described in PCT Pub. Nos. WO 2016/183185; WO 2017/173355; and WO 2017/177065, each of which are hereby incorporated by reference.

The compound of structure (I) may be prepared from structure b by reaction under well-known automated DNA synthesis conditions with a phosphoramidite compound having the following structure (c):

(c)

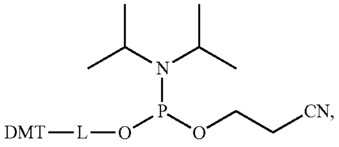

wherein L is an optional linker. DNA synthesis methods are well-known in the art. Briefly, two alcohol groups, for example $R^1$ and $R^2$ in intermediate b above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

For example, n some embodiments of (c), the linker L has one of the following structures:

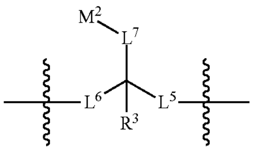

or

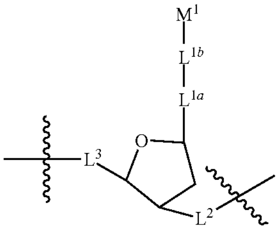

wherein:

$L^{1a}$ $L^{1b}$, $L^2$, $L^3$, $L^4$, $L^5$, $L^6$, $L^7$, $R^1$, $M^1$, and $M^2$ are as defined herein.

Preparation of the phosphoramidites used in the oligomerization methods is also well-known in the art. For example, a primary alcohol (e.g., $R^1$ in Reaction Scheme 1 above) can be protected as a DMT group by reaction with DMT-Cl. A secondary alcohol (e.g., $R^2$ in Reaction Scheme 1 above) is then functionalized as a phosphoramidite by reaction with an appropriate reagent such as 2-cyanoethyl N,N-dissopropylchlorophosphoramidite. Methods for preparation of phosphoramidites and their oligomerization are well-known in the art and described in more detail in the examples.

Compounds of structure (I) are prepared by oligomerization of intermediates b and c according to the well-known phophoramidite chemistry described above. The desired number of n repeating units is incorporated into the molecule by repeating the phosphoramidite coupling the desired number of times. It will be appreciated that compounds of structure (II) as, described below, can be prepared by analogous methods.

In various other embodiments, compounds useful for preparation of the compound of structure (I) are provided. The compounds can be prepared as described above in monomer, dimer and/or oligomeric form and then an $M^1$ and/or $M^2$ moiety covalently attached to the compound via any number of synthetic methodologies (e.g., the "click" reactions described above) to form a compound of structure (I). Accordingly, in various embodiments a compound is provided having the following structure (II):

(II)

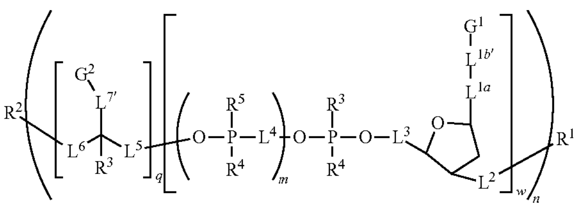

or a stereoisomer, salt or tautomer thereof, wherein:

G and $G^2$ are, at each occurrence, independently a moiety comprising a reactive group, or protected analogue thereof, capable of forming a covalent bond with a complementary reactive group;

$L^{1a}$ is at each occurrence, independently a heteroalkylene or heteroarylene linker;

$L^{1b'}$, $L^2$, $L^3$, $L^5$, $L^6$, and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^1$ and $R^2$ are each independently H, OH, SH, alkyl, alkoxy, alkylether, heteroalkyl, —OP(=$R_a$)($R_b$)$R_c$, Q, or a protected form thereof, or L';

$R^3$ is, at each occurrence, independently H, alkyl or alkoxy;

$R^4$ is, at each occurrence, independently OH, SH, $O^-$, $S^-$, $OR_d$ or $SR_d$;

$R^5$ is, at each occurrence, independently oxo, thioxo or absent;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, an integer of one or greater;

n is an integer of one or greater;

q and w are, at each occurrence, independently 0 or 1 provided that q and w are not both 0 at each occurrence.

In other embodiments of structure (II), $G^1$ and $G^2$ are, at each occurrence, independently a moiety comprising a reactive group capable of forming a covalent bond with a complementary reactive group.

The $G^1$ and $G^2$ moieties in the compound of structure (II) can be selected from any moiety comprising a group having the appropriate reactivity group for forming a covalent bond with a complementary group on an $M^1$ and/or $M^2$ moiety. In exemplary embodiments, the $G^1$ and $G^2$ moieties can be selected from any of the Q moieties described herein, including those specific examples provided in Table 1. In some embodiments, $G^1$ and $G^2$ at each occurrence, independently comprises a moiety suitable for reactions including: the copper catalyzed reaction of an azide and alkyne to form a triazole (Huisgen 1, 3-dipolar cycloaddition), reaction of a diene and dienophile (Diels-Alder), strain-promoted alkyne-nitrone cycloaddition, reaction of a strained alkene with an azide, tetrazine or tetrazole, alkene and azide [3+2]cycloaddition, alkene and tetrazine inverse-demand Diels-Alder, alkene and tetrazole photoreaction and various displacement reactions, such as displacement of a leaving group by nucleophilic attack on an electrophilic atom.

For example, in one embodiment provides a compound of structure II, for example wherein the compound has the following structure II-1:

II-1

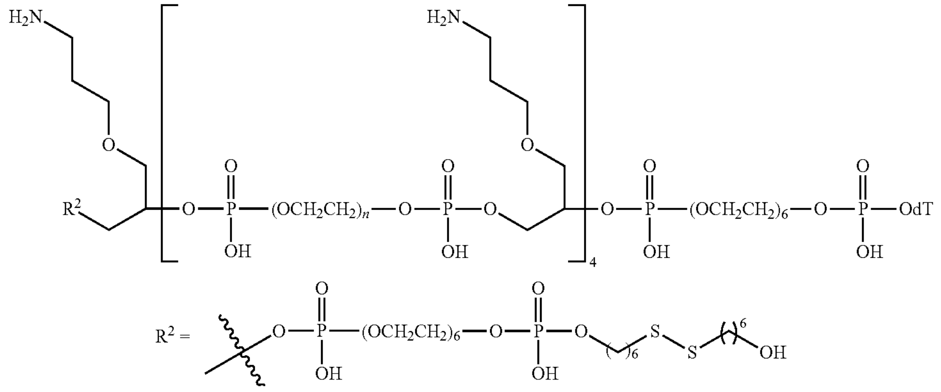

n = 22-26

In some embodiments, the average n is about 24. In some embodiments, the average n is about 25. In some embodiments, the average n is about 23.

In the foregoing embodiment, the compound of structure II can be reacted with one or more of the following compounds to afford a compound of structure I (e.g., a compound of structure I as shown in Table 2):

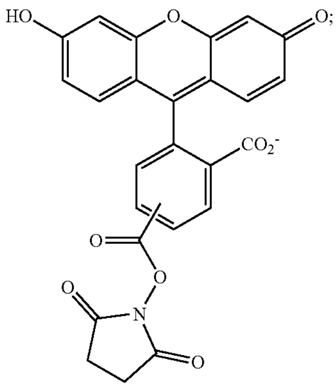

;

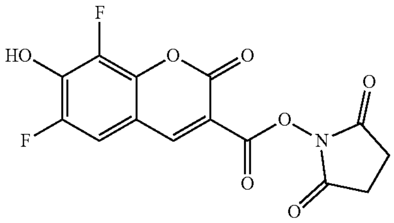

;

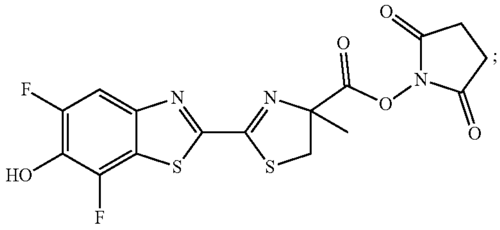

;

-continued

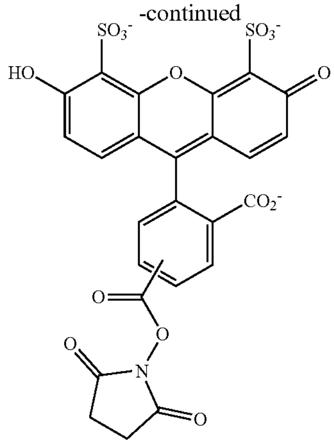

or

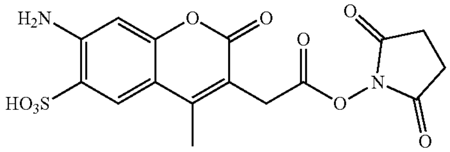

.

The following examples are provided for purposes of illustration, not limitation.

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HIP), 8.6 mM triethylamine (TEA), pH 8. Phosphoramidites and precursor molecules were also analyzed using a Waters Acquity UHPLC system with a 2.1 mm×50 mm Acquity BEH-$C_{18}$ column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, VA). Anhydrous pyridine, toluene, dichloromethane, diisopropylethyl amine, triethylamine, acetic acid, pyridine, and THE were purchased from Aldrich. All other chemicals were purchase from Aldrich or TCI and were used as is with no additional purification.

Example 1

Synthesis of Compound II-1

Solid Phase Synthesis

Compounds II-1 was prepared on the DNA synthesizer (AKTA OligoPilot 100) via solid support using standard DNA synthesis techniques (i.e., DMT protected 2-cyanoethyl phosphoramidite) on scales ranging from 14-200 μmol. The polymer was removed from the solid support with ammonium hydroxide (e.g., 28-30%, 3 hours at 55° C.) and lyophilized to a paste. The results of the synthesis are summarized in the table below:

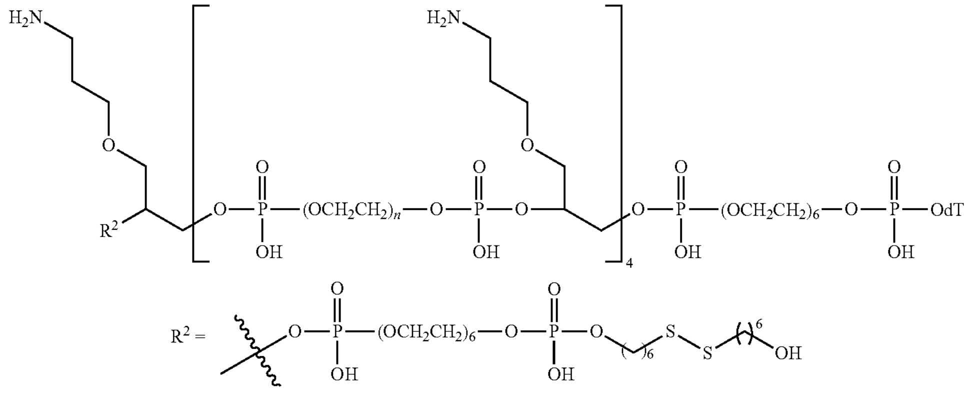

n = 22-26

Starting Materials

| | |
|---|---|
| DMT Hexaethoxy glycol phosphoramidite (HEG amidite) | 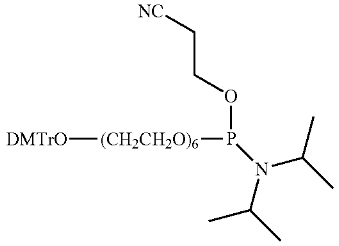 |
| Polyethyleneglycol 1000 CED Phosphoramidite PEG amidite) * length of PEG is approximately 25 and may vary | 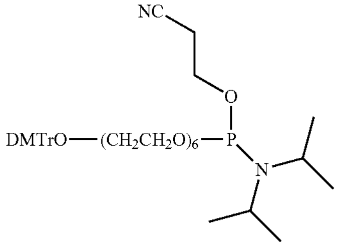 |
| Fmoc-Amino-DMT $C_7$ Phosphoramidite | 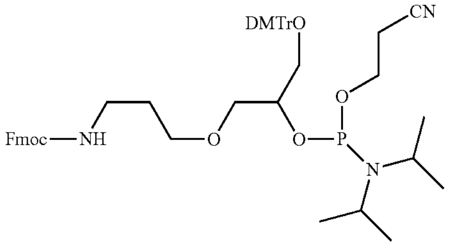 |

TABLE 3

| Results of synthesis of Compound II-1 | | | |
|---|---|---|---|
| Synthetic Scale (μmol) | Solid Support | MW Observed (Calculated) | Yield (%) |
| 14 | Controlled Pore Glass | 6291.7 (6159.3) | 63 |
| 150 | Controlled Pore Glass | 6291.7 (6159.3) | 53 |
| 30 | Polystyrene | 6293 (6159.3) | 70 |
| 200 | Polystyrene | 6292.8 (6159.3) | 85 |

Example 2

Synthesis of Compounds of Structure I

The compounds from Example 1 were coupled with desired dye molecules to afford compounds of structure I. With the Fmoc protecting group removed from the amine linker (e.g., using piperidine in DMF), Compound II-1 was then reacted with an appropriately activated dye molecule (i.e., NHS-ester). Reagents for the synthesis are prepared according to the following procedures.

Stock Solution Preparation

Borate buffer is prepared at 250 mM, pH 10

Dye-NHS solution prepared at 350 mM (300 mg in 1.35 mL DMSO:acetonitrile at 25:75)

Dye Coupling Reaction

In 50 mL centrifuge tube equipped with magnetic stir bar is placed water, borate buffer,

TABLE 4

| Results of synthesis of Compound II-1 | | |
|---|---|---|
| Compound | dye-NHS | Average MW Observed (Calculated)‡ |
| Compound I-2 | 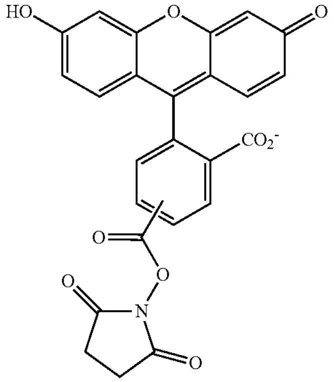 | 8083.8 (8078.0) |
| Compound I-3 | 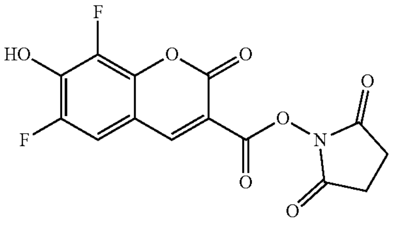 [SMILES: O=C(ON1C(=O)CCC1=O)c1cc2cc(F)c(O)c(F)c2oc1=O] | 7410.8 (7408.0) |
| Compound I-4 | 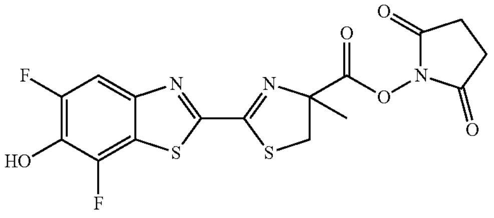 [SMILES: CC1(C(=O)ON2C(=O)CCC2=O)CSC(c2nc3cc(F)c(O)c(F)c3s2)=N1] | 8903 (8906.2) |

TABLE 4-continued

| Results of synthesis of Compound II-1 | | |
|---|---|---|
| Compound | dye-NHS | Average MW Observed (Calculated)‡ |
| Compound I-5 | 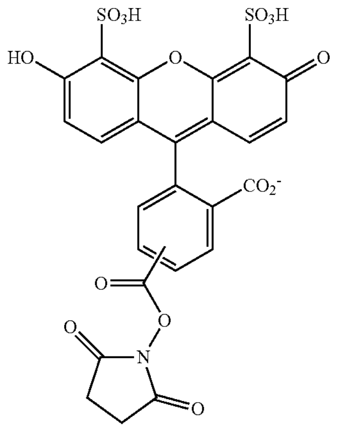 | 8873.8 (8874.0) |
| Compound I-6 | 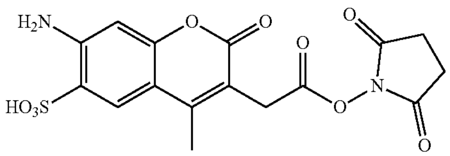 [SMILES: Cc1c(CC(=O)ON2C(=O)CCC2=O)c(=O)oc2cc(N)c(S(=O)(=O)O)cc12] | 7770.0 (7771.7) |

‡Reported MW values also shown in Table 2 with compound structures

Size Exclusion Filtration

To an Amicon Ultra-15 Centrifugal filter (Millipore UFC900324, MW cutoff=3000) is added 1 mL of water. The crude reaction from the dye coupling reaction (4.5 mL) is added to the filtration setup. The reaction vessel is rinsed 2× with 4 mL of 100 mM NaOH and the rinseates are transferred to the filtration setup. The filtration setup is centrifuged at max speed (3220 g, swing bucket, 30 minutes). The filtrate is removed and the retentate treated with an additional 10 mL of 100 mM NaOH. The filtration setup is centrifuged as before. Again, the filtrate is removed and a third 10 mL 100 mM NaOH aliquot is added to the retentate. The setup is centrifuged as before and the filtrate removed. A fourth 10 mL 100 mM NaOH aliquot is added to the retentate and centrifuged as before. The filtrate is removed and 10 mL of water are added to the filtration setup. The mixture is centrifuged as before. The retentate is removed, the filtration vessel washed with water and the rinesates added to the final volume (3.5 mL). The desired product was confirmed by LC-MS and absorbance is used to determine concentration.

Example 3

Activation and Antibody Conjugation of Structure I

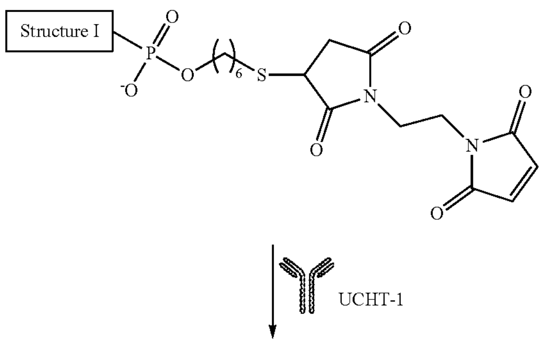

-continued

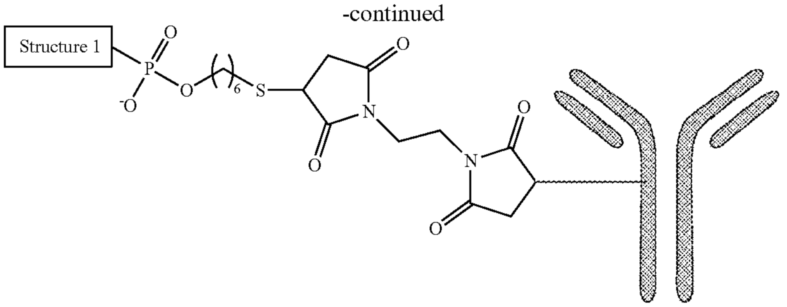

Representative compounds of structure I (i.e., Compounds I-1, I-2, I-3, I-4, I-5 and I-6) were prepared according to Example 2. The disulfide (i.e., moiety included in $R^2$ as shown in Table 2) was then reduced and functionalized with bis-maleimidoethane ("BMOE"). In parallel, an UCHT-1 antibody was reduced and coupled to the maleimidoethane functionalized compound of structure 1 as in the above reaction scheme in a 5:1 molar ratio of polymer to antibody. The reaction results in a final product having a polymer to antibody ratio of about 1:1 as detected by size exclusion chromatography.

Example 4

Flow Cytometry Method Using Antibody/Compound I

The antibody conjugates were prepared according to Example 3 for Compound I-1, I-2, I-4, I-5, and I-6. These antibody conjugates were then added to incubation buffer and diluted. A blood cell mixture (with CD3+ T-cells) was added to the diluted antibody/dye solution and the resultant solution was incubated for 45 minutes. Following incubation, a lyse-fix solution was added and the resultant mixture was incubated for 15 minutes at room temperature. Following incubation, the samples were centrifuged and washed (×2) and re-suspended. Samples contained reagent in excess when fixed, but is blocked by human plasma Ig and other proteins. The blood cell mixture contains cations, but is chelated using EDTA. The re-suspended mixture was then optionally stored overnight (at 4-8° C.). The samples were then agitated for approximately 45 minutes, followed by data acquisition.

Degree of labeling can be calculated according to the following equation:

$$\text{Brightness}=\varepsilon\times\lambda\times Q\times N_f$$

wherein ε is the molar absorptivity of the dye (or dye moiety), λ is the wavelength of excitation, Q is the quantum yield, and $N_f$ is the number of dye moieties present.

Figure 8:
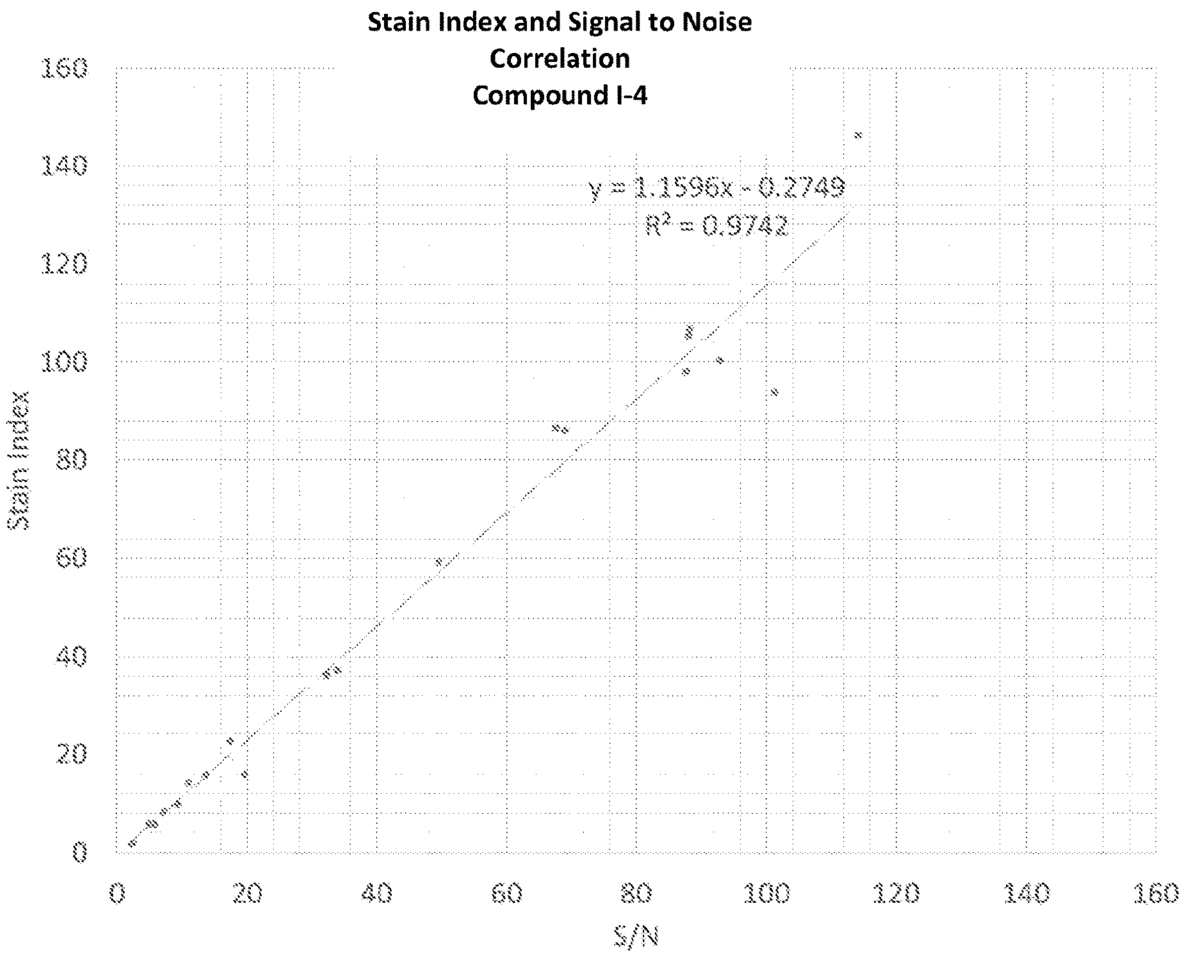
FIG. 8 illustrates the stain index correlation to a signal to noise reading for samples prepared using Compound I-4 (calculated from readings shown in FIG. 5).
Figure 9:
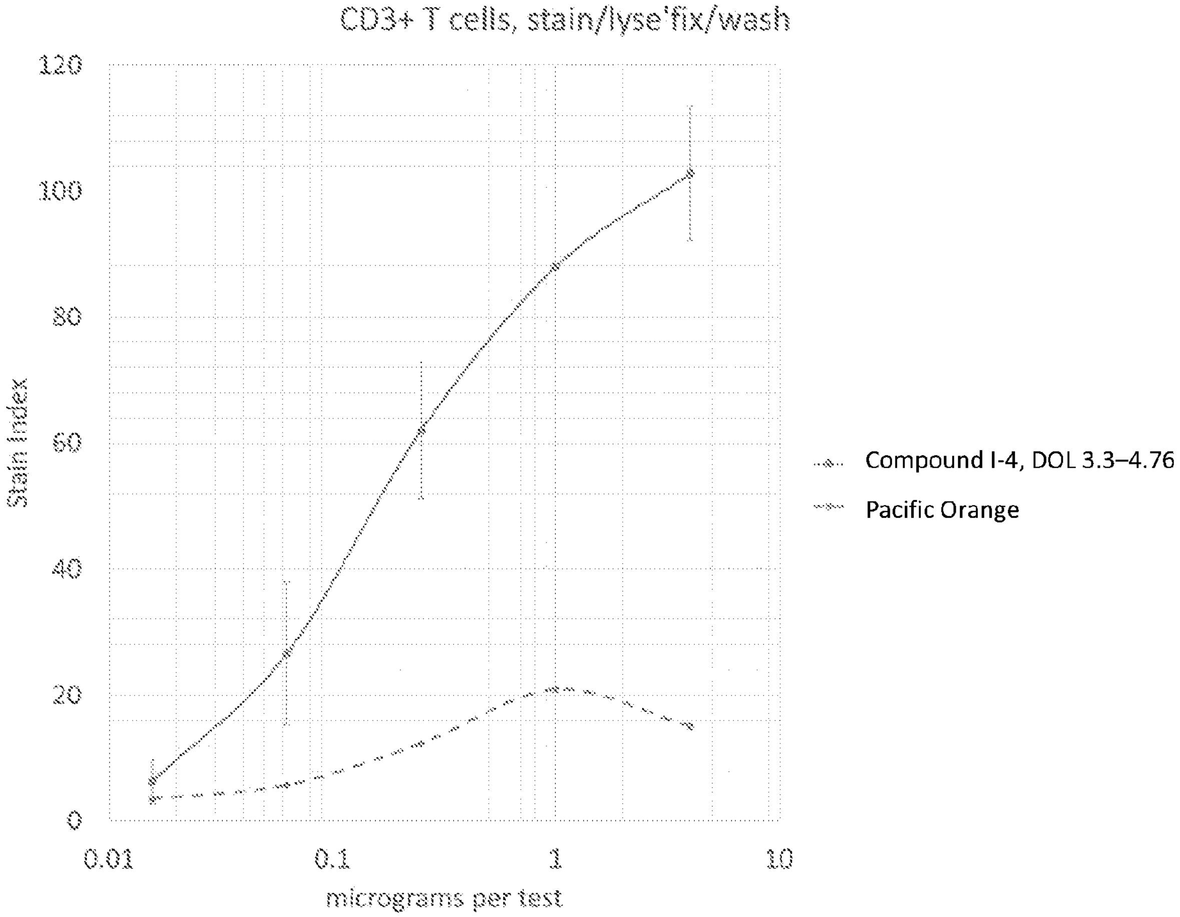
FIG. 9 shows an average stain index for samples prepared with Compound I-4 with DOL ranging from 3.3 to 4.76 compared to samples prepared with Pacific Orange alone.
Figure 10:
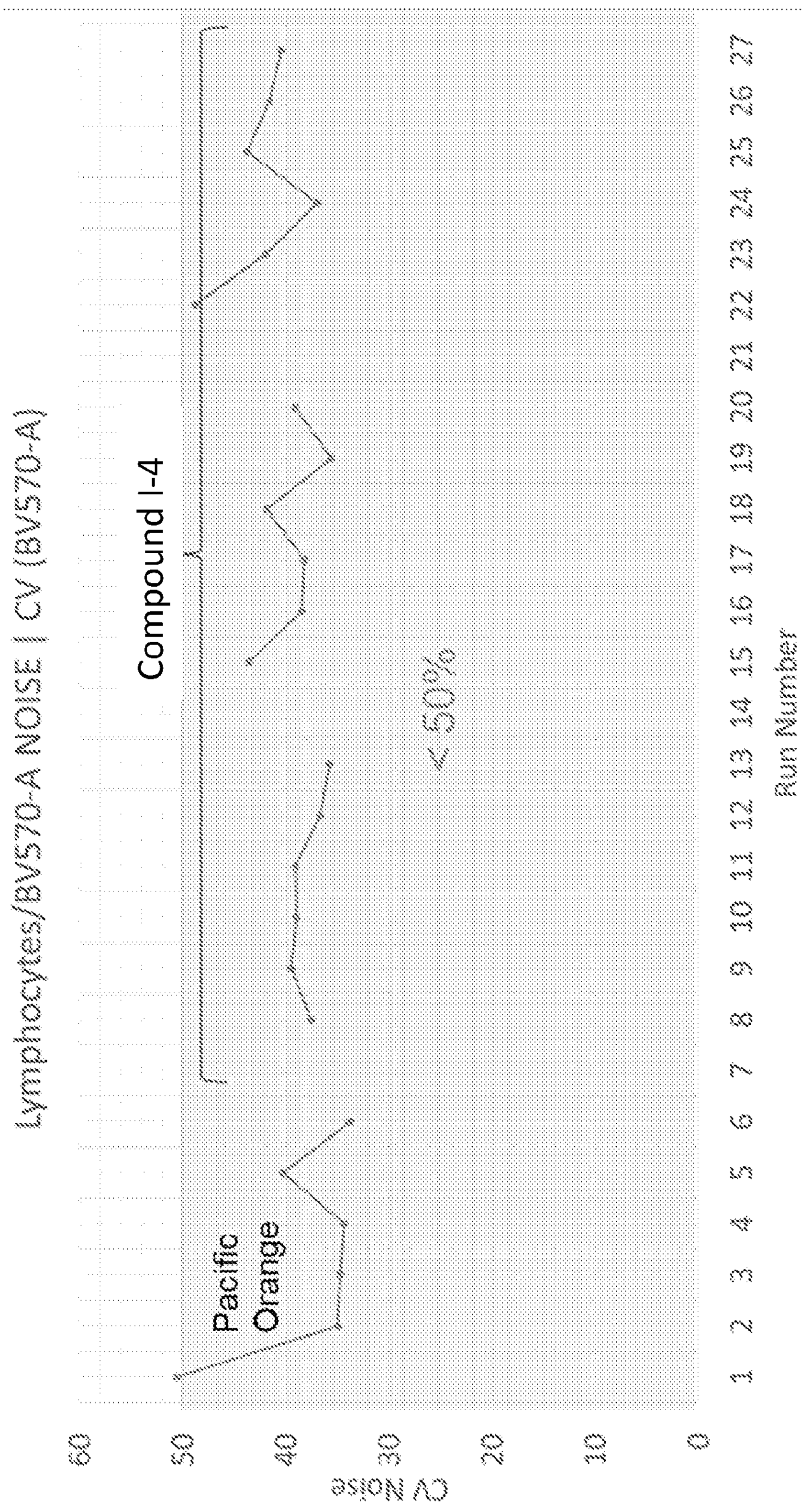
FIG. 10 is a plot of noise for samples prepared using Pacific Orange compared to Compound I-4 with DOL ranging from 3.3 to 4.76.
Figure 11:
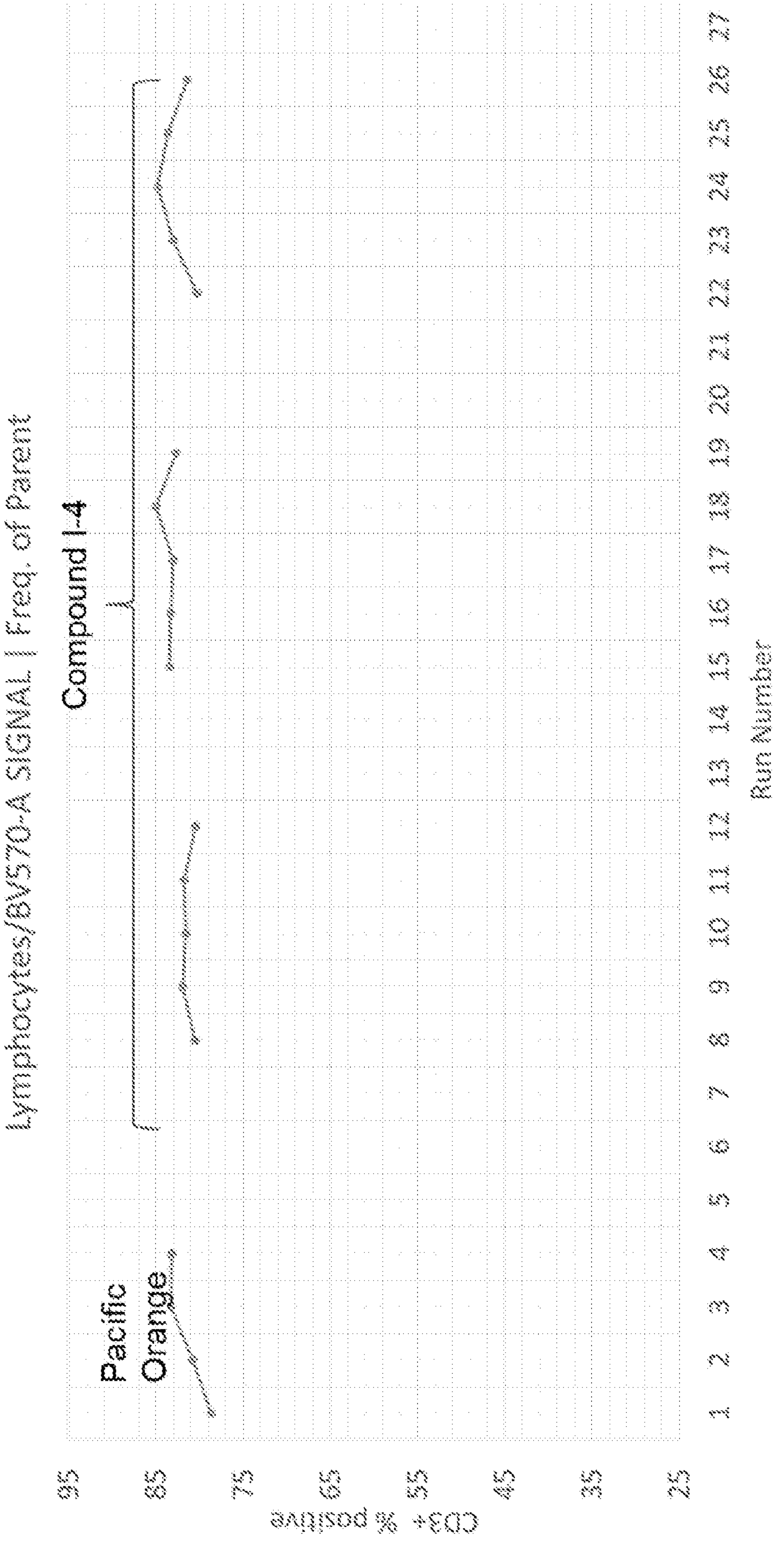
FIG. 11 is a plot of signal for samples prepared with Pacific Orange compared to Compound I-4 with DOL ranging from 3.3 to 4.76.

Readouts and representative data from flow cytometry experiments are found in FIGS. 5-27. As the data show, stain index is significantly improved for dye representative compounds of the present disclosure (e.g., Compound I-1, Compound I-2, Compound I-4, Compound I-5, and Compound I-6). There is also a strong correlation between stain index and signal to noise (see FIGS. 8, 22, and 27).

Compound I-4

Figure 5:
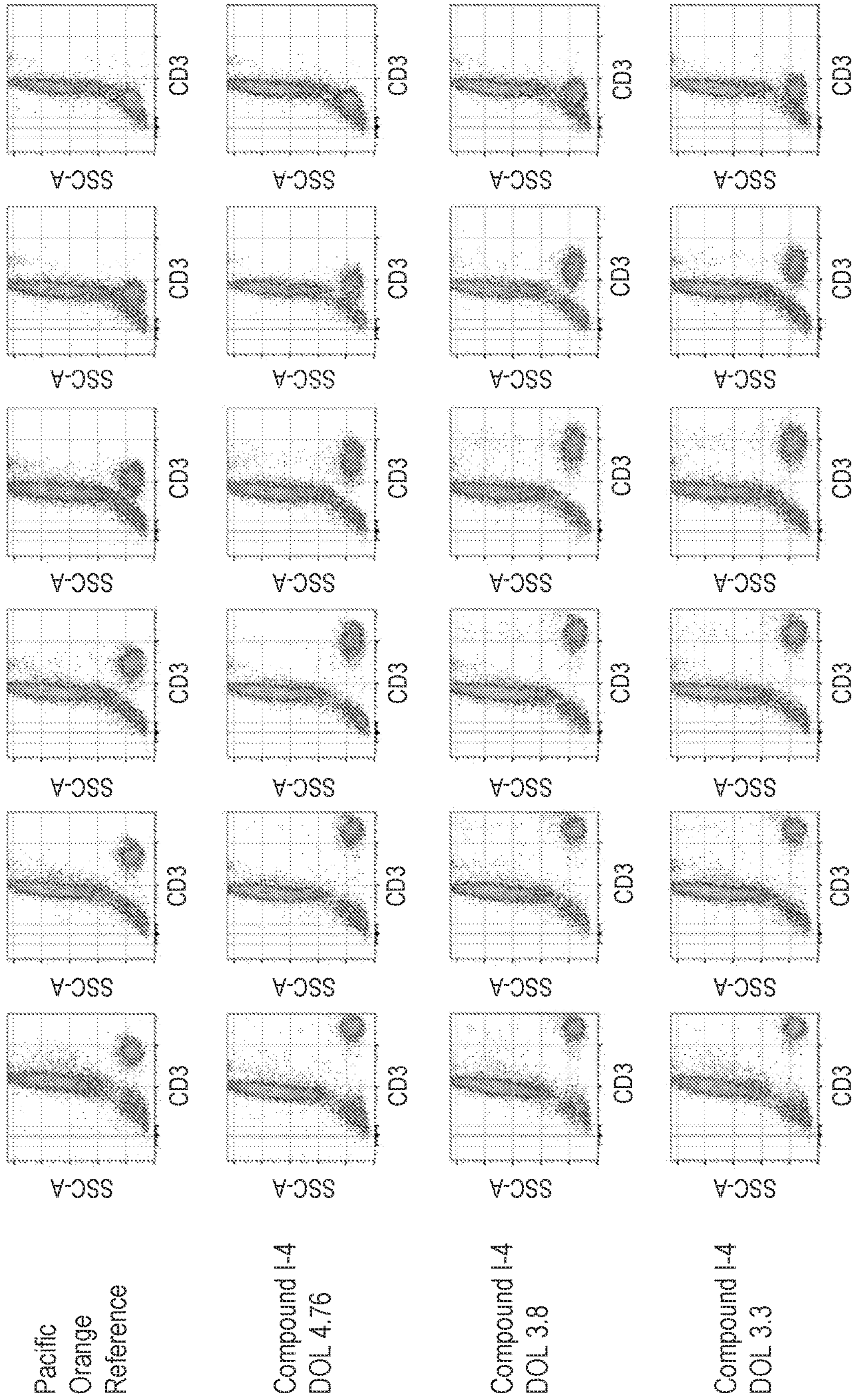
FIG. 5 shows representative flow cytometry readouts for samples prepared with a conjugates of UCHT-1 and Pacific Orange or Compound I-4 having a degree of labeling ("DOL") ranging from 3.3 to 4.76.
Figure 6:
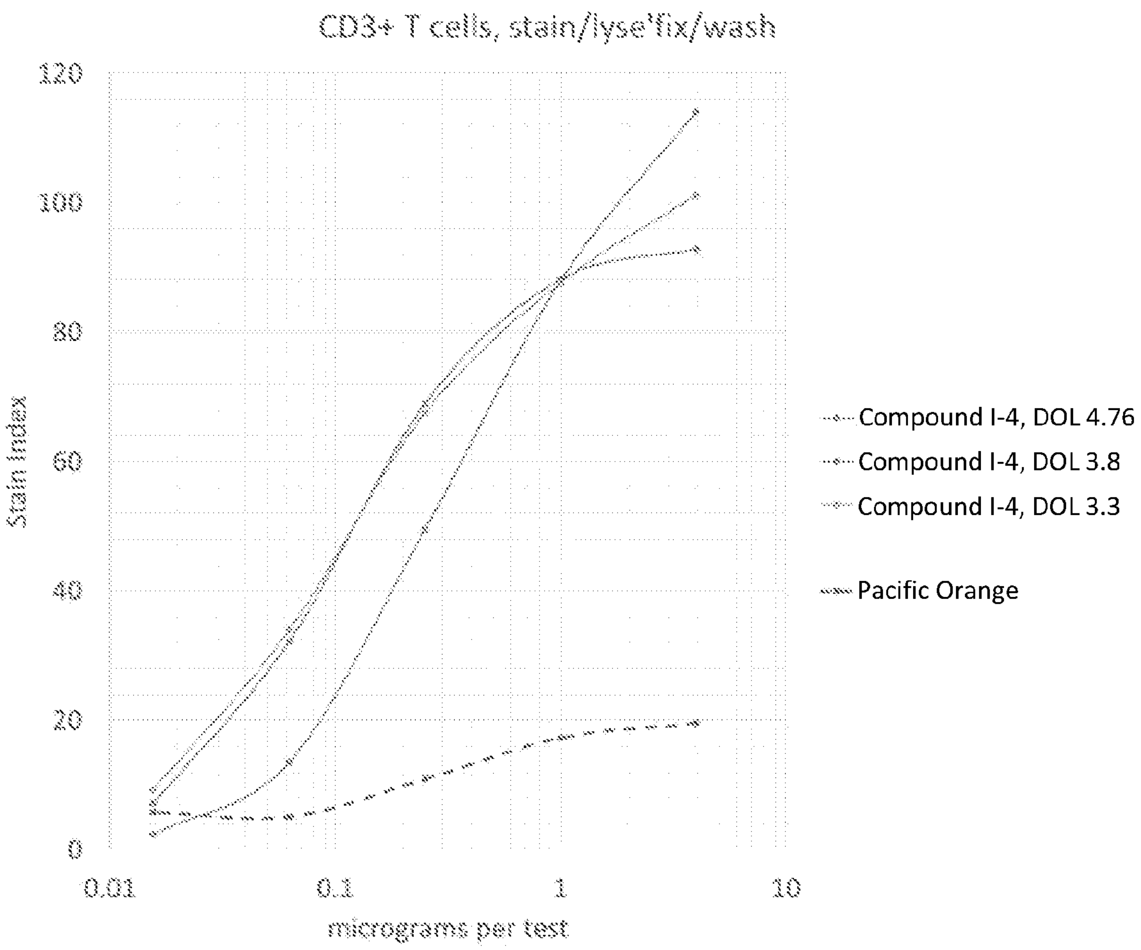
FIG. 6 is a plot of the stain index against the micrograms per test for a sample prepared using a Pacific Orange control and Compound I-4 having a DOL ranging from 3.3 to 4.76.
Figure 7:
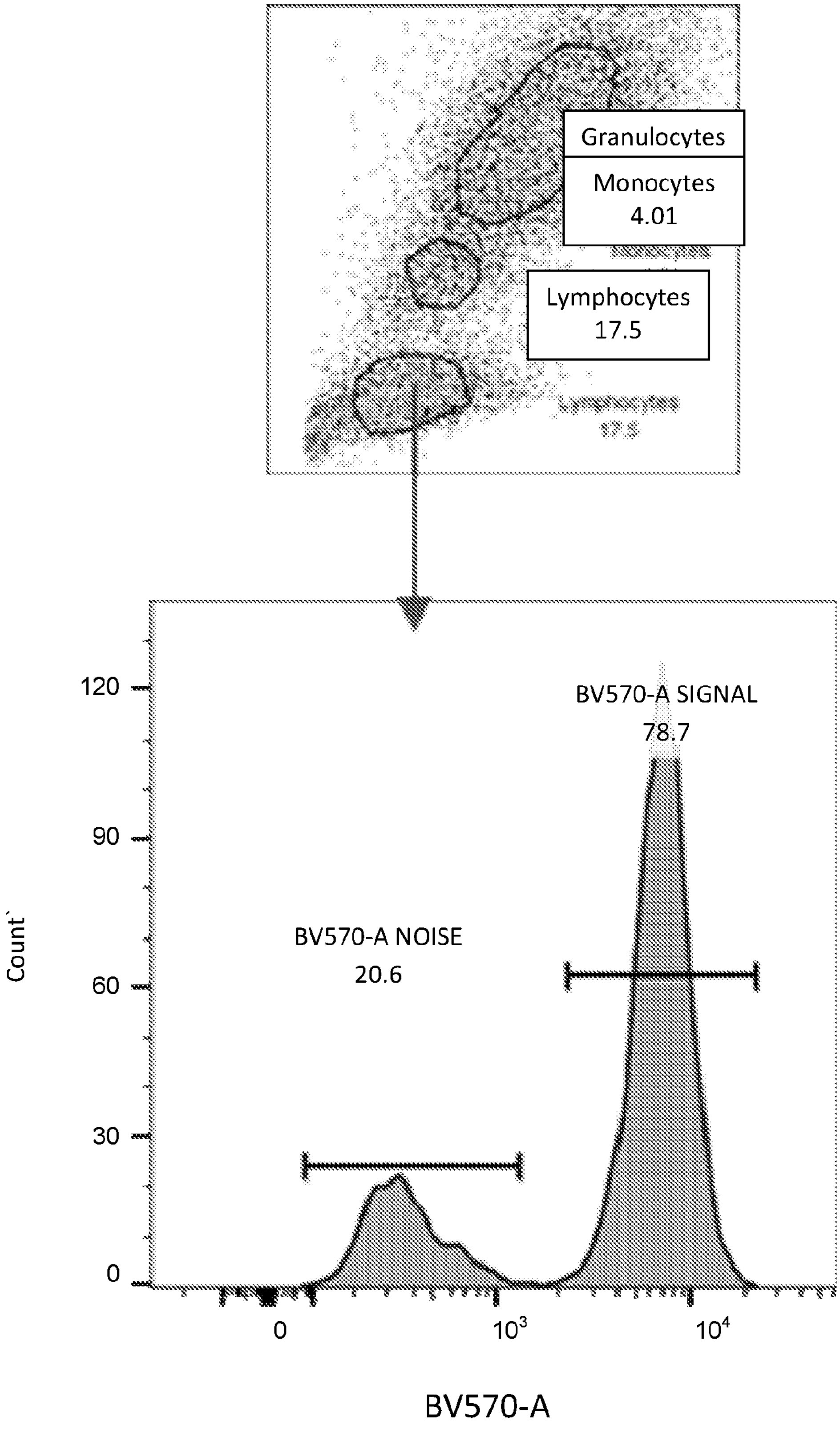
FIG. 7 shows populations of granulocytes, monocytes and lymphocytes and a representative plotting of signal to noise.

Data from FIG. 5 was acquired using 405 nm light and a band pass filter at 570 nm (emission max is 551 nm). A linear regression for the stain index correlation to the signal to noise showed an $R^2$ value of 0.9742. The mean and standard deviation shown in FIG. 9 (bars indicate 1 standard deviation from the mean) were calculating for n=3. Noise data (FIG. 10) indicates that the noise is similar to the Pacific Orange sample conjugate used as a reference and <50% like fluorescein-based dyes. The signal data (FIG. 11) indicates that the accuracy of labeling CD3 antigen is similar to the Pacific Orange conjugate used as a reference.

Figure 25:
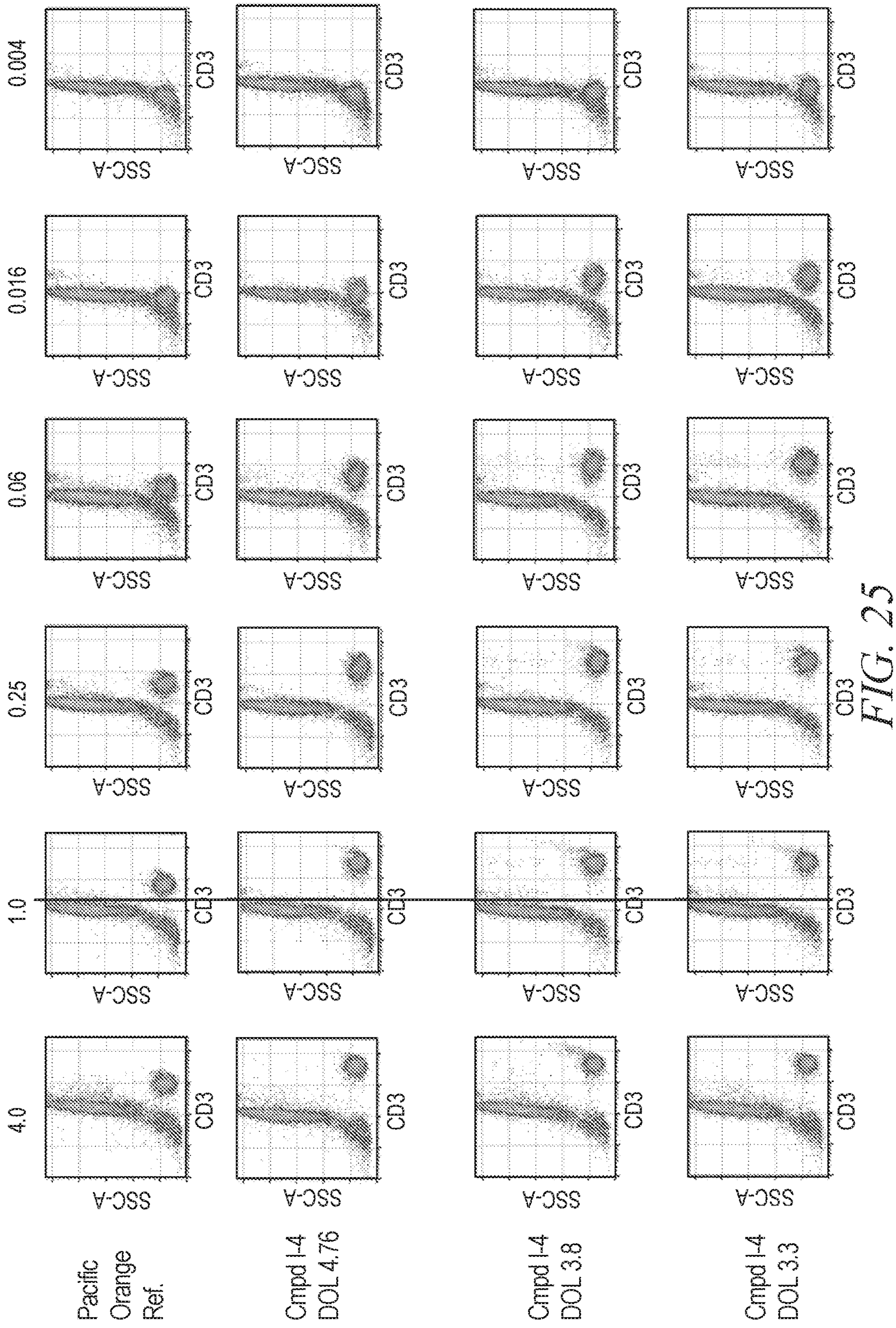
FIG. 25 shows additional representative flow cytometry readouts for samples prepared with a conjugates of UCHT-1 and Pacific Orange or Compound I-4 having a DOL ranging from 3.3 to 4.76.
Figure 26:
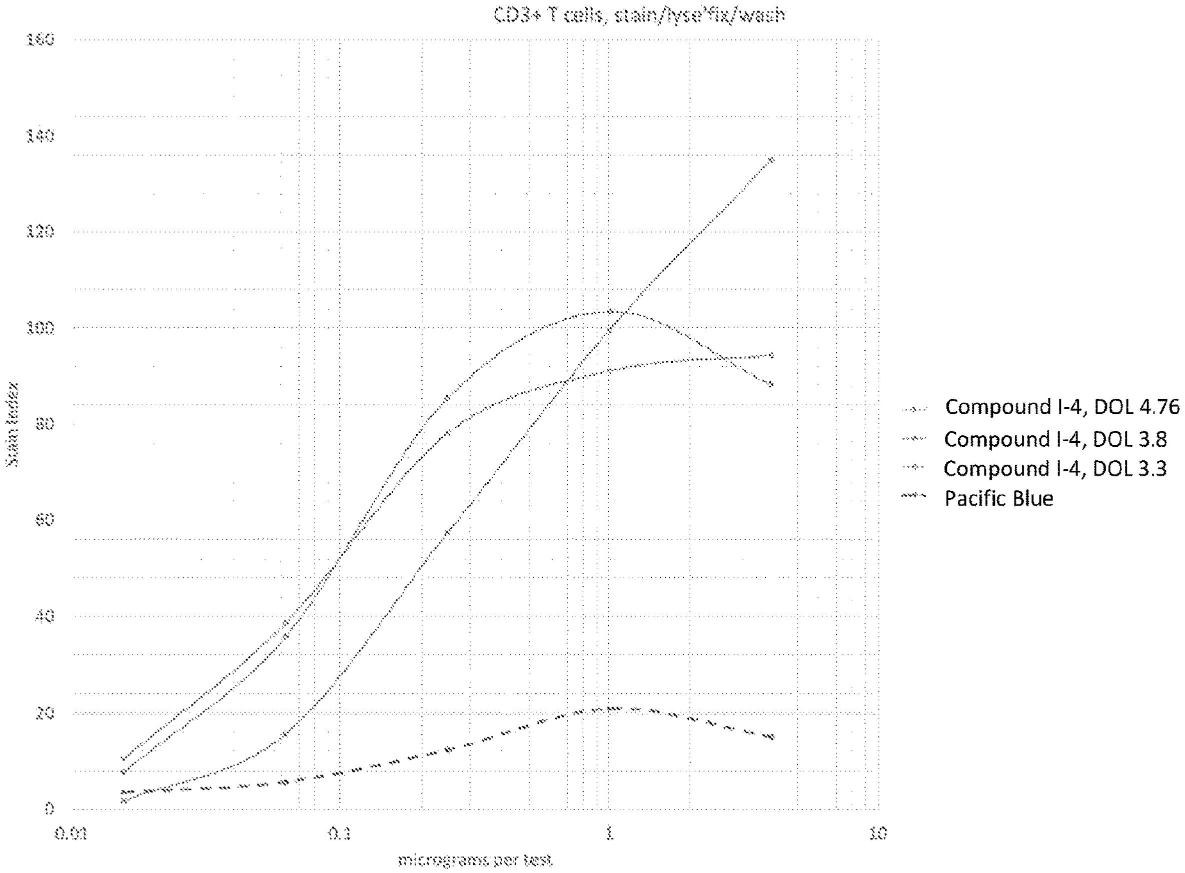
FIG. 26 is an additional representative plot of the stain index against the micrograms per test for a Pacific Orange control and Compound I-4 having a DOL ranging from 3.3 to 4.76.
Figure 27:
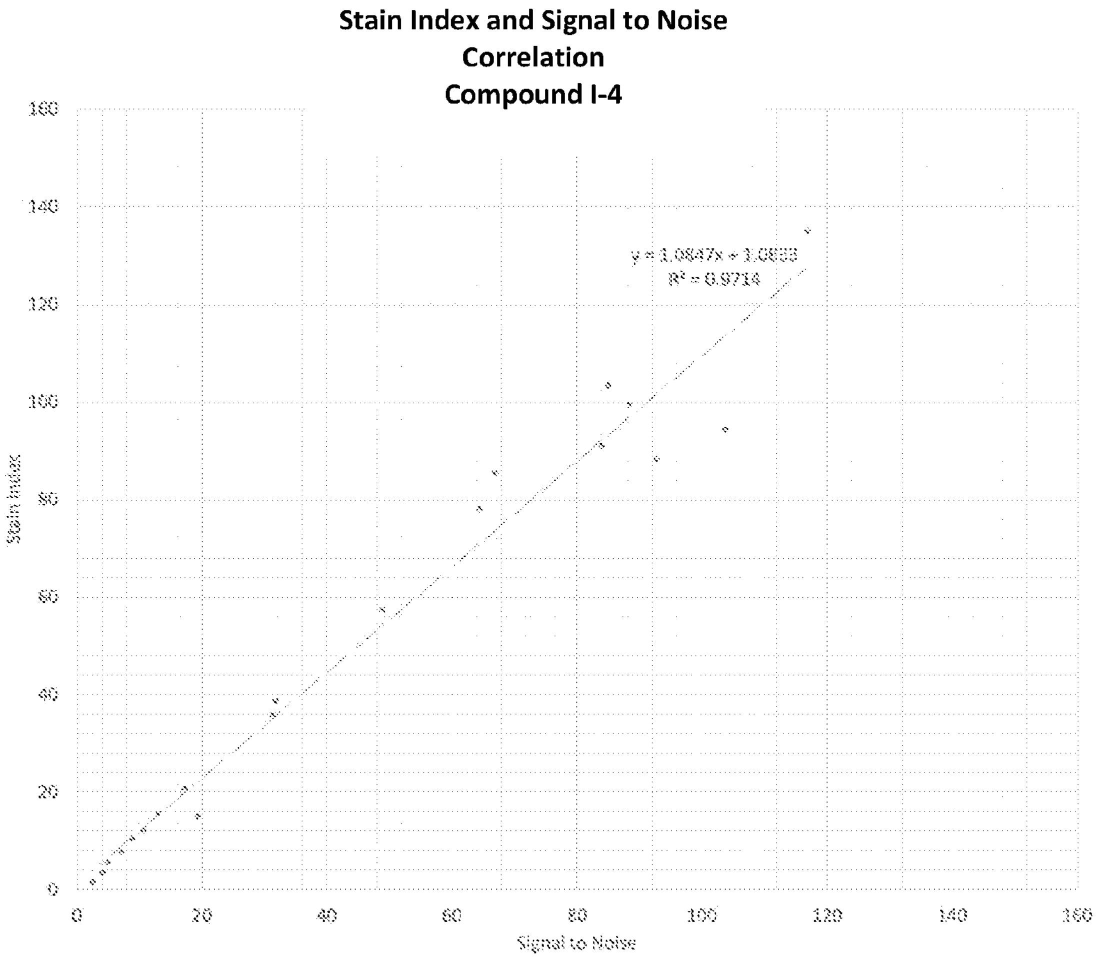
FIG. 27 illustrates the stain index correlation to a signal to noise reading for Compound I-4 (calculated from readings shown in FIG. 25).

Compound I-4 was also tested using 405 nm and a band pass of 605 nm (FIG. 25). Data for stain index plotted for micrograms per test is shown in FIG. 26. A linear regression for the stain index correlation to the signal to noise showed an $R^2$ value of 0.9714 (FIG. 27).

Compound I-5

Figure 12:
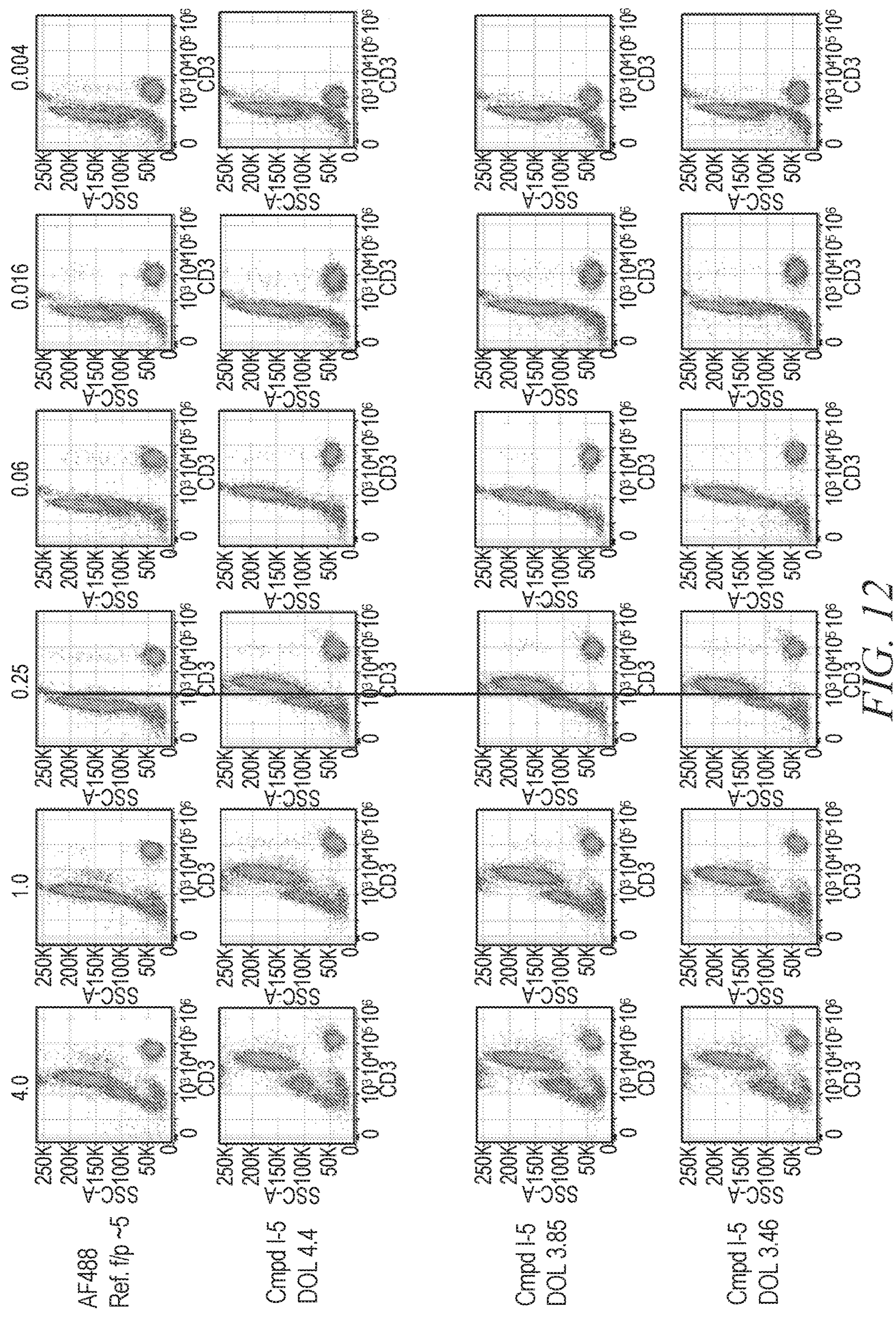
FIG. 12 shows flow cytometry readouts for samples prepared with a conjugates of UCHT-1 and Alexa Fluor 488 and Compound I-5 having a DOL ranging from 3.46 to 4.40.
Figure 13:
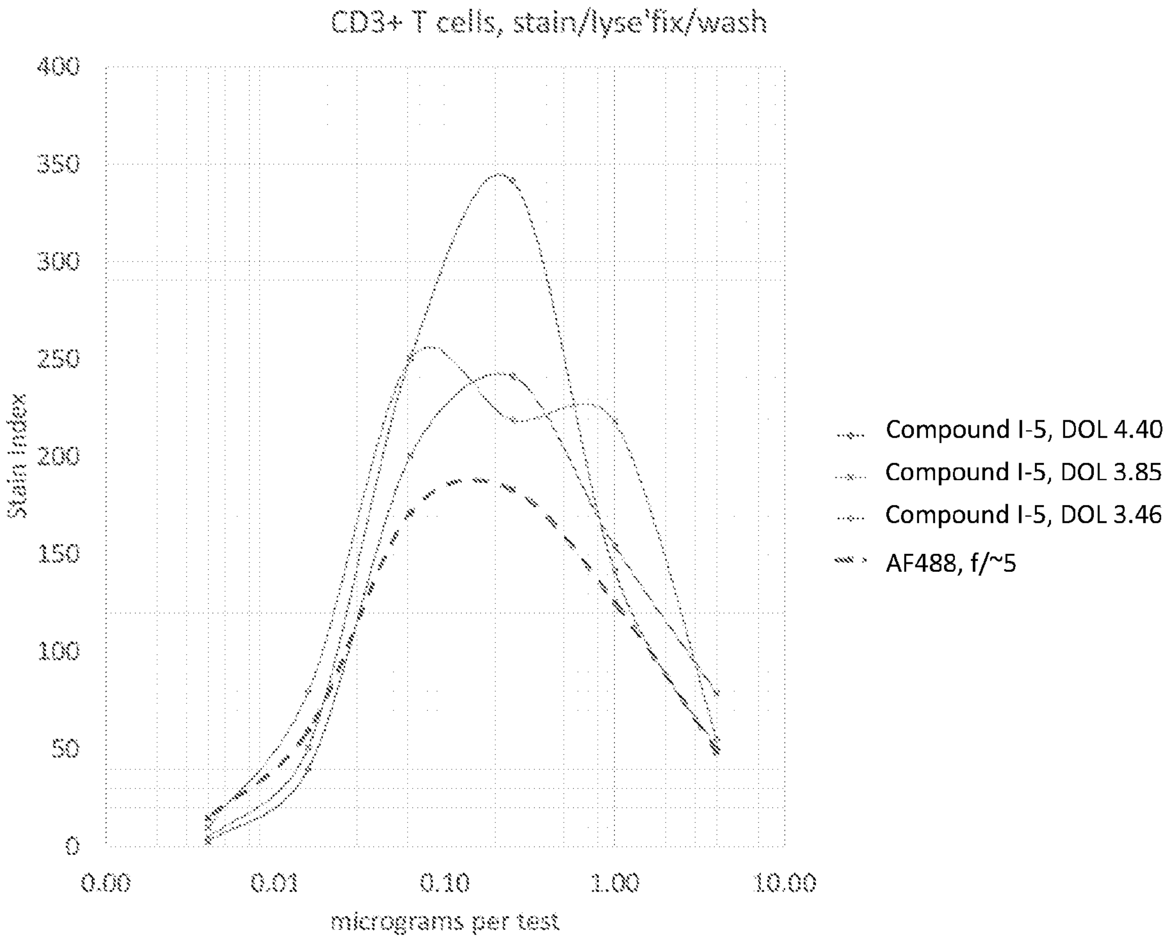
FIG. 13 is a plot of the stain index against the micrograms per test for an samples prepared with Alexa Fluor 488 alone and Compound I-5 having a DOL ranging from 3.46 to 4.40.
Figure 14:
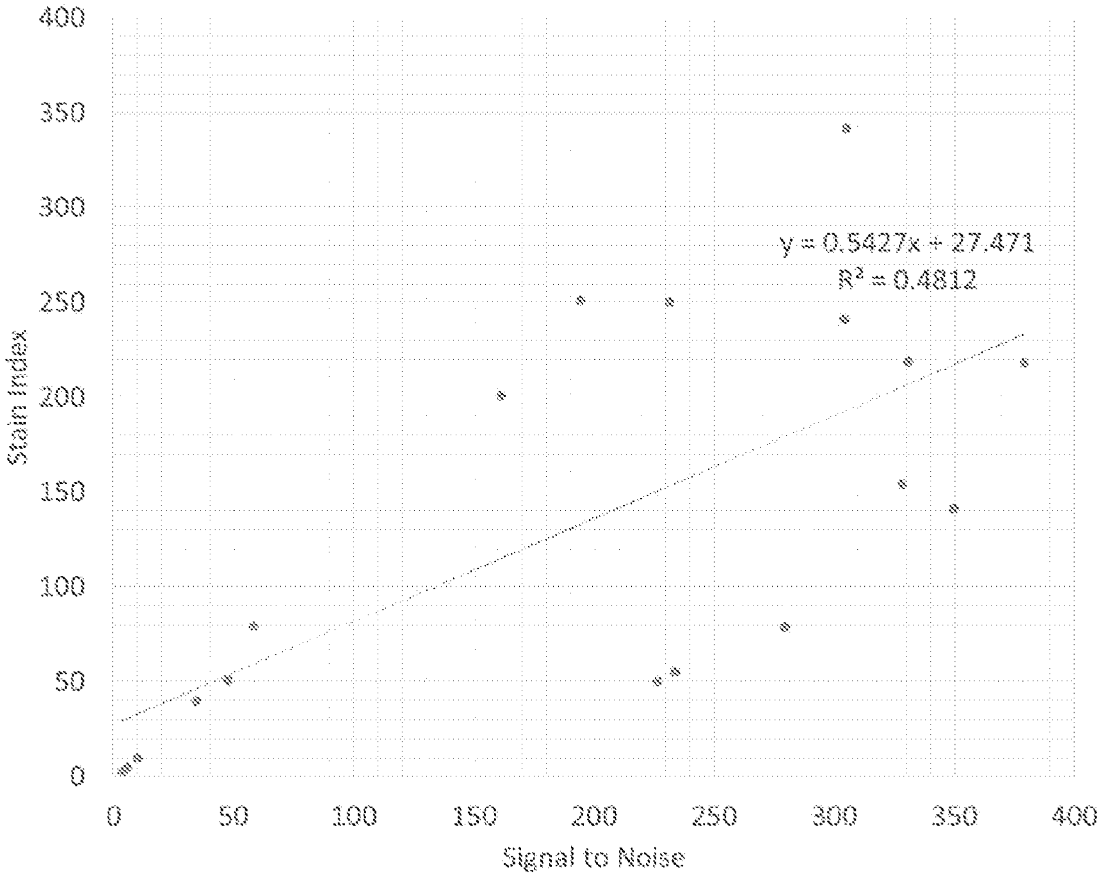
FIG. 14 illustrates the stain index correlation to a signal to noise reading for samples prepared using Compound I-5 (calculated from readings shown in FIG. 5).
Figure 15:
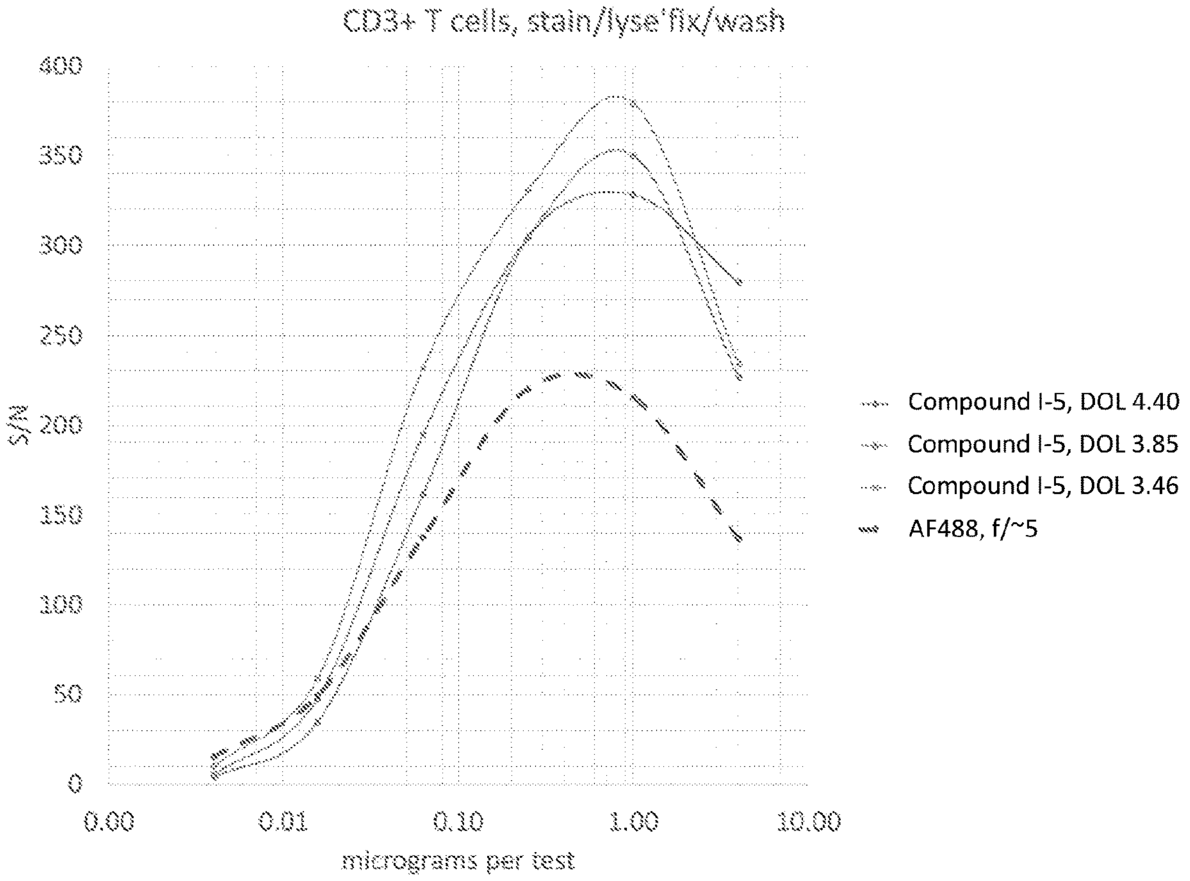
FIG. 15 is a plot of the stain index against the micrograms per test for samples prepared with Alexa Fluor 488 alone versus Compound I-5 having a DOL ranging from 3.46 to 4.40.
Figure 16:
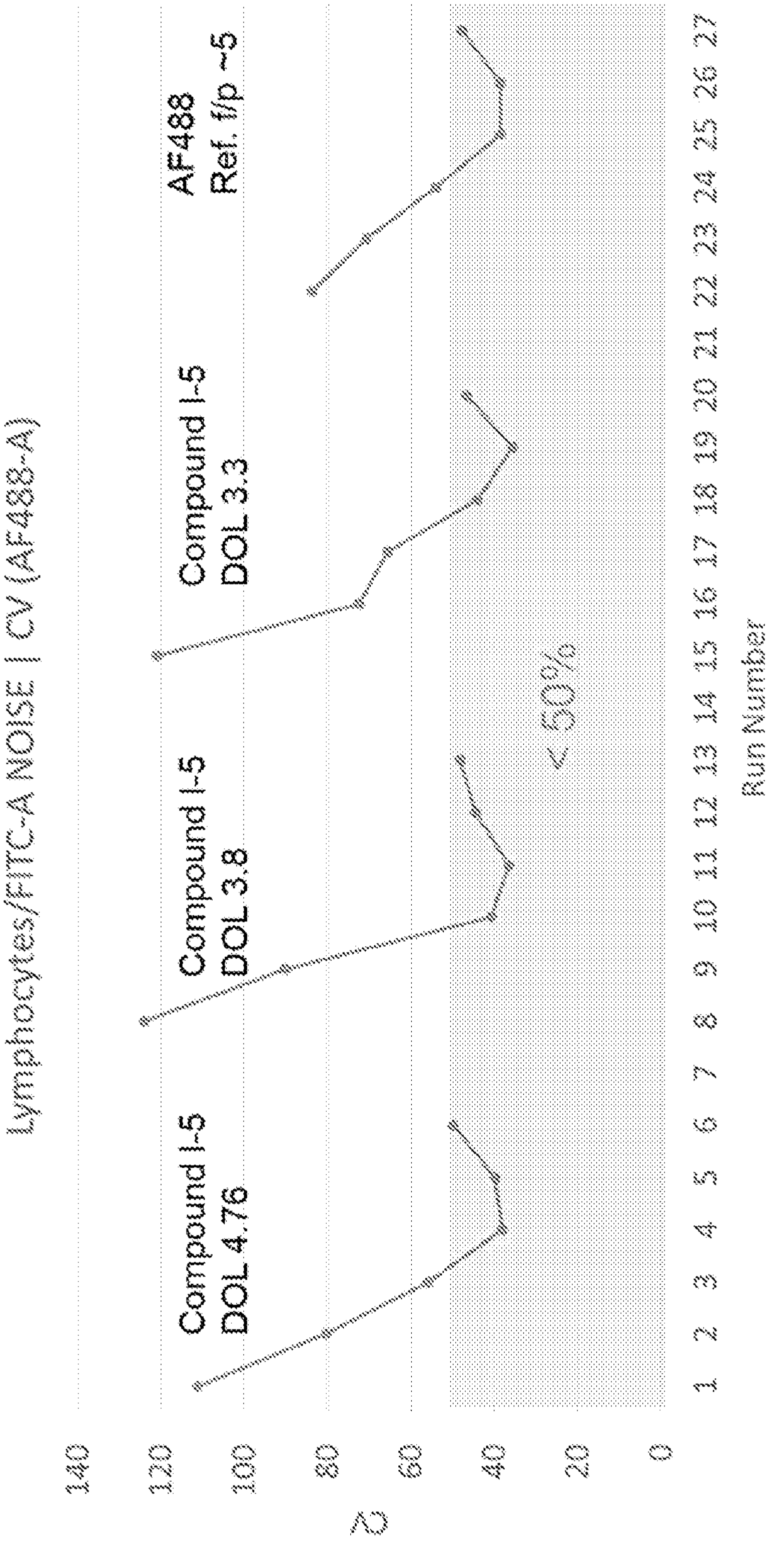
FIG. 16 is a plot of noise for samples prepared using Alexa Fluor 488 compared to Compound I-5 with DOL ranging from 3.3 to 4.76.
Figure 17:
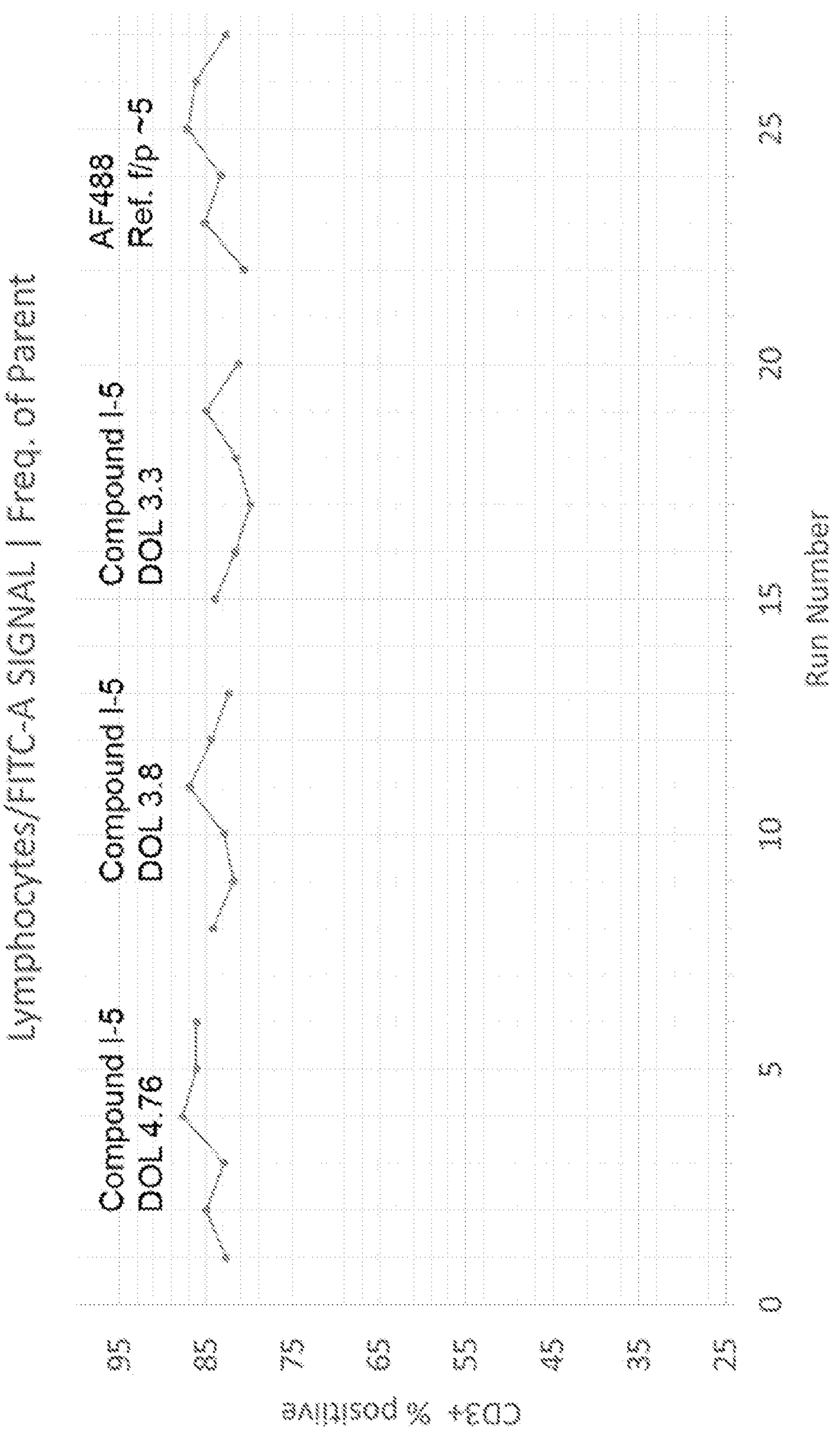
FIG. 17 is a plot of signal for samples prepared with Alexa Fluor 488 compared to Compound I-5 with DOL ranging from 3.3 to 4.76.

Data shown in FIG. 12 was acquired using 488 nm light and a band pass filter at 525 nm. The fluorophore for these compounds have a similar noise profile to fluorescein-types of compounds. The signal data (FIG. 17) indicates that the accuracy of labeling CD3 antigen is similar to the Alexa Fluor 488 conjugate used as a reference.

Compounds I-1, I-2 and I-6

Figure 18:
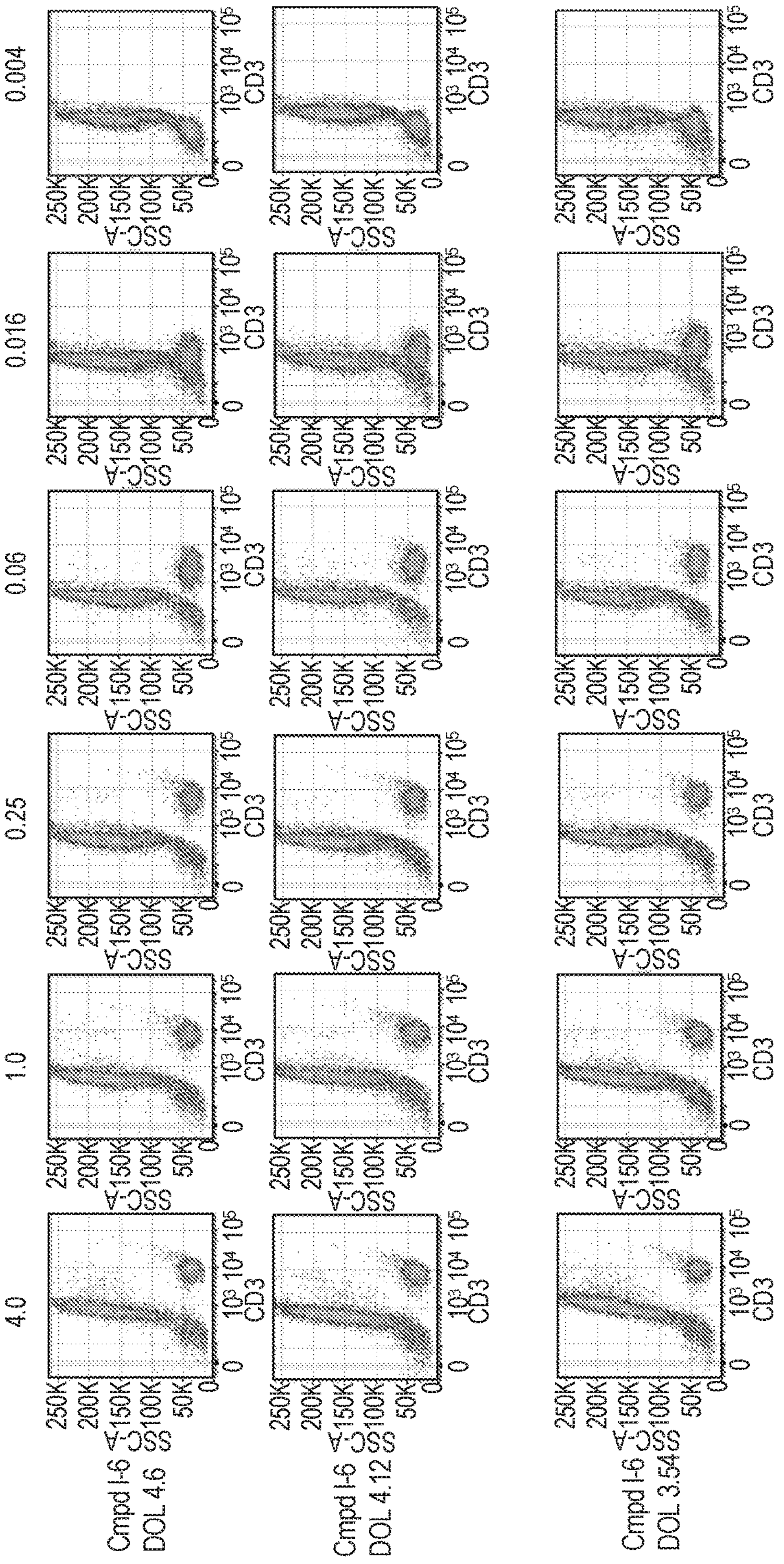
FIG. 18 depicts flow cytometry data acquired from samples prepared with conjugates of UCHT-1 and Compound I-6 having a DOL ranging from 3.54 to 4.6.
Figure 19:
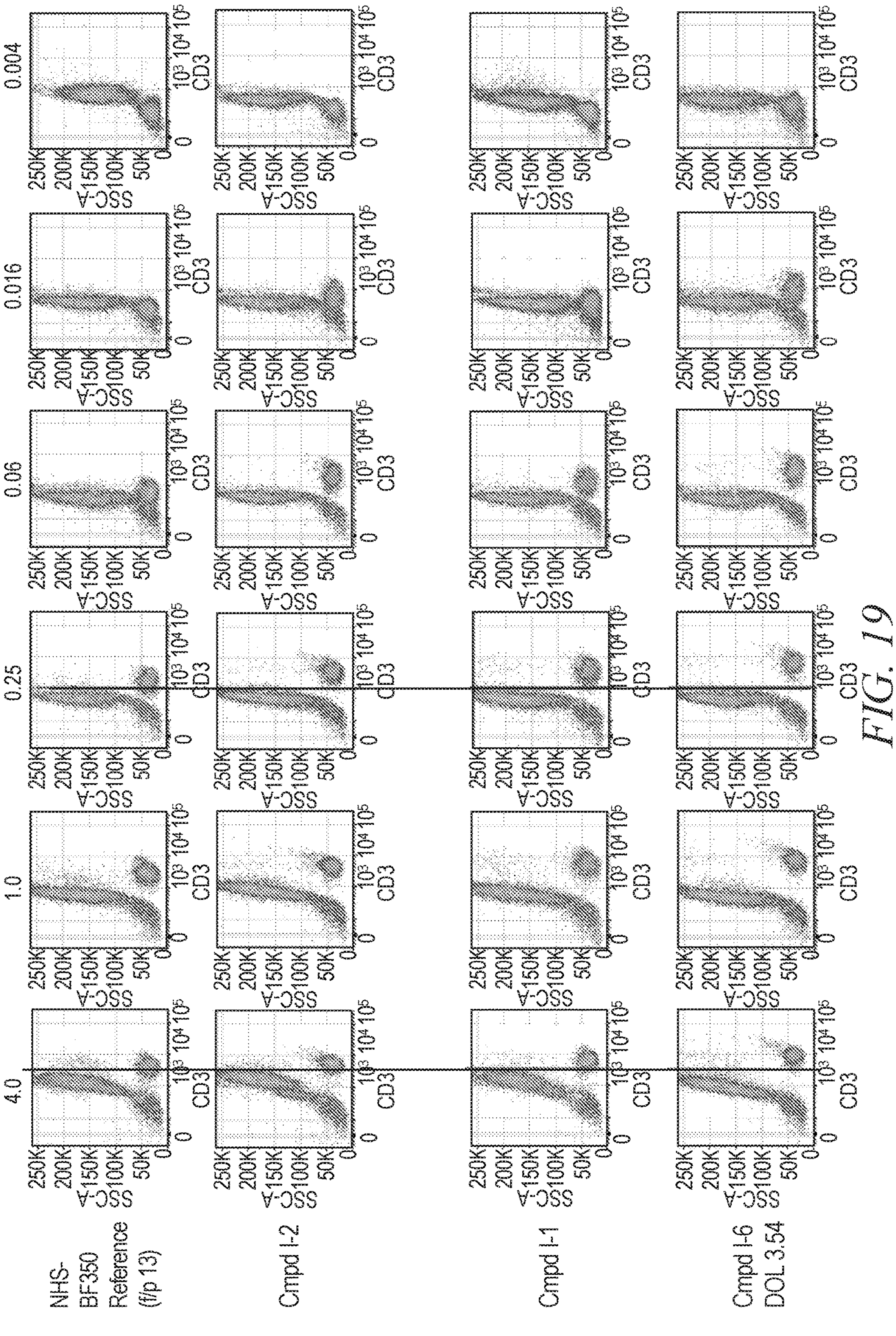
FIG. 19 shows flow cytometry readouts for samples prepared with conjugates of UCHT-1 and Alexa Fluor 350, Compound I-1, Compound I-2 and Compound I-6 having a DOL of 3.54, respectively.
Figure 20:
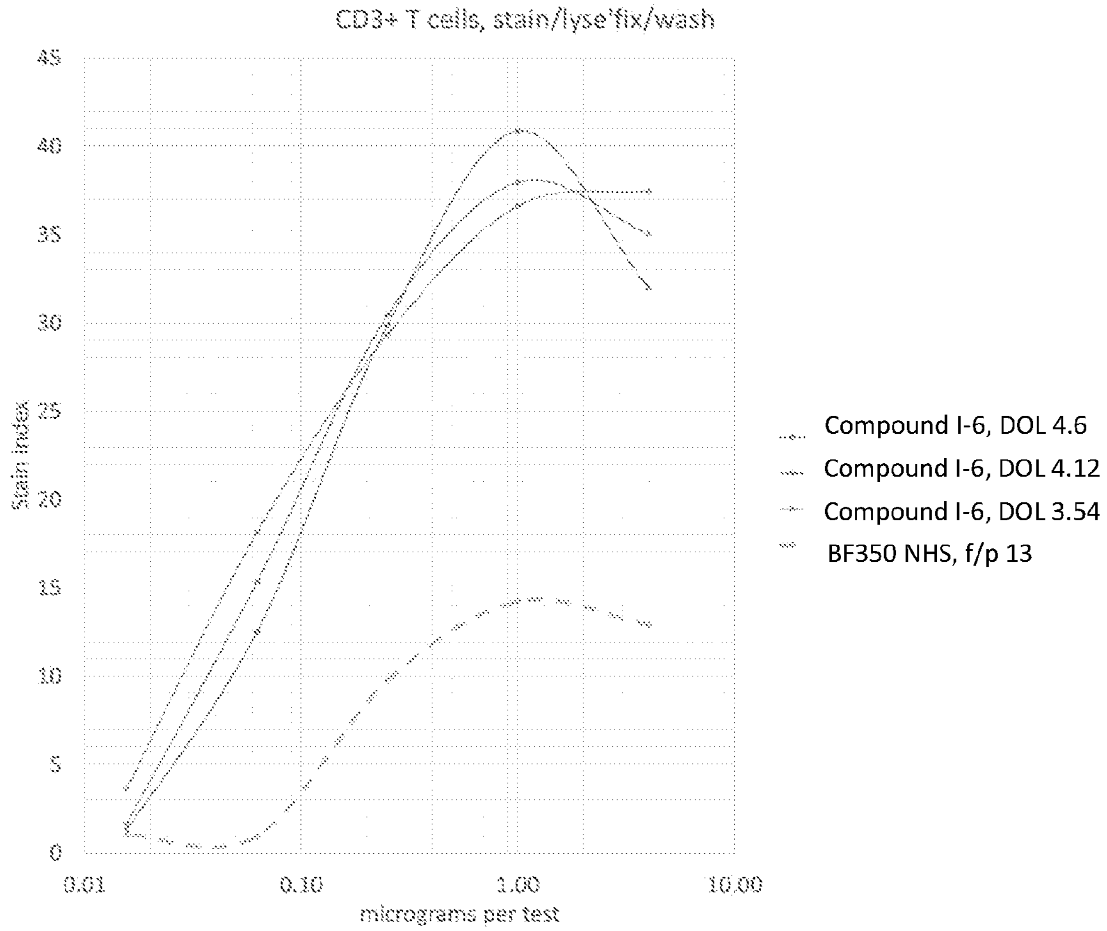
FIG. 20 shows a plot of stain index against micrograms per test for samples prepared with Alexa Fluor 350 control and Compound I-6 having a DOL ranging from 3.54 to 4.6.
Figure 21:
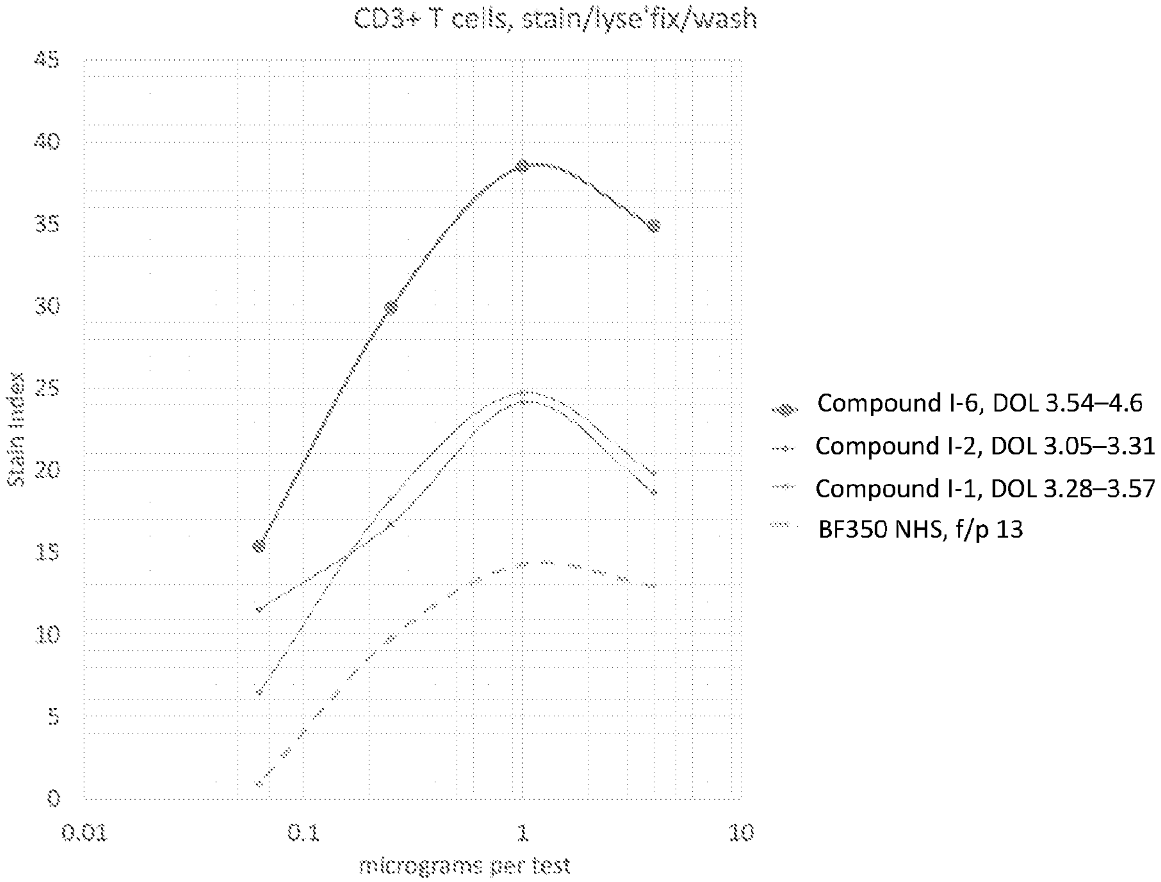
FIG. 21 shows a plot of average stain index against micrograms per test for samples prepared with Compound I-6 having a DOL ranging from 3.54 to 4.6, Compound I-2 having a DOL ranging from 3.05 to 3.31, Compound I-1 having a DOL ranging from 3.28 to 3.57 and a control sample of Alexa Fluor 350 alone.
Figure 22:
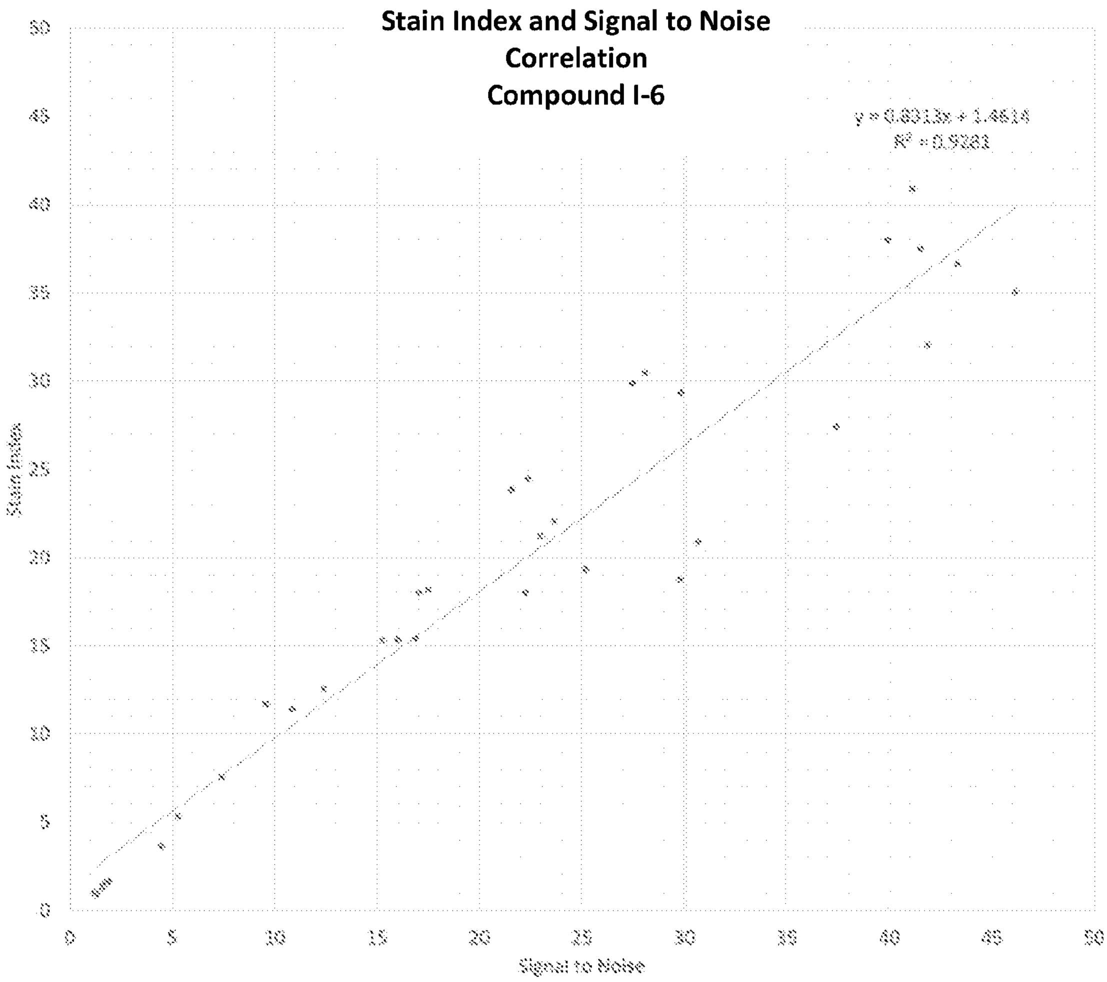
FIG. 22 shows a plot of stain index correlated to a signal to noise reading for samples prepared with Compound I-6 (calculated from readings shown in FIG. 18).
Figure 23:
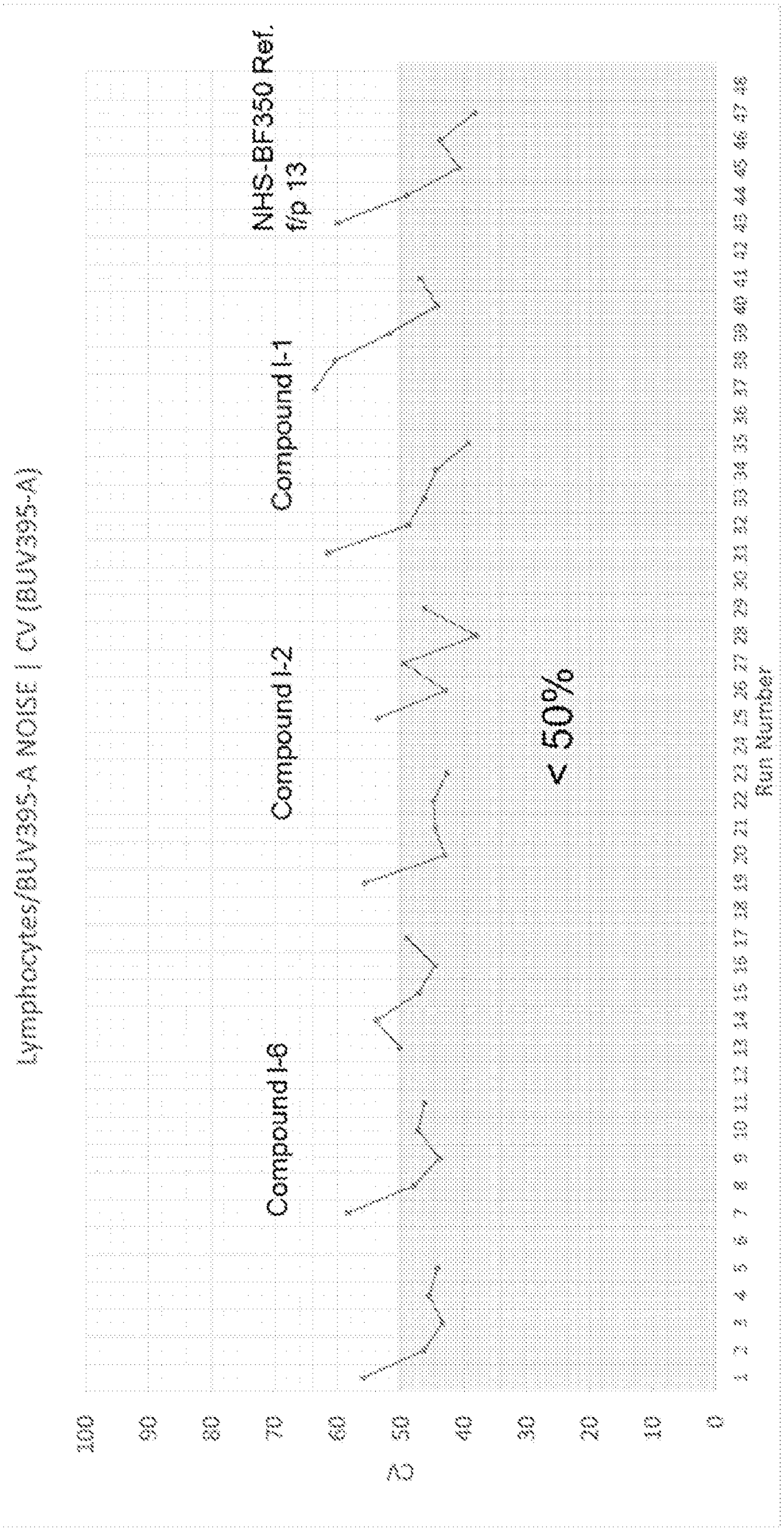
FIG. 23 shows noise for samples prepared using Compound I-6, Compound I-2, Compound I-1 and Alexa Fluor 350, respectively.
Figure 24:
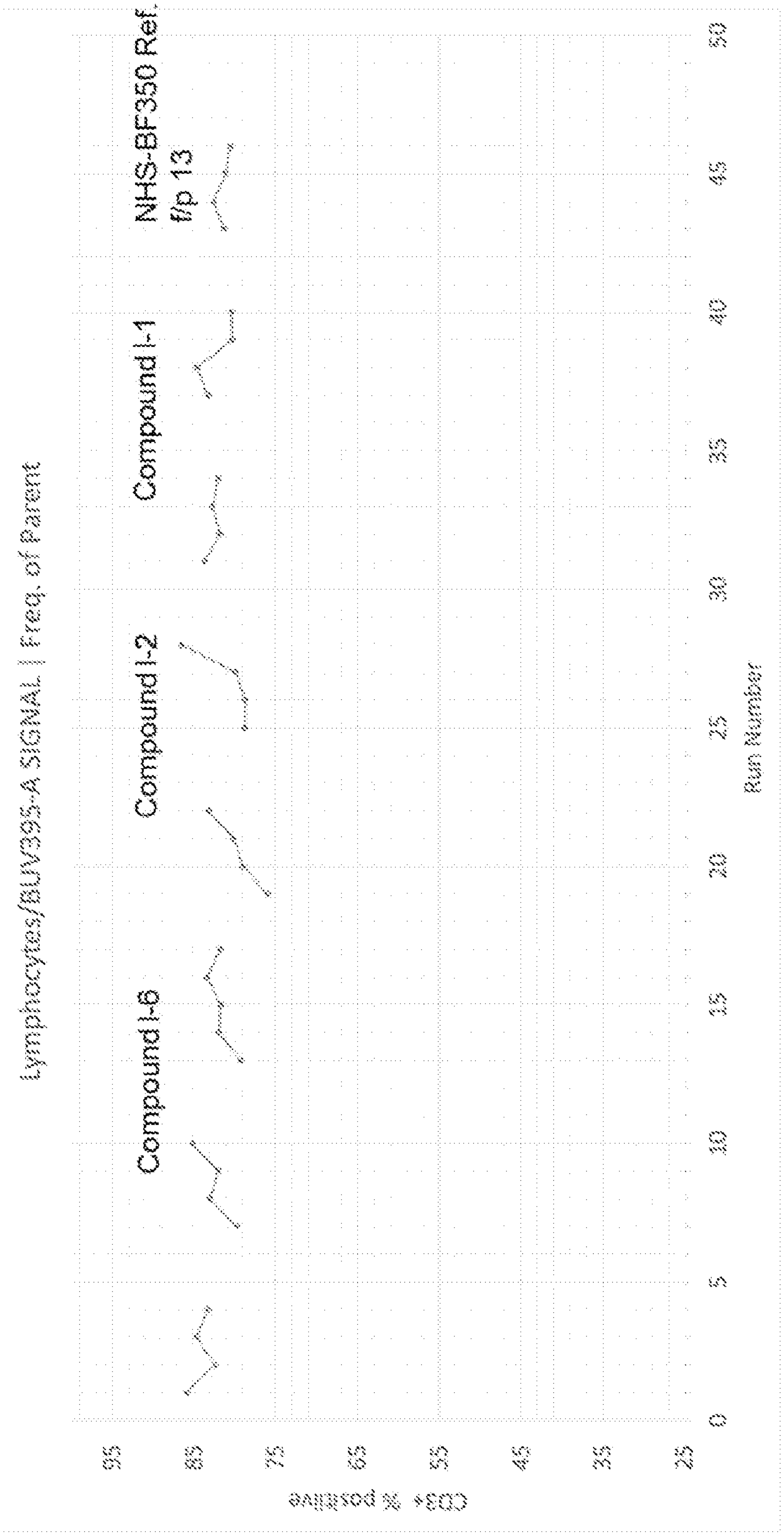
FIG. 24 shows signal for samples prepared using Compound I-6, Compound I-2, Compound I-1 and Alexa Fluor 350, respectively.

Data shown in FIG. 18 was acquired using 355 nm light and a band pass filter at 395 nm (emission max is 442 nm). A reference sample of Alexa Fluor 350, Compound I-1 and Compound I-2, respectively, were prepared for comparison purposes. A comparison of the stain index plotted as a function of the micrograms per test can be found in FIG. 20. As the data show, the stain index is significantly higher for each sample prepared with Compound I-6. Additionally, Compound I-6 shows better stain index values compared to compounds with shorter length PEG components (i.e., Compound I-1 and Compound I-2). A linear regression for the stain index correlation to the signal to noise showed an $R^2$ value of 0.9281 (FIG. 22). Compound I-6, Compound I-1 and Compound I-2 all show noise values that are substantially similar to the Alexa Fluor 350 reference sample (FIG. 23). The signal values in FIG. 24 indicate a similar accuracy of labeling for compounds tested relative to the reference sample.

Example 5

Flow Cytometry Method and Applications

A general flow cytometry workflow includes the following steps:

1. Culture and visually observe cells for signs of metabolic stress and/or use fresh, induced, or simulated cells.
2. Dilute dye compounds to working volumes.
3. Harvest and prepare cells without killing or inducing apoptosis.
4. Centrifuge and wash cells with appropriate buffer.

5. Perform cell counts using hemocytometer and trypan blue exclusion.
6. Centrifuge and wash cells
7. Adjust cell density to test size
8. Apply dye (pre-dilution) or other co-stains of interest.
9. Incubate the cell/stain/dye mixture.
10. Centrifuge and wash cells with appropriate buffer.
11. Re-suspend cells in acquisition buffer.
12. Acquire cell data by flow cytometry.

The general workflow described above can be modified according to specific applications. Some modifications for specific applications are described below.

Live/Dead Discrimination

Cells are tested for viability by positively staining necrotic cells to compare damaged cells to intact cells. Assays are used to target non-intact (fixed and non-fixed) cells with positively charged moieties, cell debris, apoptotic bodies, depolarized cell membrane, and permeabilized membranes. Cells are then stained with dye (e.g., Compound of structure I) using routine cell preparations (fresh or fixed) and analyzed using flow cytometry.

Cell Health

A comparison is made between dead cells (i.e., necrotic cells), early apoptotic, late apoptotic, and live cells. Dead cells are positively stained, Apoprotic bodies are intermediately stained, and live cells are left negative. This strategy results in very bright necrotic cells and works also to assess cell permeability. Assays are used to target non-intact (fixed and non-fixed) cells with positively charged moieties, cell debris, apoptotic bodies, depolarized cell membrane, and permeabilized membranes. Dye staining is performed on in vitro cultures, primary cells, and samples treated with xenobiotics and analyzed using flow cytometry.

Cell Cycle

Cell ploidy and mitosis in the cell cycle is tracked by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with other dyes) is performed on in vitro cultures, primary cells, and samples treated with xenobiotics and analyzed using flow cytometry.

Proliferation

Cell proliferation is monitored by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with monitoring markers for cell proliferation, e.g. Ki67, BRDU) is performed on in vitro cultures, primary cells, and samples treated with xenobiotics and analyzed using flow cytometry.

All of the U.S. patents, U.S. patent application publications, U.S. patent applications, foreign patents, foreign patent applications and non-patent publications referred to in this specification, including U.S. Provisional Patent Application No. 62/697,716, filed on Jul. 13, 2018, are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound having the following structure (In):

(In)

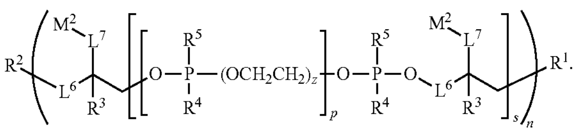

or a stereoisomer, salt or tautomer thereof, wherein:

$M^2$ is, at each occurrence, independently a fluorescent or colored moiety comprising two or more double bonds and at least one degree of conjugation;

$L^6$ and $L^7$ are, at each occurrence, independently optional alkylene, alkenylene, alkynylene, heteroalkylene, heteroalkenylene or heteroalkynylene linkers;

$R^1$ and $R^2$ are each independently H, OH, SH, alkyl, alkoxy, alkylether, heteroalkyl, $—OP(=R_a)(R_b)R_c$, Q, or a protected form thereof, or L';

$R^3$ is, at each occurrence, independently H, alkyl or alkoxy;

$R_a$ is O or S;

$R_b$ is OH, SH, $O^-$, $S^-$, $OR_d$ or $SR_d$;

$R_c$ is OH, SH, $O^-$, $S^-$, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (In);

n is an integer of one or greater;

s is, at each occurrence, independently an integer of 1 or greater;

z is, at each occurrence, independently an integer from 20 to 30;

p is, at each occurrence, independently an integer of one or greater;

$R^4$ is, at each occurrence, independently OH, SH, $O^-$, $S^-$, $OR_d$ or $SR_d$;

$R^5$ is, at each occurrence, independently oxo, thioxo or absent; and at least one occurrence of $M^2$ has one of the following structures:
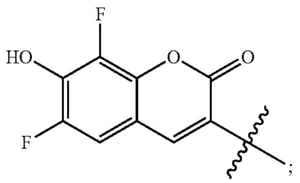
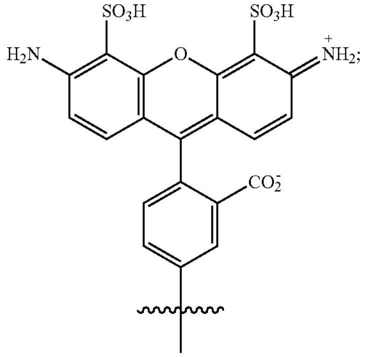
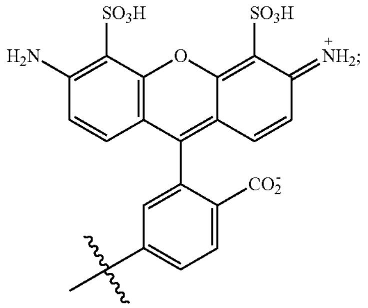
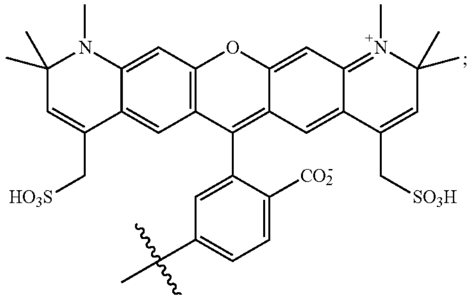
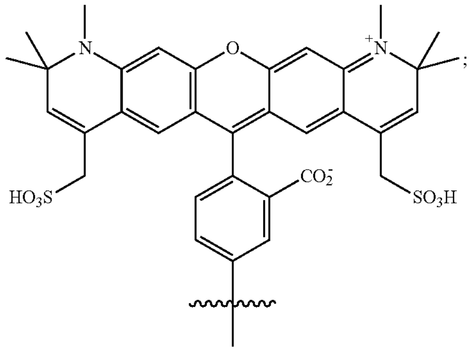
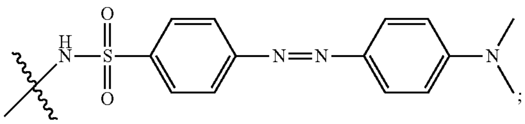
-continued
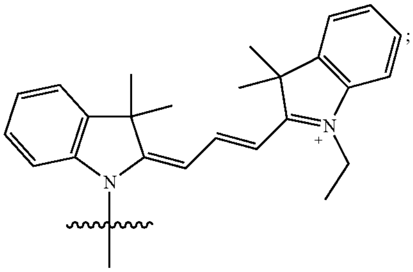
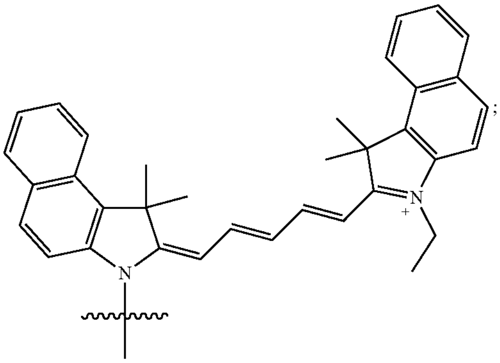
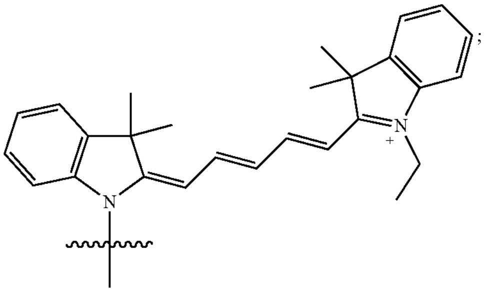
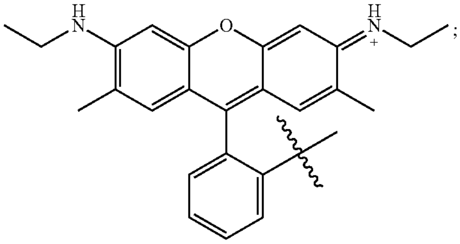
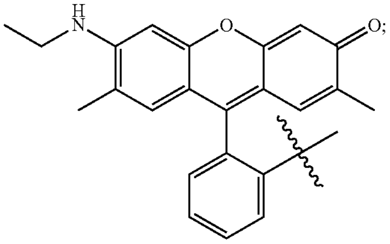
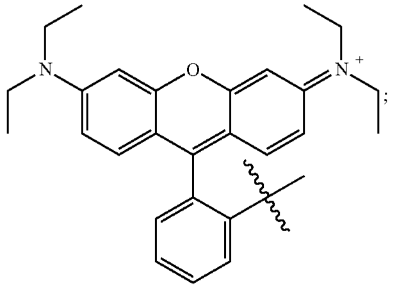

-continued

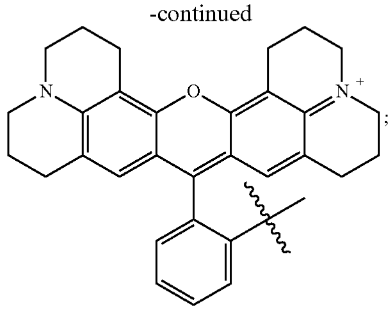

;

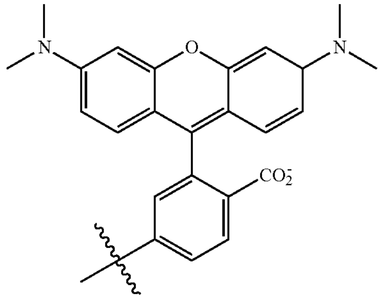

or

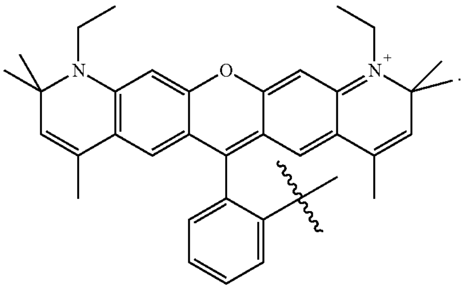

.

-continued

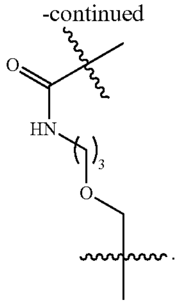

.

2. The compound of claim 1, wherein at least one occurrence of $L^7$ has one of the following structures:

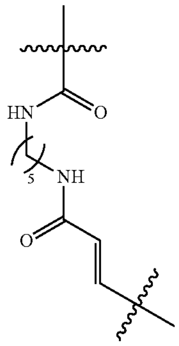

;

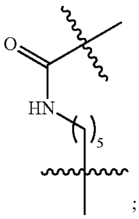

;

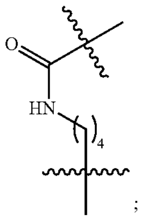

; or

3. The compound of claim 1, wherein at least one occurrence of $R^3$ is H.

4. The compound of claim 1, wherein $L^6$ is absent.

5. The compound of claim 1, wherein $R^4$ is, at each occurrence, OH, $O^-$ or $OR_d$, and $R^5$ is, at each occurrence, independently oxo.

6. The compound of claim 1, wherein one of $R^1$ or $R^2$ is OH or $—OP(=R_a)(R_b)R_c$, and the other of $R^1$ or $R^2$ is Q or a linker comprising a covalent bond to Q.

7. The compound of claim 6, wherein $R_c$ is OL', wherein L' comprises an alkylene oxide or phosphodiester moiety, or combinations thereof.

8. The compound of claim 7, wherein L' has the following structure:

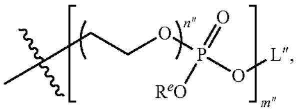

wherein:

m" and n" are independently an integer from 1 to 10;

$R^e$ is H, an electron pair or a counter ion;

L" is $R^e$ or a direct bond or linkage to: Q, a targeting moiety, an analyte molecule, a solid support, a solid support residue, a nucleoside or a further compound of structure (In).

9. The compound of claim 8, wherein the targeting moiety is an antibody or cell surface receptor antagonist.

10. The compound of claim 1, wherein $R^1$ or $R^2$ has one of the following structures:

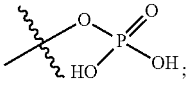

;

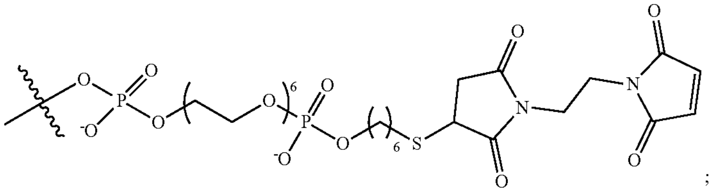

;

-continued

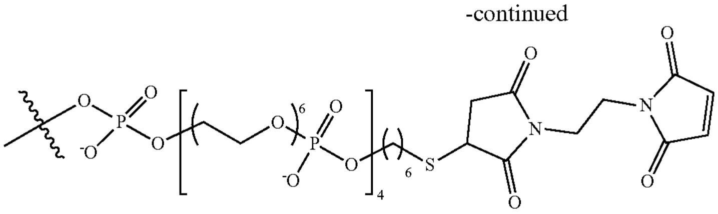
;

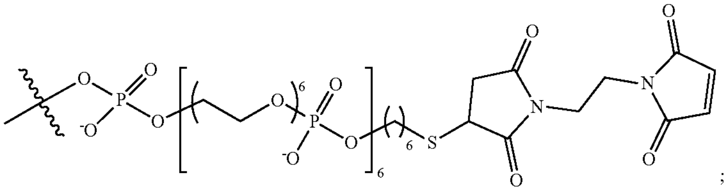
;

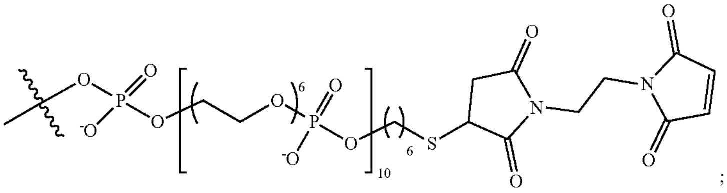
;

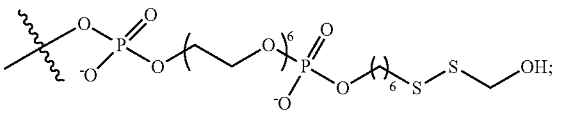

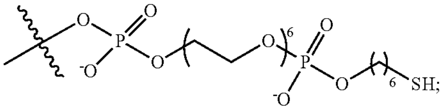

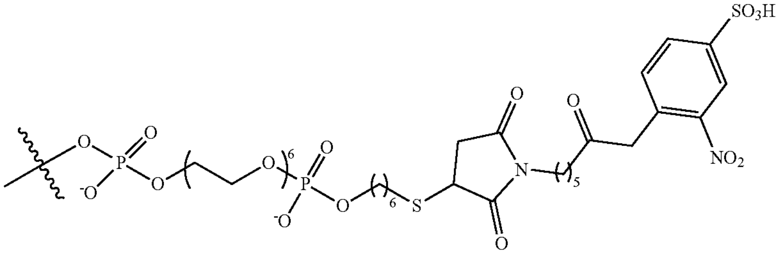
or

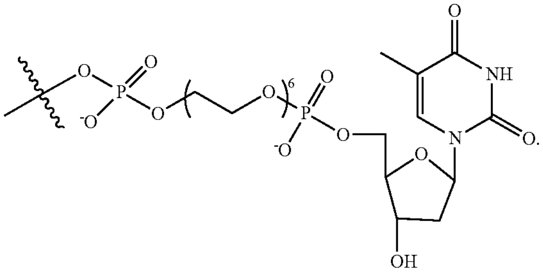

11. The compound of claim 1, wherein Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group.

12. The compound of claim 11, wherein the activated ester is an N-succinimide ester, imidoester or polyflourophenyl ester, and wherein the azide is an alkyl azide or acyl azide.

13. The compound of claim 1, wherein Q is a moiety having one of the following structures:

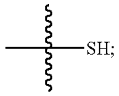

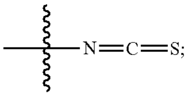

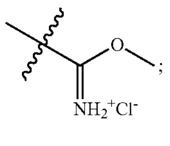

-continued

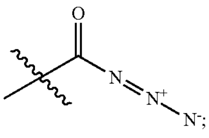

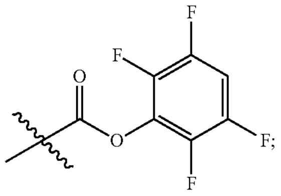

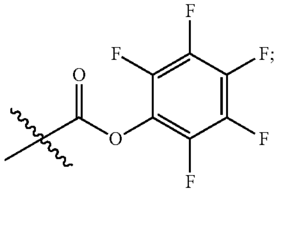

-continued

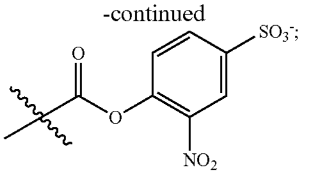

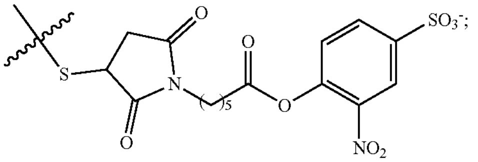

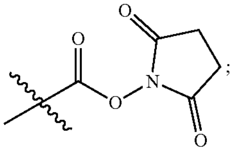

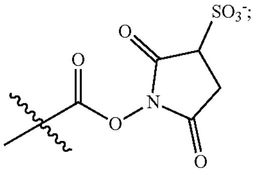

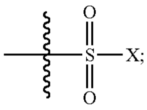

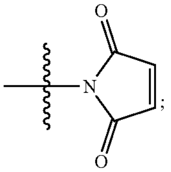

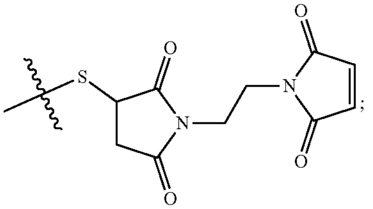

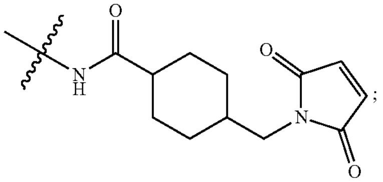

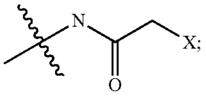

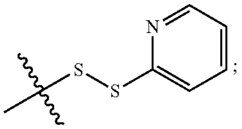

-continued

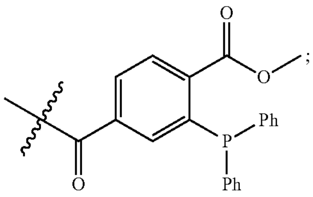

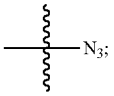

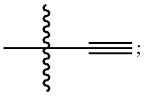

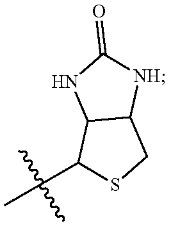

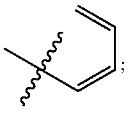

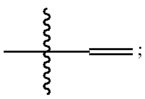

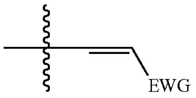

or $-NH_2$, wherein:

X is halo; and

EWG is an electron withdrawing group.

14. The compound of claim 1, wherein one of $R^1$ or $R^2$ is OH or $-OP(=R_a)(R_b)R_c$, and the other of $R^1$ or $R^2$ is a linker comprising a covalent bond to an analyte molecule, a linker comprising a covalent bond to a targeting moiety or a linker comprising a covalent bond to a solid support.

15. The compound of claim 14, wherein the analyte molecule is a nucleic acid, amino acid or a polymer thereof.

16. The compound of claim 14, wherein the analyte molecule is an enzyme, receptor, receptor ligand, antibody, glycoprotein, aptamer or prion.

17. The compound of claim 14, wherein the targeting moiety is an antibody or cell surface receptor antagonist.

18. The compound of claim 14, wherein the solid support is a polymeric bead or non-polymeric bead.

19. The compound of claim 1, wherein n is an integer from 1 to 100.

20. A compound having one of the following structures:

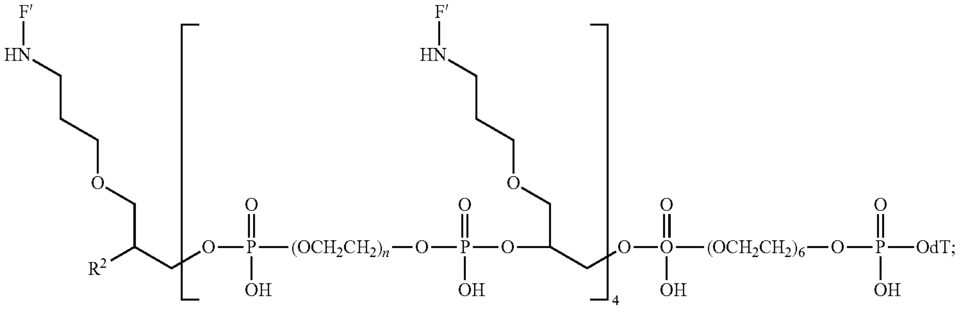

-continued
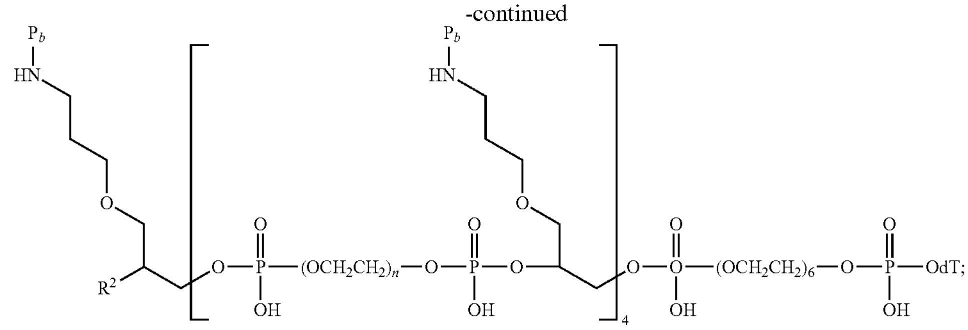
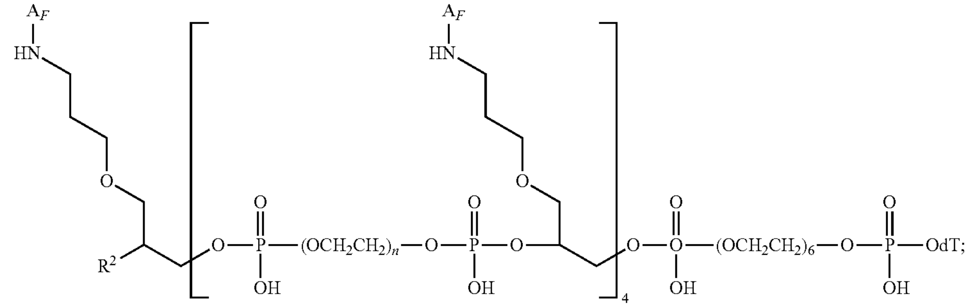
or
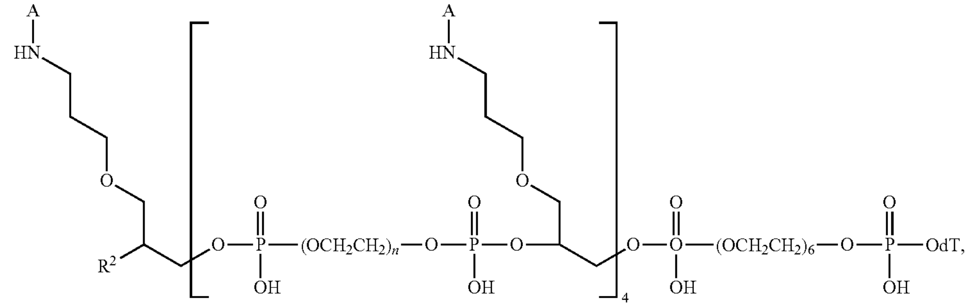
wherein:
A refers to the following structure:
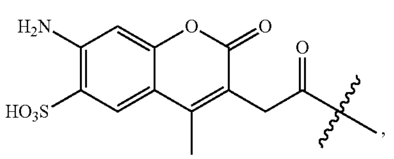 [SMILES: *C(=O)Cc1c(C)c2cc(S(=O)(=O)O)c(N)cc2oc1=O]
F' refers to the following structure:
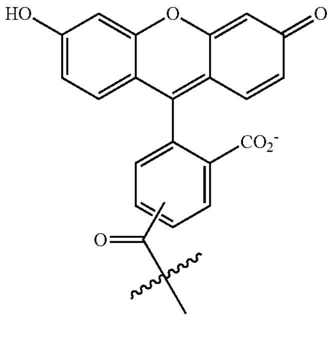
$P_b$ refers to the following structure:
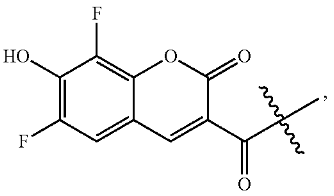 [SMILES: *C(=O)c1cc2cc(F)c(O)c(F)c2oc1=O]
$A_F$ refers to the following structure:
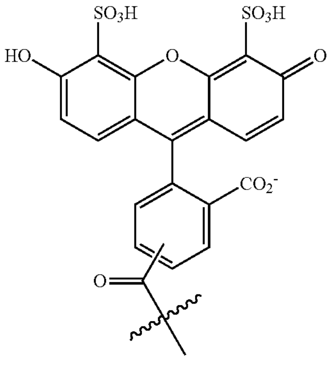

$R^2$ refers to the following structure:

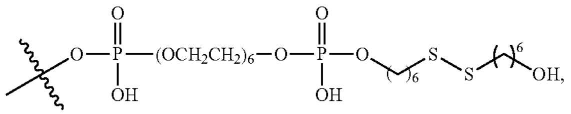

dT refers to the following structure:

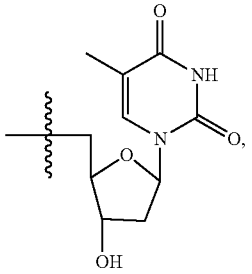 [SMILES: *CC1OC(n2cc(C)c(=O)[nH]c2=O)CC1O]

and n is an integer from 22 to 26.

21. A method of staining a sample, comprising adding to the sample the compound of claim 1 in an amount sufficient to produce an optical response when the sample is illuminated at an appropriate wavelength, wherein the sample comprises cells.

22. A method for visually detecting an analyte molecule, the method comprising:

(a) providing the compound of claim 1, wherein $R^1$ or $R^2$ is a linker comprising a covalent bond to the analyte molecule; and (b) detecting the compound by its visible properties.

23. A method for visually detecting an analyte molecule, the method comprising:

(a) admixing the compound of claim 1, wherein $R^1$ or $R^2$ is Q or a linker comprising a covalent bond to Q, with the analyte molecule;

(b) forming a conjugate of the compound and the analyte molecule; and (c) detecting the conjugate by its visible properties.

24. A method for visually detecting an analyte, the method comprising:

(a) providing the compound of claim 1, wherein $R^1$ or $R^2$ comprises a linker comprising a covalent bond to a targeting moiety having specificity for the analyte;

(b) admixing the compound and the analyte, thereby associating the targeting moiety and the analyte; and (c) detecting the compound by its visible properties.

25. A composition for detection of one or more analyte molecules comprising the compound of claim 1 and the one or more analyte molecules.

* * * * *